(12) United States Patent
Kusumoto et al.

(10) Patent No.: US 9,556,200 B2
(45) Date of Patent: Jan. 31, 2017

(54) TRICYCLIC COMPOUND

(71) Applicant: TAKEDA PHARMACEUTICAL COMPANY LIMITED, Osaka (JP)

(72) Inventors: Tomokazu Kusumoto, Kanagawa (JP); Shigekazu Sasaki, Kanagawa (JP); Hironobu Maezaki, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 75 days.

(21) Appl. No.: 14/381,347

(22) PCT Filed: Mar. 6, 2013

(86) PCT No.: PCT/JP2013/056154
§ 371 (c)(1),
(2) Date: Aug. 27, 2014

(87) PCT Pub. No.: WO2013/133325
PCT Pub. Date: Sep. 12, 2013

(65) Prior Publication Data
US 2015/0045351 A1    Feb. 12, 2015

(30) Foreign Application Priority Data

Mar. 6, 2012    (JP) .................................. 2012-049431

(51) Int. Cl.
*A61K 31/55* (2006.01)
*C07D 487/06* (2006.01)
*C07D 495/06* (2006.01)
*C07D 491/06* (2006.01)

(52) U.S. Cl.
CPC ........... *C07D 495/06* (2013.01); *C07D 487/06* (2013.01); *C07D 491/06* (2013.01)

(58) Field of Classification Search
CPC .............................. A61K 31/55; C07D 487/06
USPC .......................................... 514/215; 540/577
See application file for complete search history.

(56) References Cited

U.S. PATENT DOCUMENTS

| 4,959,360 | A | 9/1990 | Lafferty et al. |
| 4,963,547 | A | 10/1990 | Lafferty et al. |
| 4,978,660 | A | 12/1990 | Lafferty et al. |
| 5,006,521 | A | 4/1991 | Lafferty et al. |
| 2006/0003990 | A1 | 1/2006 | Bennani et al. |
| 2007/0191342 | A1 | 8/2007 | Tumey et al. |
| 2008/0293694 | A1 | 11/2008 | Angbrant et al. |
| 2009/0131402 | A1 | 5/2009 | Shirai et al. |
| 2010/0087418 | A1 | 4/2010 | Shirai et al. |
| 2010/0190722 | A1 | 7/2010 | Bevec et al. |
| 2010/0266504 | A1 | 10/2010 | Matsumoto et al. |
| 2011/0112072 | A1 | 5/2011 | Tumey et al. |
| 2012/0165312 | A1 | 6/2012 | Shirai et al. |
| 2012/0253036 | A1 | 10/2012 | Nagakura et al. |
| 2014/0206672 | A1 | 7/2014 | Tumey et al. |

FOREIGN PATENT DOCUMENTS

| DE | 35 25 564 | * | 2/1987 |
| JP | 63-501361 | | 5/1988 |
| JP | 2-32081 | | 2/1990 |
| JP | 3-504604 | | 10/1991 |
| JP | 3-504606 | | 10/1991 |

(Continued)

OTHER PUBLICATIONS

International Search Report issued Apr. 2, 2013 in International (PCT) Application No. PCT/JP2013/056154.
Maryanoff et al., "Azepinoindole Derivatives with High Affinity for Brain Dopamine and Serotonin Receptors", Bioorganic & Medicinal Chemistry Letters, vol. 8, 1998, pp. 983-988.
Supplementary European Search Report issued Jan. 19, 2015 in corresponding European Application No. 13757278.0.

(Continued)

*Primary Examiner* — Brenda Coleman
(74) *Attorney, Agent, or Firm* — Wenderoth, Lind & Ponack, L.L.P.

(57) ABSTRACT

The present invention provides a compound having a superior serotonin 5-HT$_{2C}$ receptor activating action.
The present invention relates to a compound represented by the formula (1)

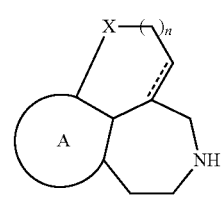

(1)

wherein
ring A is an aromatic carbocycle optionally having substituent(s) or an aromatic heterocycle optionally having substituent(s),
X is —N(R$^1$)—, —O— or the like,
when ring A is an aromatic carbocycle optionally having substituent(s), then R$^1$ is a hydrogen atom, an alkyl group optionally having substituent(s), or the like, and
when ring A is an aromatic heterocycle optionally having substituent(s), then R$^1$ is a hydrogen atom, an alkyl group optionally having substituent(s), a cycloalkyl group optionally having substituent(s), or the like,

------ is a single bond or a double bond, and
n is an integer of 0, 1 or 2,
or a salt thereof.

8 Claims, No Drawings

(56) References Cited

FOREIGN PATENT DOCUMENTS

| | | |
|---|---|---|
| JP | 3-504607 | 10/1991 |
| JP | 2008-505101 | 2/2008 |
| JP | 2009-523809 | 6/2009 |
| JP | 2010-520917 | 6/2010 |
| WO | 2007/084622 | 7/2007 |
| WO | 2007/132841 | 11/2007 |
| WO | 2008/108445 | 9/2008 |
| WO | 2008/110598 | 9/2008 |
| WO | 2009/063992 | 5/2009 |
| WO | 2011/071136 | 6/2011 |

OTHER PUBLICATIONS

Martin et al., "5-HT$_{2c}$ Receptor Agonists: Pharmacological Characteristics and Therapeutic Potential", The Journal of Pharmacology and Experimental Therapeutics, vol. 286, No. 2, 1998, pp. 913-924.

* cited by examiner

TRICYCLIC COMPOUND

TECHNICAL FIELD

The present invention relates to a tricyclic compound having a superior serotonin 5-$HT_{2C}$ receptor activating action and useful as an agent for treatment or the prophylaxis of a lower urinary tract symptom, obesity and/or organ prolapse etc., and the like.

BACKGROUND ART

Serotonin 5-$HT_{2C}$ receptor is one of the receptors of the biological transmitter serotonin, which is distributed mainly in the central nervous system and controls many physiological functions in vivo. A representative example is the control of appetite. It has been demonstrated in a study using rodents that stimulation of the central serotonin 5-$HT_{2C}$ receptor decreases eating behavior, resulting in decreased body weight. It has also been reported that, in human as well, administration of a serotonin 5-$HT_{2C}$ receptor activator suppresses appetite and decreases body weight (see non-patent document 1). In addition, it has been demonstrated in a rat test using a serotonin 5-$HT_{2C}$ receptor activator that stimulation of the central serotonin 5-$HT_{2C}$ receptor suppresses depression-related behaviors (see non-patent document 2), and has also been reported to be effective for many central nervous diseases such as anxiety etc. (see non-patent document 3).

The serotonin 5-$HT_{2C}$ receptor is also highly expressed in the parasympathetic nucleus and motor neurons in the sacral spinal cord, and is considered to control the peripheral nervous functions (see non-patent document 4). It has been reported that when a serotonin 5-$HT_{2C}$ receptor activator is administered to rats, penile erection is induced (see non-patent document 5), and urethral resistance is increased (see patent document 1); all these actions are attributed to stimulation of the serotonin 5-$HT_{2C}$ receptor in the sacral spinal cord.

For serotonin 5-$HT_{2C}$ receptor activators, many clinical applications are likely, with particular expectations for anti-obesity drugs, anti-depressants, anti-anxiety drugs, therapeutic drugs for male erectile dysfunction, and therapeutic drugs for stress urinary incontinence and the like.

As serotonin 5-$HT_{2C}$ receptor compounds, the following compounds have been reported.

Thiophenyl or pyrrolylazepine compound has been disclosed as a therapeutic drug for addiction, anxiety, depression, obesity and the like (see Patent Document 2), and fibromyalgia therapeutic effect of a serotonin 5-$HT_{2C}$ receptor agonist compound has been reported (see Patent Document 3). It has also been reported that compounds having no serotonin 5-$HT_2$ receptor agonist action are found out as psychotropic agent for central nerve (see Non-Patent Document 6). There is a demand for the development of compounds having useful efficacy and the like, however, none of the documents have been reported the compound of the present invention.

Non-Patent Document 1: Expert Opinion on Investigational Drugs, 2006, vol. 15, page 257
Non-Patent Document 2: J. Pharmacol. Exp. Ther., 1998, vol. 286, page 913
Non-Patent Document 3: Pharmacology Biochemistry Behavior, 2002, vol. 71, page 533
Non-Patent Document 4: Neuroscience, 1999, vol. 92, page 1523
Non-Patent Document 5: Eur. J. Pharmacol., 2004, vol. 483, page 37
Non-Patent Document 6: Bioorg. Med. Chem. Lett., 1998, vol. 8, page 983
Patent Document 1: WO 2004/096196 pamphlet
Patent Document 2: WO 2007/084622 pamphlet
Patent Document 3: WO 2011/071136 pamphlet

SUMMARY OF THE INVENTION

Problems to be Solved by the Invention

An object of the present invention is to provide compound a having a serotonin 5-$HT_{2C}$ receptor activating action, which is useful as an agent for the prophylaxis or treatment of lower urinary tract symptom, obesity and/or organ prolapse and the like, and having superior properties in terms of efficacy, duration of action, specificity, low toxicity and the like.

Means of Solving the Problems

The present inventors have conducted intensive studies in an attempt to solve the above-mentioned problem and found that a compound represented by the formula (1) has a superior serotonin 5-$HT_{2C}$ receptor activating action, which resulted in the completion of the present invention.

Accordingly, the present invention provides
[1] a compound represented by the formula (1)

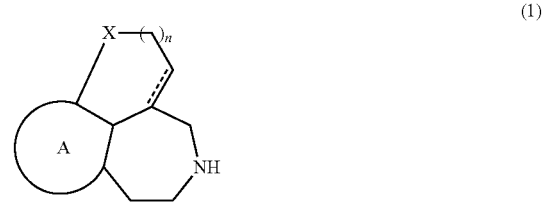

wherein
ring A is an aromatic carbocycle optionally having substituent(s) or an aromatic heterocycle optionally having substituent(s),
X is —N($R^1$)—, —O—, —S—, —S(O)$_2$— or —S(O)—,
when ring A is an aromatic carbocycle optionally having substituent(s), then $R^1$ is a hydrogen atom, an alkyl group optionally having substituent(s), a cycloalkyl group optionally having substituent(s), an alkylcarbonyl group optionally having substituent(s), an arylcarbonyl group optionally having substituent(s), an alkoxycarbonyl group optionally having substituent(s), an alkylsulfonyl group optionally having substituent(s) or an alkylsulfinyl group optionally having substituent(s), and
when ring A is an aromatic heterocycle optionally having substituent(s), then $R^1$ is a hydrogen atom, a cycloalkyl group optionally having substituent(s), an alkylcarbonyl group optionally having substituent(s), an arylcarbonyl group optionally having substituent(s), an alkoxycarbonyl group optionally having substituent(s), an alkylsulfonyl group optionally having substituent(s) or an alkylsulfinyl group optionally having substituent(s),
------ is a single bond or a double bond, and
n is an integer of 0, 1 or 2,
or a salt thereof,

[2] a compound represented by the formula (2)

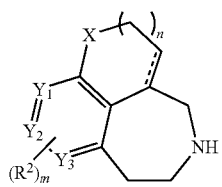

(2)

wherein
X is —N(R$^1$)—, —O—, —S—, —S(O)$_2$— or —S(O)—,
R$^1$ is a hydrogen atom, an alkyl group optionally having substituent(s), a cycloalkyl group optionally having substituent(s), an alkylcarbonyl group optionally having substituent(s), an arylcarbonyl group optionally having substituent(s), an alkoxycarbonyl group optionally having substituent(s), an alkylsulfonyl group optionally having substituent(s) or an alkylsulfinyl group optionally having substituent(s),
------ is a single bond or a double bond,
Y$_1$, Y$_2$ and Y$_3$ are all carbon atoms, or any one of Y$_1$, Y$_2$ and Y$_3$ is a nitrogen atom, and the other two are carbon atoms,
R$^2$ are the same or different and each is a hydrogen atom, a halogen atom, an alkyl group optionally having substituent(s), an alkoxy group optionally having substituent(s), an alkoxycarbonyl group optionally having substituent(s), an alkylcarbonyl group optionally having substituent(s), an aryl group optionally having substituent(s), an amino group, or an N-alkylamino group,
m is an integer of 1, 2 or 3, and
n is an integer of 0, 1 or 2,
or a salt thereof,
[3] the compound or salt of the above-mentioned [1] or [2], wherein n is 0,
[4] the compound or salt of the above-mentioned [2], wherein n is 0, and Y$_1$, Y$_2$ and Y$_3$ are all carbon atoms,
[5] the compound or salt of the above-mentioned [2] or [4], wherein R$^2$ is a halogen atom or an alkyl group optionally having substituent(s),
[6] the compound or salt of the above-mentioned [2] or [4], wherein X is —N(R$^1$)—,
[7] (2aS)-9-chloro-1-isopropyl-2,2a,3,4,5,6-hexahydro-1H-azepino[3,4,5-cd]indole, or a salt thereof,
[8] 9-chloro-2,2a,3,4,5,6-hexahydro-1H-azepino[3,4,5-cd]indole, or a salt thereof,
[9] 9-isopropyl-1-methyl-2,2a,3,4,5,6-hexahydro-1H-azepino[3,4,5-cd]indole, or a salt thereof,
[10] a medicament comprising the compound or salt of the above-mentioned [1] or [2],
[11] the medicament of the above-mentioned [10], which is a serotonin 5-HT$_{2C}$ receptor activator,
[12] the medicament of the above-mentioned [10], which an agent for the prophylaxis or treatment of lower urinary tract symptom, obesity and/or organ prolapse,
[13] a method of activating serotonin 5-HT$_{2C}$ receptor, which comprises administering an effective amount of the compound or salt of the above-mentioned [1] or [2] to a mammal,
[14] a method for the prophylaxis or treatment of lower urinary tract symptom, obesity and/or organ prolapse, which comprises administering an effective amount of the compound or salt of the above-mentioned [1] or [2] to a mammal,
[15] use of the compound or salt of the above-mentioned [1] or [2] for the production of an agent for the prophylaxis or treatment of lower urinary tract symptom, obesity and/or organ prolapse, and
[16] the compound or salt of the above-mentioned [1] or [2] for use in the prophylaxis or treatment of lower urinary tract symptom, obesity and/or organ prolapse.

Effect of the Invention

The present invention provides a compound having a superior serotonin 5-HT$_{2C}$ receptor activating action or a salt thereof, which is useful as a safe agent for treatment or the prophylaxis of all serotonin 5-HT$_{2C}$-related disease such as lower urinary tract symptom, obesity and/or organ prolapse and the like.

DETAILED DESCRIPTION OF THE INVENTION

The present invention is explained in detail in the following, which are not to be construed as limitative.
The "halogen atom" means a fluorine atom, a chlorine atom, a bromine atom or an iodine atom.
The "alkyl group" means a linear or branched alkyl group having 1 to 6 carbon atoms, and examples thereof include a methyl group, an ethyl group, a propyl group, an isopropyl group, a butyl group, an isobutyl group, a sec-butyl group, a tert-butyl group, a 1-methylpropyl group, a pentyl group, an isopentyl group, a 1,2-dimethylpropyl group, a hexyl group, a 2-methylpentyl group, a 3-methylpentyl group, a 1,2-dimethylbutyl group and a 1,2,2-trimethylpropyl group.
The "alkoxy group" means a linear or branched alkoxy group having 1 to 6 carbon atoms, and examples thereof include a methoxy group, an ethoxy group, a propoxy group, an isopropoxy group, a butoxy group, an isobutoxy group, a sec-butoxy group, a tert-butoxy group, a pentoxy group, an isopentoxy group and a hexoxy group.
The "cycloalkyl group" means a cyclic alkyl group having 3 to 6 carbon atoms, and examples thereof include a cyclopropyl group, a cyclobutyl group, a cyclopentyl group and a cyclohexyl group.
The "aryl group" means a mono-cyclic or fused polycyclic aromatic hydrocarbon group having 6 to 14 carbon atoms, and examples thereof include a phenyl group, a naphthyl group, a 2-naphthyl, 1-anthryl, 2-anthryl and 9-anthryl.
The "alkylcarbonyl group" means a group consisting of the above-mentioned "alkyl group" and a carbonyl group, and examples thereof include an acetyl group, a propionyl group and an isobutyryl group.
The "alkoxycarbonyl group" means a group consisting of the above-mentioned "alkoxy group" and a carbonyl group, and examples thereof include a methoxycarbonyl group, an ethoxycarbonyl group, an isopropoxycarbonyl group, a tert-butoxycarbonyl group, propoxycarbonyl, butoxycarbonyl, isobutoxycarbonyl, sec-butoxycarbonyl, pentyloxycarbonyl and hexyloxycarbonyl.
The "arylcarbonyl group" means a group consisting of the above-mentioned "aryl group" and a carbonyl group, and examples thereof include a benzoyl group, a 1-naphthylcarbonyl group and a 2-naphthylcarbonyl group.
The "alkylsulfonyl group" means a group consisting of the above-mentioned "alkyl group" and a sulfonyl group, and examples thereof include a methylsulfonyl group, an ethylsulfonyl group and an isopropylsulfonyl group.

The "alkylsulfinyl group" means a group consisting of the above-mentioned "alkyl group" and a sulfinyl group, and examples thereof include a methylsulfinyl group, an ethylsulfinyl group, an isopropylsulfinyl group, a propylsulfonyl, a butylsulfonyl, a sec-butylsulfonyl and a tert-butylsulfonyl.

The "N-alkylamino group" means a group wherein one or more hydrogen atoms of an amino group is substituted by the above-mentioned "alkyl group", and examples thereof include a methylamino group, a dimethylamino group, an ethylamino group, a diethylamino group, an isopropylamino group and a n-propylamino group.

The "aromatic carbocycle" means a mono-cyclic or fused poly-cyclic aromatic hydrocarbon group having 6 to 12 carbon atoms, and examples thereof include a benzene ring and a naphthalene ring.

The "aromatic heterocycle" means a 5- to 8-membered (mono-cyclic, di-cyclic or tri-cyclic) heterocycle showing aromaticity and containing, besides carbon atoms, one or three kinds of 1 to 5 hetero atoms selected from an oxygen atom, a nitrogen atom and a sulfur atom, and examples thereof include a pyridine ring, a pyrimidine ring, a pyridazine ring, a thiophene ring, a benzothiophene ring, a furan ring and a benzofuran ring.

The "alkenyl group" means a linear or branched alkenyl group having 2 to 6 carbon atoms, and examples thereof include a vinyl group, an isopropenyl group, a 1-propenyl group, a 2-methyl-1-propenyl group and a 1,2-dimethyl-1-propenyl group.

The "cycloalkenyl group" means a cyclic alkenyl group having 3 to 6 carbon atoms, and examples thereof include a cyclopropenyl group, a cyclobutenyl group, a cyclopentenyl group and a cyclohexenyl group.

The "$C_{1-6}$ alkyl group" means as defined in the above-mentioned "alkyl group".

Examples of the "optionally halogenated $C_{1-6}$ alkyl group" include a $C_{1-6}$ alkyl group optionally having 1 to 7, preferably 1 to 5 halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neo-pentyl, 5,5,5-trifluoropentyl, hexyl and 6,6,6-trifluorohexyl.

Examples of the $C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

Examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

Examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

Examples of the "optionally halogenated $C_{3-10}$ cycloalkyl group" include a $C_{3-10}$ cycloalkyl group optionally having 1 to 7, preferably 1 to 5 halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

Examples of the "$C_{3-10}$ cycloalkenyl group" include cyclopropenyl, cyclobutenyl, cyclopentenyl, cyclohexenyl, cycloheptenyl and cyclooctenyl.

The "$C_{6-14}$ aryl group" means as defined in the above-mentioned "aryl group".

Examples of the "$C_{7-16}$ aralkyl group" include benzyl, phenethyl, naphthyl methyl and phenylpropyl.

The "$C_{1-6}$ alkoxy group" means as defined in the above-mentioned "alkoxy group".

Examples of the "optionally halogenated $C_{1-6}$ alkoxy group" include a $C_{1-6}$ alkoxy group optionally having 1 to 7, preferably 1 to 5 halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

Examples of the "$C_{3-10}$ cycloalkyloxy group" include cyclopropyloxy, cyclobutyloxy, cyclopentyloxy, cyclohexyloxy, cycloheptyloxy and cyclooctyloxy.

Examples of the "$C_{1-6}$ alkylthio group" include methylthio, ethylthio, propylthio, isopropylthio, butylthio, sec-butylthio, tert-butylthio, pentylthio and hexylthio.

Examples of the "optionally halogenated $C_{1-6}$ alkylthio group" include a $C_{1-6}$ alkylthio group optionally having 1 to 7, preferably 1 to 5 halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

Examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

Examples of the "optionally halogenated $C_{1-6}$ alkyl-carbonyl group" include a $C_{1-6}$ alkyl-carbonyl group optionally having 1 to 7, preferably 1 to 5 halogen atoms. Specific examples thereof include acetyl, chloroacetyl, trifluoroacetyl, trichloroacetyl, propanoyl, butanoyl, pentanoyl and hexanoyl.

The "$C_{1-6}$ alkoxy-carbonyl group" means as defined in the above-mentioned "alkoxycarbonyl group".

Examples of the "$C_{6-14}$ aryl-carbonyl group" include benzoyl, 1-naphthoyl and 2-naphthoyl.

Examples of the "$C_{7-16}$ aralkyl-carbonyl group" include phenylacetyl and phenylpropionyl.

Examples of the "5- to 14-membered aromatic heterocyclylcarbonyl group" include nicotinoyl, isonicotinoyl, thenoyl and furoyl.

Examples of the "3- to 14-membered non-aromatic heterocyclylcarbonyl group" include morpholinylcarbonyl, piperidinylcarbonyl and pyrrolidinylcarbonyl.

Examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

Examples of the "mono- or di-$C_{7-16}$ aralkyl-carbamoyl group" include benzylcarbamoyl and phenethylcarbamoyl.

The "$C_{1-6}$ alkylsulfonyl group" means as in defined the above-mentioned "alkylsulfonyl group".

Examples of the "optionally halogenated $C_{1-6}$ alkylsulfonyl group" include a $C_{1-6}$ alkylsulfonyl group optionally having 1 to 7, preferably 1 to 5 halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

Examples of the "$C_{6-14}$ arylsulfonyl group" include phenylsulfonyl, 1-naphthylsulfonyl and 2-naphthylsulfonyl.

Examples of the "5- to 14-membered aromatic heterocyclic group" include a 5- to 14-membered (preferably 5- to 10-membered) aromatic heterocyclic group containing, as a ring-constituting atom besides carbon atoms, 1 to 4 hetero atoms selected from a nitrogen atom, a sulfur atom and an oxygen atom.

Preferable examples the "5- to 14-membered aromatic heterocyclic group" include 5- to 6-membered mono-cyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused poly-cyclic (preferably di- or tri-cyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

Examples of the "3- to 14-membered non-aromatic heterocyclic group" include a 3- to 14-membered (preferably 4- to 10-membered) non-aromatic heterocyclic group containing, as a ring-constituting atom besides carbon atoms, 1 to 4 hetero atoms selected from a nitrogen atom, a sulfur atom and an oxygen atom.

Preferable examples the "3- to 14-membered non-aromatic heterocyclic group" include 3- to 8-membered mono-cyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused poly-cyclic (preferably di- or tri-cyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl and the like.

The "alkyl group optionally having substituent(s)" means the above-mentioned "alkyl group" which is substituted or unsubstituted, and examples of the substituent include 1 to 3 selected from (1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by $C_{1-6}$ alkyl group(s) (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ aryl sulfinyl group (e.g., phenylsulfinyl, 1-naphthyl sulfinyl, 2-naphthyl sulfinyl),
(43) a 5- to 14-membered aromatic heterocyclylsulfinyl group (e.g., pyridyl sulfinyl, thienylsulfinyl),
(44) an amino group,

(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ aryl amino group (e.g., phenylamino),
(47) a 5- to 14-membered aromatic heterocyclylamino group (e.g., pyridyl amino),
(48) a $C_{7-16}$ aralkylamino group (e.g., benzyl amino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., 5 methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by $C_{1-6}$ alkyl group(s) (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group,
and they are the same or different.

The substituents are preferably 1 to 3 selected from
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{1-6}$ alkyl-carbonyloxy group (e.g., acetoxy, propanoyloxy),
(9) a $C_{1-6}$ alkoxy-carbonyloxy group (e.g., methoxycarbonyloxy, ethoxycarbonyloxy, propoxycarbonyloxy, butoxycarbonyloxy),
(10) a 3- to 14-membered non-aromatic heterocyclylcarbonyloxy group (e.g., morpholinylcarbonyloxy, piperidinylcarbonyloxy),
(11) a formyl group,
(12) a carboxy group,
(13) a carbamoyl group,
(14) an amino group,
(15) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(16) a mono- or di-$C_{6-14}$ aryl amino group (e.g., phenylamino),
(17) a 5- to 14-membered aromatic heterocyclylamino group m (e.g., pyridyl amino),
(18) a $C_{7-16}$ aralkylamino group (e.g., benzyl amino),
(19) a $C_{3-10}$ cycloalkenyl group, and
(20) a $C_{6-14}$ aryl group, and they are the same or different, more preferably 1 to 3 selected from
(1) a halogen atom,
(2) a cyano group,
(3) a hydroxy group,
(4) a nitro group,
(5) a formyl group,
(6) an amino group, and
(7) a phenyl group, and they are the same or different.

The number of the substituent is preferably 1 or 2, more preferably 1.

The "alkoxy group optionally having substituent(s)" means the above-mentioned "alkoxy group" which is substituted or unsubstituted, and the examples of the substituent and the number thereof include substituents and the number thereof that the "alkyl group optionally having substituent(s)" optionally has. The number of the substituent is preferably 1 or 2, more preferably 1.

The "cycloalkyl group optionally having substituent(s)" means the above-mentioned "cycloalkyl group" which is substituted or unsubstituted, and the examples of the substituent and the number thereof include substituents and the number thereof that the "alkyl group optionally having substituent(s)" optionally has. The number of the substituent is preferably 1 or 2, more preferably 1.

The "aryl group optionally having substituent(s)" means the above-mentioned "aryl group" which is substituted or unsubstituted, and the examples of the substituent and the number thereof include substituents and the number thereof that the "alkyl group optionally having substituent(s)" optionally has. The number of the substituent is preferably 1 or 2, more preferably 1.

The "alkylcarbonyl group optionally having substituent(s)" means the above-mentioned "alkylcarbonyl group" which is substituted or unsubstituted, and the examples of the substituent and the number thereof include substituents and the number thereof that the "alkyl group optionally having substituent(s)" optionally has. The number of the substituent is preferably 1 or 2, more preferably 1.

The "alkoxycarbonyl group optionally having substituent(s)" means the above-mentioned "alkoxycarbonyl group" which is substituted or unsubstituted, and the examples of the substituent and the number thereof include substituents and the number thereof that the "alkyl group optionally having substituent(s)" optionally has. The number of the substituent is preferably 1 or 2, more preferably 1.

The "arylcarbonyl group optionally having substituent(s)" means the above-mentioned "arylcarbonyl group" which is substituted or unsubstituted, and the examples of the substituent and the number thereof include substituents and the number thereof that the "alkyl group optionally having substituent(s)" optionally has. The number of the substituent is preferably 1 or 2, more preferably 1.

The "alkylsulfonyl group optionally having substituent(s)" means the above-mentioned "alkylsulfonyl group" which is substituted or unsubstituted, and the examples of the substituent and the number thereof include substituents and the number thereof that the "alkyl group optionally having substituent(s)" optionally has. The number of the substituent is preferably 1 or 2, more preferably 1.

The "alkylsulfinyl group optionally having substituent(s)" means the above-mentioned "alkylsulfinyl group" which is substituted or unsubstituted, and the examples of the substituent and the number thereof include substituents and the number thereof that the "alkyl group optionally having substituent(s)" optionally has. The number of the substituent is preferably 1 or 2, more preferably 1.

The "aromatic carbocycle optionally having substituent(s)" means the above-mentioned "aromatic carbocycle" which is substituted or unsubstituted, and the examples of the substituent and the number thereof include substituents and the number thereof that the "alkyl group optionally having substituent(s)" optionally has. The number of the substituent is preferably 1 or 2, more preferably 1.

The "aromatic heterocycle optionally having substituent(s)" means the above-mentioned "aromatic heterocycle" which is substituted or unsubstituted, and the examples of the substituent and the number thereof include substituents and the number thereof that the "alkyl group optionally having substituent(s)" optionally has. The number of the substituent is preferably 1 or 2, more preferably 1.

Ring A is preferably a benzene ring, a pyridine ring, a pyrimidine ring, a thiophene ring or a furan ring, more preferably a benzene ring, a pyridine ring or a thiophene ring, more preferably a benzene ring.

X is preferably —N($R^1$)—, S or O, more preferably —N($R^1$)—.

When ring A is an aromatic carbocycle optionally having substituent(s), then the preferable examples of the substituent for the aromatic carbocycle include a halogen atom and an alkyl group optionally having substituent(s), and more preferable examples thereof include a halogen atom and an alkyl group.

When ring A is an aromatic heterocycle optionally having substituent(s), then the preferable examples of the substituent for the aromatic heterocycle include a halogen atom and an alkyl group optionally having substituent(s), and more preferable examples thereof include a halogen atom and an alkyl group.

When ring A is an aromatic carbocycle optionally having substituent(s), then $R^1$ is preferably a hydrogen atom, an alkyl group optionally having substituent(s), an alkoxycarbonyl group optionally having substituent(s) or an alkylcarbonyl group optionally having substituent(s), preferably an alkyl group optionally having 1 to 3 substituent(s) selected from a halogen atom, a cyano group, a hydroxy group, a nitro group, a formyl group, an amino group and a phenyl group, or an alkylcarbonyl group optionally having 1 to 3 substituent(s) selected from a halogen atom, a cyano group, a hydroxy group, a nitro group, a formyl group, an amino group and a phenyl group, more preferably a $C_1$-$C_3$ alkyl group optionally having 1 to 3 substituent(s) selected from a cyano group, a hydroxy group and a phenyl group, still more preferably a methyl group or an isopropyl group.

When ring A is an aromatic heterocycle optionally having substituent(s), then $R^1$ is preferably a hydrogen atom, an alkyl group optionally having substituent(s), an alkoxycarbonyl group optionally having substituent(s) or an alkylcarbonyl group optionally having substituent(s), preferably an alkyl group optionally having 1 to 3 substituent(s) selected from a halogen atom, a cyano group, a hydroxy group, a nitro group, a formyl group, an amino group and a phenyl group, or an alkylcarbonyl group optionally having 1 to 3 substituent(s) selected from a halogen atom, a cyano group, a hydroxy group, a nitro group, a formyl group, an amino group and a phenyl group, more preferably a $C_1$-$C_3$ alkyl group optionally having 1 to 3 substituent(s) selected from a cyano group, a hydroxy group and a phenyl group, still more preferably a methyl group or an isopropyl group.

$R^2$ is preferably a hydrogen atom, a halogen atom, or an alkyl group optionally having 1 to 3 substituent(s) selected from a halogen atom, a cyano group, a hydroxy group, a nitro group, a formyl group, an amino group and a phenyl group, more preferably a halogen atom, or an alkyl group optionally having 1 to 3 substituent(s) selected from a cyano group, a hydroxy group and a phenyl group, still more preferably a chlorine atom.

n is 0, 1 or 2, preferably 0 or 1, more preferably 0. m is 1, 2 or 3, preferably 1 or 2, more preferably 1.

$Y_1$, $Y_2$ and $Y_3$ are all carbon atoms, or any one of $Y_1$, $Y_2$ and $Y_3$ is a nitrogen atom, the other two are carbon atoms, preferably $Y_1$, $Y_2$ and $Y_3$ are all carbon atoms.

Preferable examples of Compound (1), which is one embodiment of the compound of the present invention, include the following compound.

[Compound (1-1)]

In compound (1), a compound wherein

Ring A is a benzene ring substituted by a halogen atom or an alkyl group,

X is —N($R^1$)—, $R^1$ is a hydrogen atom, an alkyl group optionally having substituent(s), a cycloalkyl group, an alkylcarbonyl group, an arylcarbonyl group optionally having substituent(s), an alkoxycarbonyl group, an alkylsulfonyl group or an alkylsulfinyl group,

------ is a single bond or a double bond, $Y_1$, $Y_2$ and $Y_3$ are all carbon atoms, $R^2$ are the same or different and each is a hydrogen atom, a halogen atom or an alkyl group, m is an integer of 1 or 2, and n is 0, or a salt thereof.

Preferable examples of Compound (2), which is one embodiment of the compound of the present invention, include the following compound.

[Compound (2-1)]

In compound (2), a compound wherein

X is —N($R^1$)—, $R^1$ is a hydrogen atom, an alkyl group optionally having substituent(s), a cycloalkyl group, an alkylcarbonyl group, an arylcarbonyl group optionally having substituent(s), an alkoxycarbonyl group, an alkylsulfonyl group or an alkylsulfinyl group,

------ is a single bond or a double bond, $Y_1$, $Y_2$ and $Y_3$ are all carbon atoms, $R^2$ are the same or different and each is a hydrogen atom, a halogen atom or an alkyl group, m is an integer of 1 or 2, and n is 0, or a salt thereof.

It is preferably a compound wherein

X is —N($R^1$)—, $R^1$ is a hydrogen atom, an alkyl group optionally having phenyl group(s), a cycloalkyl group, an alkylcarbonyl group having 1 to 3 carbon atoms, a methoxycarbonyl group or a methylsulfonyl group,

------ is a single bond or a double bond, $Y_1$, $Y_2$ and $Y_3$ are all carbon atoms, $R^2$ are the same or different and each is a hydrogen atom, a chlorine atom, a bromine atom, or an alkyl group having 1 to 3 carbon atoms and optionally having phenyl group(s), m is an integer of 1 or 2, and n is 0, or a salt thereof.

It is more preferably a compound wherein

X is —N($R^1$)—, $R^1$ is a hydrogen atom, an alkyl group having 1 to 3 carbon atoms and optionally having phenyl group(s), a cycloalkyl group, or an alkylcarbonyl group having 1 to 3 carbon atoms,

------ is a single bond, $Y_1$, $Y_2$ and $Y_3$ are all carbon atoms, $R^2$ are the same or different and each is a chlorine atom, or an alkyl group having 1 to 3 carbon atoms, m is 1, and n is 0, or a salt thereof.

Other preferable examples of Compound (2), which is one embodiment of the compound of the present invention, include the following compound.

[Compound (2-2)]

In compound (2), a compound wherein

X is —O—, —S—, —S(O)$_2$— or —S(O)—,

------ is a single bond or a double bond, $Y_1$, $Y_2$ and $Y_3$ are all carbon atoms, $R^2$ are the same or different and each is a hydrogen atom, a halogen atom or an alkyl group, m is an integer of 1 or 2, and n is 0, or a salt thereof.

It is preferably a compound wherein

X is —O—, —S— or —S(O)$_2$—,

------ is a single bond or a double bond, $Y_1$, $Y_2$ and $Y_3$ are all carbon atoms, $R^2$ are the same or different and each is a hydrogen atom or a chlorine atom, m is an integer of 1 or 2, and n is 0, or a salt thereof.

Other preferable examples of Compound (2), which is one embodiment of the compound of the present invention, include the following compound.

[Compound (2-3)]

In compound (2), a compound wherein

X is —N($R^1$)—, $R^1$ is a hydrogen atom, an alkyl group optionally having substituent(s), a cycloalkyl group optionally having substituent(s), an alkylcarbonyl group optionally having substituent(s), an arylcarbonyl group optionally having substituent(s), an alkoxycarbonyl group optionally having substituent(s), an alkylsulfonyl group optionally having substituent(s) or an alkylsulfinyl group optionally having substituent(s),

------ is a single bond or a double bond, $Y_1$, $Y_2$ and $Y_3$ are all carbon atoms, $R^2$ are the same or different and each is a halogen atom, or an alkyl group optionally having substituent(s), m is an integer of 1, 2 or 3, and n is 0, or a salt thereof.

It is preferably a compound wherein

X is —N($R^1$)—, $R^1$ is (1) a hydrogen atom, (2) an alkyl group optionally having 1 to 3 substituent(s) selected from a halogen atom, a cyano group, a hydroxy group, a nitro group, a formyl group, an amino group and a phenyl group, (3) a cycloalkyl group optionally having 1 to 3 substituent(s) selected from a halogen atom, a cyano group, a hydroxy group, a nitro group, a formyl group, an amino group and a phenyl group, (4) an alkylcarbonyl group optionally having 1 to 3 substituent(s) selected from a halogen atom, a cyano group, a hydroxy group, a nitro group, a formyl group, an amino group and a phenyl group, (5) an arylcarbonyl group optionally having 1 to 3 substituent(s) selected from a halogen atom, a cyano group, a hydroxy group, a nitro group, a formyl group, an amino group and a phenyl group, (6) an alkoxycarbonyl group optionally having 1 to 3 substituent(s) selected from a halogen atom, a cyano group, a hydroxy group, a nitro group, a formyl group, an amino group and a phenyl group, (7) an alkylsulfonyl group optionally having 1 to 3 substituent(s) selected from a halogen atom, a cyano group, a hydroxy group, a nitro group, a formyl group, an amino group and a phenyl group, or (8) an alkylsulfinyl group optionally having 1 to 3 substituent(s) selected from a halogen atom, a cyano group, a hydroxy group, a nitro group, a formyl group, an amino group and a phenyl group,

------ is a single bond or a double bond, $Y_1$, $Y_2$ and $Y_3$ are all carbon atoms, $R^2$ are the same or different and each is a halogen atom, or an alkyl group optionally having 1 to 3 substituent(s) selected from a halogen atom, a cyano group, a hydroxy group, a nitro group, a formyl group, an amino group and a phenyl group, m is an integer of 1, 2 or 3, and n is 0, or a salt thereof, more preferably a compound wherein X is —N($R^1$)—, $R^1$ is (1) a hydrogen atom, (2) an alkyl group optionally having 1 to 3 substituent(s) selected from a cyano group, a hydroxy group and a phenyl group, (3) a cycloalkyl group optionally having 1 to 3 substituent(s) selected from a cyano group, a hydroxy group and a phenyl group, (4) an alkylcarbonyl group optionally having 1 to 3 substituent(s) selected from a cyano group, a hydroxy group and a phenyl group, (5) an arylcarbonyl group optionally having 1 to 3 substituent(s) selected from a cyano group, a hydroxy group and a phenyl group, (6) an alkoxycarbonyl group optionally having 1 to 3 substituent(s) selected from a cyano group, a hydroxy group and a phenyl group, (7) an alkylsulfonyl group optionally having 1 to 3 substituent(s) selected from a cyano group, a hydroxy group and a phenyl group m, or (8) an alkylsulfinyl group optionally having 1 to 3 substituent(s) selected from a cyano group, a hydroxy group and a phenyl group, ------ is a single bond or a double bond, $Y_1$, $Y_2$ and $Y_3$ are all carbon atoms, $R^2$ are the same or different and each is a halogen atom, or an alkyl group optionally having 1 to 3 substituent(s) selected from a cyano group, a hydroxy group and a phenyl group, m is an integer of 1, 2 or 3, and n is 0, or a salt thereof.

Other preferable examples of Compound (2), which is one embodiment of the compound of the present invention, include the following compound.

[Compound (2-4)]

In compound (2), a compound wherein

X is —N($R^1$)—, $R^1$ is a hydrogen atom, an alkyl group optionally having substituent(s), a cycloalkyl group optionally having substituent(s), an alkylcarbonyl group optionally having substituent(s), an arylcarbonyl group optionally having substituent(s), an alkoxycarbonyl group optionally having substituent(s) or an alkylsulfonyl group optionally having substituent(s), ------ is a single bond or a double bond, $Y_1$, $Y_2$ and $Y_3$ are all carbon atoms, $R^2$ are the same or different and each is a halogen atom, or an alkyl group optionally having substituent(s), m is an integer of 1, 2 or 3, and n is 0, or a salt thereof.

It is preferably a compound wherein

X is —N($R^1$)—, $R^1$ is (1) a hydrogen atom, (2) an alkyl group optionally having 1 to 3 substituent(s) selected from a halogen atom, a cyano group, a hydroxy group, a nitro group, a formyl group, an amino group and a phenyl group, (3) a cycloalkyl group optionally having 1 to 3 substituent(s) selected from a halogen atom, a cyano group, a hydroxy group, a nitro group, a formyl group, an amino group and a phenyl group, (4) an alkylcarbonyl group optionally having 1 to 3 substituent(s) selected from a halogen atom, a cyano group, a hydroxy group, a nitro group, a formyl group, an amino group and a phenyl group, (5) an arylcarbonyl group optionally having 1 to 3 substituent(s) selected from a halogen atom, a cyano group, a hydroxy group, a nitro group, a formyl group, an amino group and a phenyl group, (6) an alkoxycarbonyl group optionally having 1 to 3 substituent(s) selected from a halogen atom, a cyano group, a hydroxy group, a nitro group, a formyl group, an amino group and a phenyl group, or (7) an alkylsulfonyl group optionally having 1 to 3 substituent(s) selected from a halogen atom, a cyano group, a hydroxy group, a nitro group, a formyl group, an amino group and a phenyl group, ------ is a single bond or a double bond, $Y_1$, $Y_2$ and $Y_3$ are all carbon atoms, $R^2$ are the same or different and each is a halogen atom, or an alkyl group optionally having 1 to 3 substituent(s) selected from a halogen atom, a cyano group, a hydroxy group, a nitro group, a formyl group, an amino group and a phenyl group, m is an integer of 1, 2 or 3, and n is 0, or a salt thereof, more preferably a compound wherein X is —N($R^1$)—, $R^1$ is (1) a hydrogen atom, (2) an alkyl group optionally having 1 to 3 substituent(s) selected from a cyano group, a hydroxy group and a phenyl group, (3) a cycloalkyl group optionally having 1 to 3 substituent(s) selected from a cyano group, a hydroxy group and a phenyl group, (4) an alkylcarbonyl group optionally having 1 to 3 substituent(s) selected from a cyano group, a hydroxy group and a phenyl group, (5) an arylcarbonyl group optionally having 1 to 3 substituent(s) selected from a cyano group, a hydroxy group and a phenyl group, (6) an alkoxycarbonyl group optionally having 1 to 3 substituent(s) selected from a cyano group, a hydroxy group and a phenyl group, or (7) an alkylsulfonyl group optionally having 1 to 3 substituent(s) selected from a cyano group, a hydroxy group and a phenyl group, ------ is a single bond or a double bond, $Y_1$, $Y_2$ and $Y_3$ are all carbon atoms, $R^2$ are the same or different and each is a halogen atom, or an alkyl group optionally having 1 to 3 substituent(s) selected from a cyano group, a hydroxy group and a phenyl group, m is an integer of 1, 2 or 3, and n is 0, or a salt thereof.

Specific preferable examples of the compound of the present invention include the following compounds.

(2a5)-9-chloro-1-isopropyl-2,2a,3,4,5,6-hexahydro-1H-azepino[3,4,5-cd]indole, or a salt thereof.

9-chloro-2,2a,3,4,5,6-hexahydro-1H-azepino[3,4,5-cd]indole, or a salt thereof.

9-isopropyl-1-methyl-2,2a,3,4,5,6-hexahydro-1H-azepino[3,4,5-cd]indole, or a salt thereof.

(2aS)-9-chloro-1-methyl-2,2a,3,4,5,6-hexahydro-1H-azepino[3,4,5-cd]indole, or a salt thereof.

More preferable examples thereof include the following compounds.

(2aS)-9-chloro-1-isopropyl-2,2a,3,4,5,6-hexahydro-1H-azepino[3,4,5-cd]indole, or a salt thereof.

9-chloro-2,2a,3,4,5,6-hexahydro-1H-azepino[3,4,5-cd]indole, or a salt thereof.

9-isopropyl-1-methyl-2,2a,3,4,5,6-hexahydro-1H-azepino[3,4,5-cd]indole, or a salt thereof.

Hereinafter, compounds (1) and (2), which are the compounds of the present invention, are collectively described as "the compound of the present invention".

The compound of the present invention may be a pharmaceutically acceptable salt, and examples thereof include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexyl amine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among them, a pharmaceutically acceptable salt is preferable.

The compound of the present invention may be a solvate, (e.g., a hydrate) or a non-solvate (containing a non-hydrate).

When the compound of the present invention is in a form of a salt, a hydrate or/and a solvate, they are encompassed in the compound of the present invention.

The compound of the present invention may be labeled with a isotope (e.g., $^3H$, $^{11}C$, $^{14}C$, $^{18}F$, $^{35}S$, $^{125}I$) and the like, or a deuterium conversion form wherein $^1H$ is converted to $^2H(D)$. They are encompassed in the compound of the present invention.

The production methods of the compound of the present invention are explained below.

The compound of the present invention can be produced, for example, according to the following Method A-Method L, or a method analogous thereto.

Alternatively, the compound of the present invention can be produced by the combination of synthetic methods known per se.

The material compound and the compound obtained in each step may be in a form of a salt or a solvate. Examples of the salt and solvate of the material compound and the compound obtained in each step include those similar to the above-mentioned salts and solvates, and the like.

The compound obtained in each step can be used directly as the reaction mixture or as a crude product for the next reaction. The compound can also be isolated from a reaction mixture by conventional methods, and can be isolated and purified by conventional separation and purification means, concentration, concentration under reduced pressure, solvent extraction, crystallization, recrystallization, phase transfer, chromatography and the like.

The solvent used in each step is not particularly limited as long as it is solvent that does not adversely influence the reaction. Unless otherwise specified, examples of the selection of the solvent that does not adversely influence the reaction include Group A (alcohols (methanol, ethanol, isopropanol and the like), ethers (diethyl ether, tetrahydrofuran, 1,4-dioxane, tert-butyl methyl ether, 1,2-dimethoxyethane and the like), halogenated hydrocarbons (chloroform, dichloromethane, 1,2-dichloroethane and the like), aromatic hydrocarbons (benzene, toluene, chlorobenzene, nitrobenzene and the like), aliphatic hydrocarbons (hexane, heptane, cyclohexane, nitromethane and the like), amides (N,N-dimethylformamide, N,N-dimethylacetamide and the like), sulfoxides (dimethyl sulfoxide and the like), nitriles (acetonitrile and the like), esters (methyl acetate, ethyl acetate, butyl acetate and the like), carboxylic acids (acetic acid, trifluoroacetic acid and the like), water and the like. These solvents are used in a combination of two or more at a suitable ratio), or, Group B (alcohols (methanol, ethanol, isopropanol and the like), ethers (diethyl ether, tetrahydrofuran, 1,4-dioxane, tert-butyl methyl ether, 1,2-dimethoxyethane and the like), halogenated hydrocarbons (chloroform, dichloromethane, 1,2-dichloroethane and the like), aromatic hydrocarbons (benzene, toluene, chlorobenzene, nitrobenzene and the like), aliphatic hydrocarbons (hexane, heptane, cyclohexane, nitromethane and the like), amides (N,N-dimethylformamide, N,N-dimethylacetamide and the like), sulfoxides (dimethyl sulfoxide and the like), nitriles (acetonitrile and the like), esters (methyl acetate, ethyl acetate, butyl acetate and the like) and the like. These solvents are used in a combination of two or more at a suitable ratio).

[Method A]

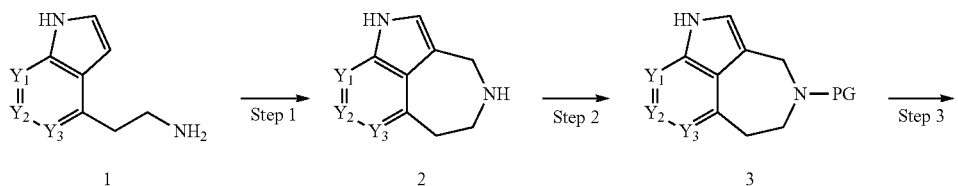

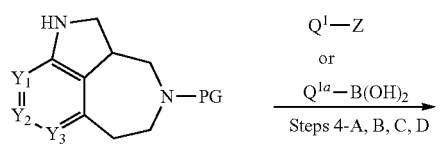

4

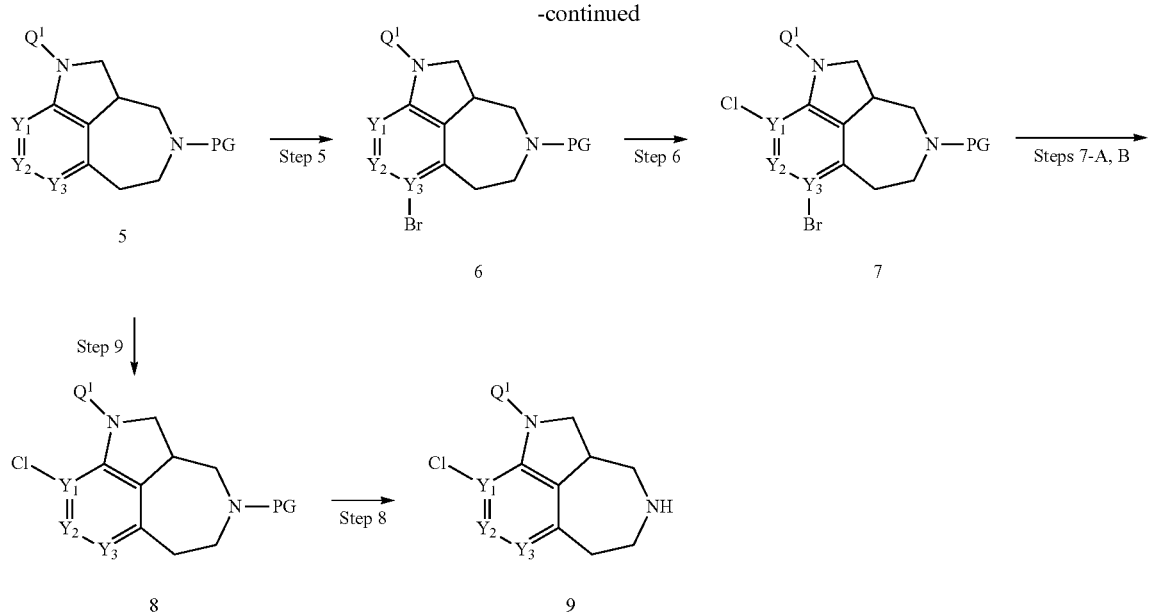

wherein PG is a protecting group, $Q^1$ is an alkyl group optionally having substituent(s), a cycloalkyl group optionally having substituent(s), an alkenyl group optionally having substituent(s), an cycloalkenyl group optionally having substituent(s), an alkylcarbonyl group optionally having substituent(s) or an alkoxycarbonyl group optionally having substituent(s), and examples of the substituent referred herein include groups that does not adversely influence the reaction. Z of $Q^1$-Z is a leaving group (e.g., a chloro group, a bromo group, an iodo group, a p-toluenesulfonyloxy group). $Y_1$, $Y_2$ and $Y_3$ are as defined above, and $Y_1$, $Y_2$ and $Y_3$ are all carbon atoms, or any one of $Y_1$, $Y_2$ and $Y_3$ is a nitrogen atom, and the other two are carbon atoms.

Examples of the "protecting group" for PG include amino-protecting groups (tert-butoxycarbonyl group, a methoxycarbonyl group, acetyl group and the like) that is generally used for peptide synthesis and the like and that does not adversely influence the reaction in each step, and a tert-butoxycarbonyl group is preferable.

Step 1

This step is a step of subjecting Compound 1 to a Pictet-Spengler reaction to produce Compound 2. This reaction can be carried out according to methods known per se (the method described in Jikken Kagaku Kouza, 3rd edition, vol. 14, page 2012, the method described in Chemical Reviews, 1995, vol. 95, page 1797, and the like), generally in the presence of an acid and a formylating agent, where necessary in a solvent that does not adversely influence the reaction. Compound 1 can be produced according to methods known per se (the method described in Bioorganic and Medicinal Chemistry Letters, 1988, vol. 8, page 983, and the like) or a method analogous thereto.

Examples of the acid include hydrochloric acid, hydrobromic acid, sulfuric acid, trifluoroacetic acid, trifluoromethanesulfonic acid, hydrogen chloride, tosyl acid and the like. Among them, hydrochloric acid is preferable.

The amount of the acid to be used is generally about 0.01 mol-solvent amount, preferably about 1 mol-solvent amount, per 1 mol of Compound 1.

Examples of the formylating agent include formaldehyde, aqueous formalin, dichloromethyl methyl ether, N,N-dimethylformamide dimethyl acetal and the like. Among them, aqueous formalin is preferable.

The amount of the formylating agent to be used is generally about 1 mol-10 mol, preferably about 1 mol-5 mol, per 1 mol of Compound 1.

Examples of the solvent that does not adversely influence the reaction include the above-mentioned Group A.

The reaction temperature is generally about –80° C.-about 200° C., preferably about –80° C.-about 100° C.

The reaction time is generally about 0.1 hr-about 200 hr, preferably about 0.5 hr-about 48 hr.

Step 2

This step is a step of introducing a protecting group into Compound 2 to produce Compound 3.

For example, when PG is a tert-butoxycarbonyl group, then the introduction of a protecting group is carried out according to methods known per se, for example, by subjecting Compound 2 to a tert-butoxycarbonylation reaction. The tert-butoxycarbonylation reaction is generally carried out using a tert-butoxycarbonylating agent (di-tert-butyl dicarbonate and the like), where necessary in the presence of a base and a catalyst, in a solvent that does not adversely influence the reaction.

Examples of the base used where necessary include organic amines (trimethylamine, triethylamine, diisopropylethylamine, N-methylmorpholine, 1,8-diazabicyclo[5,4,0]undec-7-ene, pyridine and the like), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like), alkali metal hydrides (potassium hydride, sodium hydride and the like) and the like. Among them, organic amines such as triethylamine and the like, and alkali metal salts such as sodium carbonate, potassium carbonate and the like are preferable.

The amount of the base to be used where necessary is generally about 0.1 mol-10 mol, preferably about 1 mol-about 5 mol, per 1 mol of Compound 2.

Examples of the solvent that does not adversely influence the reaction include the above-mentioned Group A.

Examples of the catalyst include 4-dimethylaminopyridine, 4-pyrrolidinopyridine and the like. Among them, 4-dimethylaminopyridine is preferable.

The amount of the catalyst to be used is generally 0.01 mol-1 mol, preferably about 0.1 mol-about 0.5 mol, per 1 mol of Compound 2.

The reaction temperature is generally about −80° C.-about 200° C., preferably about 0° C.-about 100° C.

The reaction time is generally about 0.1 hr-about 200 hr, preferably about 0.5 hr-about 48 hr.

Step 3

This step is a step of reducing the double bond of Compound 3 to produce Compound 4.

This reaction can be carried out according to methods known per se, generally in the presence of a reducing agent, where necessary in a solvent that does not adversely influence the reaction.

Examples of the reducing agent include aluminium reagents (lithium aluminium hydride, diisobutylaluminium hydride, sodium bis(2-methoxyethoxy)aluminium hydride, alane and the like), boron reagents (borane, 9-borabicyclo[3,3,1]nonane, sodium borohydride, sodium cyanoborohydride, sodium triacetoxyborohydride and the like) and the like. Among them, lithium aluminium hydride and sodium cyanoborohydride are preferable.

The amount of the reducing agent to be used is generally about 0.3 mol-about 10 mol, preferably about 1 mol-about 5 mol, per 1 mol of Compound 3.

Examples of the solvent that does not adversely influence the reaction include the above-mentioned Group A.

The reaction temperature is generally about −80° C.-about 200° C., preferably about −80° C.-about 100° C.

The reaction time is generally about 0.1 hr-about 100 hr, preferably about 0.5 hr-about 24 hr.

Step 4

This step is a step of modifying the amino group at the 1-position of Compound 4 to produce Compound 5.

Method 4-A

This step is a step of reacting Compound 4 with $Q^1$-Z in the presence of a base to produce Compound 5.

This reaction can be carried out according to methods known per se, generally in the presence of a base, where necessary in a solvent that does not adversely influence the reaction.

The amount of the $Q^1$-Z to be used is generally 1 mol-10 mol, preferably about 1 mol-about 2 mol, per 1 mol of Compound 4.

Examples of the base include organic amines (trimethylamine, triethylamine, diisopropylethylamine, N-methylmorpholine, 1,8-diazabicyclo[5,4,0]undec-7-ene, pyridine and the like), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like), alkali metal hydrides (potassium hydride, sodium hydride and the like), alkali metal alkoxides (sodium methoxide, sodium ethoxide and the like), organic lithium compounds (n-butyllithium, sec-butyllithium, tert-butyllithium and the like), alkali metal disilazides (lithium hexamethyldisilazide, sodium hexamethyldisilazide, potassium hexamethyldisilazide and the like), alkali metal amides (lithium diisopropylamide, lithium anilide, sodium bis(trimethylsilyl)amide, sodium amide and the like) and the like. Among them, alkali metal hydrides such as sodium hydride and the like, organic amines such as triethylamine and the like, and alkali metal salts such as potassium carbonate and the like are preferable.

The amount of the base to be used is generally about 1 mol-about 10 mol, preferably about 1 mol-about 5 mol, per 1 mol of Compound 4.

Examples of the solvent that does not adversely influence the reaction include the above-mentioned Group B.

The reaction temperature is generally about −50° C.-about 200° C., preferably about 0° C.-about 150° C.

The reaction time is generally about 0.1 hr-about 100 hr, preferably about 0.5 hr-about 24 hr.

Method 4-B

This step is a step of subjecting Compound 4 to a reductive alkylation reaction with a carbonyl compound (acetaldehyde, propionaldehyde, acetone and the like) to produce Compound 5.

This reaction can be carried out according to methods known per se (the method described in Jikken Kagaku Kouza, 3rd edition, vol. 14, page 1385, and the like), generally in the presence of a reducing agent, where necessary in a solvent that does not adversely influence the reaction.

The amount of the carbonyl compound to be used is generally about 1 mol-about 10 mol, preferably about 1 mol-about 5 mol, per 1 mol of Compound 4.

Examples of the reducing agent include aluminium reagents (lithium aluminium hydride, diisobutylaluminium hydride, sodium bis(2-methoxyethoxy)aluminium hydride, alane and the like), boron reagents (borane, 9-borabicyclo[3,3,1]nonane, sodium borohydride, sodium cyanoborohydride, sodium triacetoxyborohydride and the like) and the like. Among them, sodium borohydride, sodium cyanoborohydride and sodium triacetoxyborohydride are preferable.

The amount of the reducing agent to be used is generally about 1 mol-about 10 mol, preferably about 1 mol-about 5 mol, per 1 mol of Compound 4.

Examples of the solvent that does not adversely influence the reaction include the above-mentioned Group A.

The reaction temperature is generally about −80° C.-about 200° C., preferably about −80° C.-about 100° C.

The reaction time is generally about 0.1 hr-about 100 hr, preferably about 0.5 hr-about 24 hr.

Method 4-C

This step is a step of reacting Compound 4 with an acyl halide (acetyl chloride, benzoyl chloride and the like) or an anhydride (acetic anhydride, di-tert-butyl dicarbonate and the like) in the presence of a base to produce Compound 5. This reaction can be carried out according to methods known per se, generally in the presence of a base, where necessary in a solvent that does not adversely influence the reaction. Where necessary, a catalyst may be added.

The amount of the acyl halide or anhydride to be used is generally 1 mol-5 mol, preferably about 1 mol-about 2 mol, per 1 mol of Compound 4.

Examples of the base include organic amines (trimethylamine, triethylamine, diisopropylethylamine, N-methylmorpholine, 1,8-diazabicyclo[5,4,0]undec-7-ene, pyridine and the like), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like), alkali metal hydrides (potassium hydride, sodium hydride and the like), alkali metal alkoxides (sodium methoxide, sodium ethoxide and the like), organic lithium compounds (n-butyllithium, sec-butyllithium, tert-butyllithium and the like), alkali metal disilazides (lithium hexamethyldisilazide, sodium hexamethyldisilazide, potassium hexamethyldisilazide and the like), alkali metal amides (lithium diisopropylamide, lithium anilide, sodium bis(trimethylsilyl)amide, sodium amide and the like) and the like. Among them, organic amines such as triethylamine and the like, and alkali metal salts such as potassium carbonate and the like are preferable.

The amount of the base to be used is generally about 1 mol-about 10 mol, preferably about 1 mol-about 5 mol, per 1 mol of Compound 4.

Examples of the solvent that does not adversely influence the reaction include the above-mentioned Group B.

Examples of the catalyst include 4-dimethylaminopyridine, 4-pyrrolidinopyridine and the like. Among them, 4-dimethylaminopyridine is preferable.

The amount of the catalyst to be used is generally 0.01 mol-1 mol, preferably about 0.1 mol-about 0.5 mol, per 1 mol of Compound 4.

The reaction temperature is generally about −50° C.-about 200° C., preferably about 0° C.-about 150° C. The reaction time is generally about 0.1 hr-about 100 hr, preferably about 0.5 hr-about 24 hr.

Method 4-D

This step is a step of subjecting Compound 4 to a coupling reaction with a compound represented by the $Q^{1a}$-B(OH)$_2$ (wherein $Q^{1a}$ is an alkyl group optionally having substituent(s), a cycloalkyl group optionally having substituent(s), an alkenyl group optionally having substituent(s) or an cycloalkenyl group optionally having substituent(s), and examples of the substituent referred herein include groups that does not adversely influence the reaction, or a salt thereof, or a boronic acid ester (hereinafter sometimes to be abbreviated as $Q^{1a}$-B(OH)$_2$) to produce Compound 5.

This reaction can be carried out according to methods known per se (the method described in Chemical Communications, 2010, vol. 46, page 3393, the method described in Organic Letters, 2008, vol. 10, page 1653, and the like), for example, in the presence of a transition metal catalyst and a base, where necessary in a solvent that does not adversely influence the reaction. Where necessary, a ligand may be added.

The amount of the $Q^{1a}$-B(OH)$_2$ to be used is generally about 1 mol-about 10 mol, preferably about 1 mol-about 5 mol, per 1 mol of Compound 4.

Examples of the transition metal catalyst include copper catalysts (copper(II) acetate and the like) and the like.

The amount of the transition metal catalyst to be used is generally about 0.01 mol-about 10 mol, preferably about 0.1 mol-about 1 mol, per 1 mol of Compound 4.

Examples of the ligand used where necessary include pyridines (2,2'-bipyridyl, 2-hydroxypyridine and the like) and the like. Among them, 2,2'-bipyridyl is preferable.

The amount of ligand to be used is generally about 0.01 mol-about 10 mol, preferably about 0.1 mol-about 2 mol, per 1 mol of Compound 4.

Examples of the base include organic amines (trimethylamine, triethylamine, diisopropylethylamine, N-methylmorpholine, 1,8-diazabicyclo[5,4,0]undec-7-ene, pyridine and the like), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like), alkali metal hydrides (potassium hydride, sodium hydride and the like), alkali metal alkoxides (sodium methoxide, sodium ethoxide and the like), organic lithium compounds (n-butyllithium, sec-butyllithium, tert-butyllithium and the like), alkali metal disilazides (lithium hexamethyldisilazide, sodium hexamethyldisilazide, potassium hexamethyldisilazide and the like), alkali metal amides (lithium diisopropylamide, lithium anilide, sodium bis(trimethylsilyl)amide, sodium amide and the like) and the like. Among them, alkali metal salts such as sodium carbonate, potassium carbonate, cesium carbonate, sodium phosphate, potassium phosphate and the like, and alkali metal disilazides such as lithium hexamethyldisilazide, sodium hexamethyldisilazide and the like are preferable.

The amount of the base to be used is generally about 1 mol-about 10 mol, preferably about 1 mol-about 5 mol, per 1 mol of Compound 4.

Examples of the solvent that does not adversely influence the reaction include the above-mentioned Group A.

The reaction temperature is generally about −10° C.-about 200° C., preferably about 0° C.-about 150° C.

The reaction time is generally about 0.5 hr-about 48 hr, preferably about 0.5 hr-about 16 hr.

Step 5

This step is a step of subjecting Compound 5 to a bromination reaction to produce Compound 6. This step can be carried out according to methods known per se, generally by reacting Compound 5 with a brominating agent in a solvent that does not adversely influence the reaction.

Examples of the brominating agent include N-bromosuccinimide, bromine, pyridinium bromide perbromide, dibromoisocyanuric acid and the like. Among them, N-bromosuccinimide is preferable.

The amount of the brominating agent to be used is generally about 1 mol-about 100 mol, preferably about 1 mol -about 5 mol, per 1 mol of Compound 5.

Examples of the solvent that does not adversely influence the reaction include the above-mentioned Group A.

The reaction temperature is generally about −80° C.-about 200° C., preferably about −80° C.-about 100° C.

The reaction time is generally about 0.1 hr-about 100 hr, preferably about 0.5 hr-about 24 hr.

Step 6

This step is a step of subjecting Compound 6 to a chlorination reaction to produce Compound 7. This step can be carried out according to methods known per se, generally by m reacting Compound 6 with a chlorinating agent in a solvent that does not adversely influence the reaction.

Examples of the chlorinating agent include N-chlorosuccinimide, chlorine, trichloroisocyanuric acid, phosphorus (V) chloride and the like. Among them, N-chlorosuccinimide is preferable.

The amount of the chlorinating agent to be used is generally about 1 mol-about 100 mol, preferably about 1 mol -about 5 mol, per 1 mol of Compound 6.

Examples of the solvent that does not adversely influence the reaction include the above-mentioned Group A.

The reaction temperature is generally about −80° C.-about 200° C., preferably about −80° C.-about 100° C.

The reaction time is generally about 0.1 hr-about 100 hr, preferably about 0.5 hr-about 24 hr.

Step 7

This step is a step of removing the bromine atom from Compound 7 to produce Compound 8.

Method 7-A

This step is a step of subjecting Compound 7 to a hydrogenation reaction to remove the bromine atom. This step can be carried out according to reactions known per se or reactions analogous thereto, generally, under hydrogen atmosphere, in the presence of a catalyst, in a solvent that does not adversely influence the reaction. Where necessary, a catalytic poison or a base may be added.

Examples of the catalyst include palladiums (palladium on carbon, palladium hydroxide on carbon, oxidation palladium and the like), nickels (Raney nickel catalyst and the like), platinums (platinum oxide, platinum carbon and the like), rhodiums (rhodium carbon and the like) and the like. Among them, palladiums such as palladium on carbon and the like are preferable.

The amount of the catalyst to be used is generally about 0.001-about 1 mol, preferably about 0.01-about 0.5 mol, per 1 mol of Compound 7.

Examples of the catalytic poison used where necessary include amines (ethylene diamine, aniline, quinoline and the like), sulfurs (ethanedithiol, thiophenol and the like), phosphorus (triphenylphosphine and the like), metals (lead acetate, biomass and the like) and the like. Among them, amines such as ethylene diamine and the like are preferable.

The amount of the catalytic poison used where necessary to be used is generally about 0.001-about 2 mol, preferably about 0.01-about 0.5 mol, per 1 mol of Compound 7.

Examples of the base used where necessary include organic amines (trimethylamine, triethylamine, diisopropylethylamine, N-methylmorpholine, 1,8-diazabicyclo[5,4,0]undec-7-ene, pyridine and the like), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like) and the like. Among them, organic amines triethylamine and the like are preferable.

The amount of the base used where necessary to be used is generally about 1 mol-about 10 mol, preferably about 1 mol-about 5 mol, per 1 mol of Compound 7.

Examples of the solvent that does not adversely influence the reaction include the above-mentioned Group A.

The hydrogen pressure for the reaction is generally about 1-about 50 atm, preferably about 1-about 10 atm.

The reaction temperature is generally about 0° C.-about 150° C., preferably about 20° C.-about 100° C.

The reaction time is generally about 0.1 hr-about 72 hr, preferably about 0.5 hr-about 40 hr.

Method 7-B

This step is a step of reacting Compound 7 with a base to produce Compound 8. This step can be carried out according to methods known per se, generally by reacting Compound 7 with a base in a solvent that does not adversely influence the reaction.

Examples of the base include organic amines (1,8-diazabicyclo[5,4,0]undec-7-ene and the like), alkali metal hydrides (potassium hydride, sodium hydride and the like), alkali metal alkoxides (sodium methoxide, sodium ethoxide and the like), organic lithium compounds (n-butyllithium, sec-butyllithium, tert-butyllithium and the like), alkali metal disilazides (lithium hexamethyldisilazide, sodium hexamethyldisilazide, potassium hexamethyldisilazide and the like), alkali metal amides (lithium diisopropylamide, lithium anilide, sodium bis(trimethylsilyl)amide, sodium amide and the like) and the like. Among them, organic lithium compounds such as tert-butyllithium and the like are preferable.

The amount of the base to be used is generally about 1 mol-about 10 mol, preferably about 1 mol-about 5 mol, per 1 mol of Compound V.

Examples of the solvent that does not adversely influence the reaction include ethers (diethyl ether, tetrahydrofuran, 1,4-dioxane, tert-butyl methyl ether, 1,2-dimethoxyethane and the like), aromatic hydrocarbons (benzene, toluene and the like), aliphatic hydrocarbons (hexane, heptane, cyclohexane and the like) and the like. These solvents are used in a combination of two or more at a suitable ratio.

The reaction temperature is generally about −100° C.-about 200° C., preferably about −80° C.-about 100° C.

The reaction time is generally about 0.1 hr-about 100 hr, preferably about 0.5 hr-about 24 hr.

Step 8

This step is a step of removing the PG from Compound 8 to produce Compound 9 or a salt thereof (hereinafter to be abbreviated as Compound 9).

The removal of the protecting group in this step can be carried out according to methods known per se as removal method for a protecting group, or a method analogous thereto.

For example, when PG is a tert-butoxycarbonyl group, then the removal of the protecting group is carried out by reacting Compound 8 with an acid in a solvent that does not adversely influence the reaction.

Examples of the acid include hydrogen chloride, hydrochloric acid, hydrobromic acid, sulfuric acid, trifluoroacetic acid, trifluoromethanesulfonic acid and the like. Among them, hydrogen chloride is preferable.

The amount of the acid to be used is generally about 1 mol-solvent amount, preferably about 1 mol-about 100 mol, per 1 mol of Compound 8.

Examples of the solvent that does not adversely influence the reaction include the above-mentioned Group A.

The reaction temperature is generally about −80° C.-about 200° C., preferably about −80° C.-about 100° C.

The reaction time is generally about 0.1 hr-about 100 hr, preferably about 0.5 hr-about 24 hr.

Step 9

This step is a step of subjecting Compound 5 to a chlorination reaction to produce Compound 8 or a salt thereof. This step can be carried out according to the above-mentioned Step 5 or method analogous thereto. Where necessary, a metal catalyst may be added.

Examples of the metal catalyst used where necessary include palladiums (palladium(II) acetate, palladium(0)-dibenzylidene acetone complex and the like) and the like. Among them, palladium(II) acetate is preferable.

The amount of the metal catalyst used where necessary to be used is generally about 0.1 mol-about 10 mol, preferably about 0.5 mol-about 2 mol, per 1 mol of Compound 5.

[Method B]

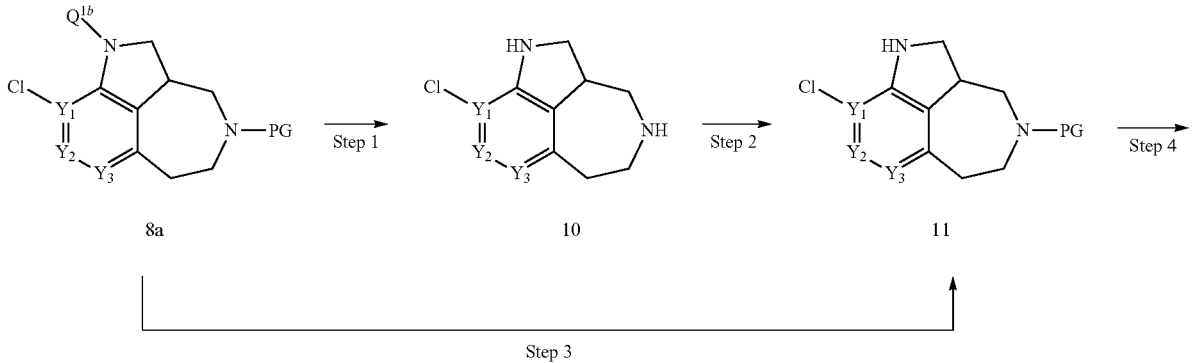

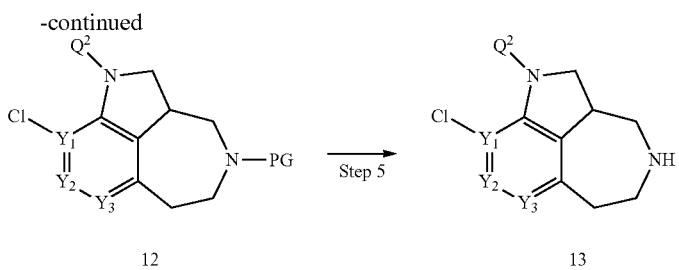

When $Q^{1b}$ of Compound 8a is an amino-protecting group (tert-butoxycarbonyl group, acetyl group and the like) generally used in peptide synthesis and the like, then $Q^{1b}$ can be removed. The removal of $Q^{1b}$ can be carried out according to methods known per se as removal method for a protecting group, or methods analogous thereto.

$Q^2$ is an alkyl group optionally having substituent(s), a cycloalkyl group optionally having substituent(s), an cycloalkenyl group optionally having substituent(s), an alkylcarbonyl group optionally having substituent(s), an alkylsulfonyl group optionally having substituent(s), an alkylsulfinyl group optionally having substituent(s), an alkoxycarbonyl group optionally having substituent(s), an alkylaminocarbonyl group optionally having substituent(s) or the like, and examples of the substituent referred herein include groups that does not adversely influence the reaction. The other symbols are as defined above.

Step 1

This step is a step of removing $Q^{1b}$ and PG from Compound 8a to produce Compound 10.

The removal of $Q^{1b}$ and PG in this step can be carried out according to methods known per se as removal method for a protecting group, or a method analogous thereto.

For example, when $Q^{1b}$ and PG are tert-butoxycarbonyl groups, then the removal of $Q^{1b}$ and PG can be carried out in the same manner as in the method in the above-mentioned Step 8 of Method A.

Step 2

This step is a step of introducing a protecting group into Compound 10 to produce Compound 11. This step can be carried out in the same manner as in the method in the above-mentioned Step 2 of Method A.

Step 3

This step is a step of removing $Q^{1b}$ from Compound 8a to produce Compound 11.

The removal of $Q^{1b}$ in this step can be carried out according to methods known per se as removal method for a protecting group, or a method analogous thereto.

For example, when $Q^{1b}$ is an acetyl group, then the removal of $Q^{1b}$ is carried out by reacting Compound 8a with a base in a solvent that does not adversely influence the reaction.

Examples of the base include alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like), alkali metal alkoxides (sodium methoxide, sodium ethoxide and the like) and the like. Among them, alkali metal salts such as sodium hydroxide, potassium hydroxide, lithium hydroxide and the like are preferable.

The amount of the base to be used is generally about 1 mol-about 100 mol, preferably about 1 mol-about 5 mol, per 1 mol of Compound 8a.

Examples of the solvent that does not adversely influence the reaction include the above-mentioned Group A.

The reaction temperature is generally about –80° C.-about 200° C., preferably about 0° C.-about 100° C.

The reaction time is generally about 0.1 hr-about 100 hr, preferably about 0.5 hr-about 24 hr.

Step 4

This step is a step of reacting the amino group at the 1-position of Compound 11 with an alkylating agent or an acid halide (methanesulfonyl chloride, methyl chloroformate and the like) to produce Compound 12. This step can be carried out in the same manner as in the method in the above-mentioned Step 4 of Method A.

Step 5

This step is a step of removing the protecting group from Compound 12 to produce Compound 13. This step can be carried out in the same manner as in the method in the above-mentioned Step 8 of Method A.

[Method C]

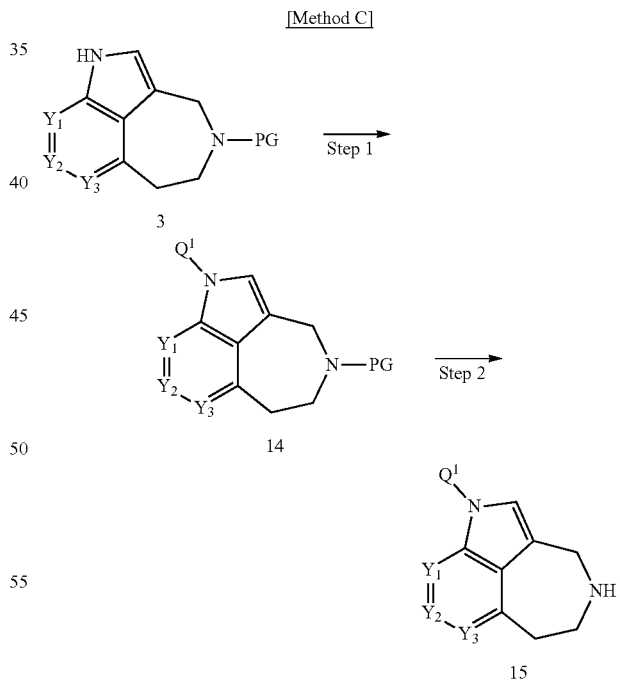

wherein each symbol is as defined above.

Step 1

This step is a step of introducing a substituent into the nitrogen of the indole of Compound 3 to produce Compound 14. This step can be carried out in the same manner as in the method in the above-mentioned Step 4-A of Method A or Step 4-C of Method A.

Step 2

This step is a step of removing the protecting group from Compound 14 to produce Compound 15. This step can be carried out in the same manner as in the method in the above-mentioned Step 8 of Method A.

[Method D]

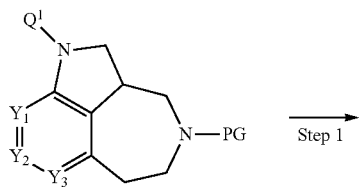

5

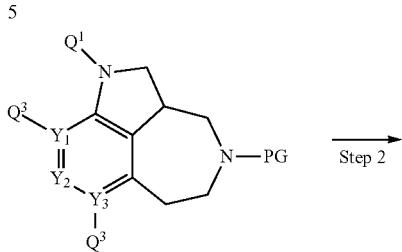

16

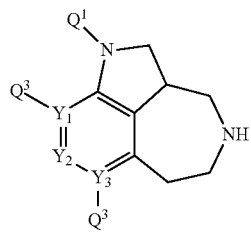

17 wherein $Q^3$ is a halogen atom, and the other symbols are as defined above.

Step 1

This step is a step of reacting Compound 5 with a halogenating agent to produce Compound 16. This step can be carried out according to methods known per se, generally by Compound 5 reacting with a halogenating agent in a solvent that does not adversely influence the reaction.

Examples of the halogenating agent include N-chlorosuccinimide, chlorine, trichloroisocyanuric acid, phosphorus (V) chloride, N-bromosuccinimide, bromine, pyridinium bromide perbromide, dibromoisocyanuric acid, N-iodosuccinimide, iodine and the like.

The amount of the halogenating agent to be used is generally about 2 mol-about 100 mol, preferably about 2 mol -about 5 mol, per 1 mol of Compound 5.

Examples of the solvent that does not adversely influence the reaction include the above-mentioned Group A.

The reaction temperature is generally about −80° C.-about 200° C., preferably about −80° C.-about 100° C.

The reaction time is generally about 0.1 hr-about 100 hr, preferably about 0.5 hr-about 24 hr.

Step 2

This step is a step of removing the protecting group from Compound 16 to produce Compound 17. This step can be carried out in the same manner as in the method in the above-mentioned Step 8 of Method A.

[Method E]

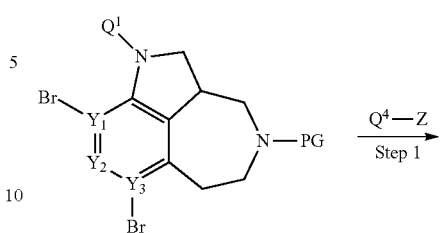

16a

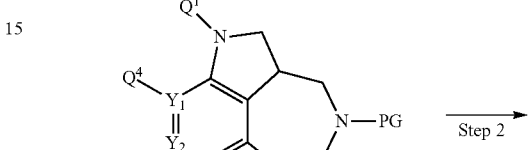

18

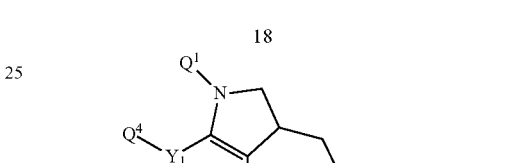

19

20 wherein $Q^4$ is an alkyl group optionally having substituent(s), a cycloalkyl group optionally having substituent(s), an alkenyl group optionally having substituent(s), an cycloalkenyl group optionally having substituent(s), an alkylcarbonyl group optionally having substituent(s) or an alkoxycarbonyl group optionally having substituent(s), and examples of the substituent referred herein include groups that does not adversely influence the reaction. The other symbols are as defined above.

Step 1

This step is a step of converting the bromine atom at the 9-position of Compound 16a to produce Compound 18.

This step can be carried out according to methods known per se, generally by reacting Compound 16a with a base in a solvent that does not adversely influence the reaction, and then reacting the resulting compound with $Q^4$-Z.

Examples of the base include organic amines (1,8-diazabicyclo[5,4,0]undec-7-ene and the like), alkali metal hydrides (potassium hydride, sodium hydride and the like), organic lithium compounds (n-butyllithium, sec-butyllithium, tert-butyllithium and the like), alkali metal disilazides (lithium hexamethyldisilazide, sodium hexamethyldisilazide, potassium hexamethyldisilazide and the like), alkali metal amides (lithium diisopropylamide, lithium anilide, sodium bis(trimethylsilyl)amide, sodium amide and the like) and the like. Among them, organic lithium compounds such as tert-butyllithium and the like are preferable.

The amount of the $Q^4$-Z and base to be used is generally 1 mol-10 mol, preferably about 1 mol-about 2 mol, per 1 mol of Compound 16a.

Examples of the solvent that does not adversely influence the reaction include ethers (diethyl ether, tetrahydrofuran, 1,4-dioxane, tert-butyl methyl ether, 1,2-dimethoxyethane and the like), aromatic hydrocarbons (benzene, toluene and the like), aliphatic hydrocarbons (hexane, heptane, cyclohexane and the like) and the like. These solvents are used in a combination of two or more at a suitable ratio.

The reaction temperature is generally about −100° C.-about 200° C., preferably about −80° C.-about 100° C. The reaction time is generally about 0.1 hr-about 100 hr, preferably about 0.5 hr-about 24 hr.

Step 2

This step is a step of removing the bromine atom from Compound 18 to produce Compound 19. This step can be carried out in the same manner as in the method in the above-mentioned Steps 7-A or 7-B of Method A.

Step 3

This step is a step of removing the protecting group from Compound 19 to produce Compound 20. This step can be carried out in the same manner as in the method in the above-mentioned Step 8 of Method A.

[Method F]

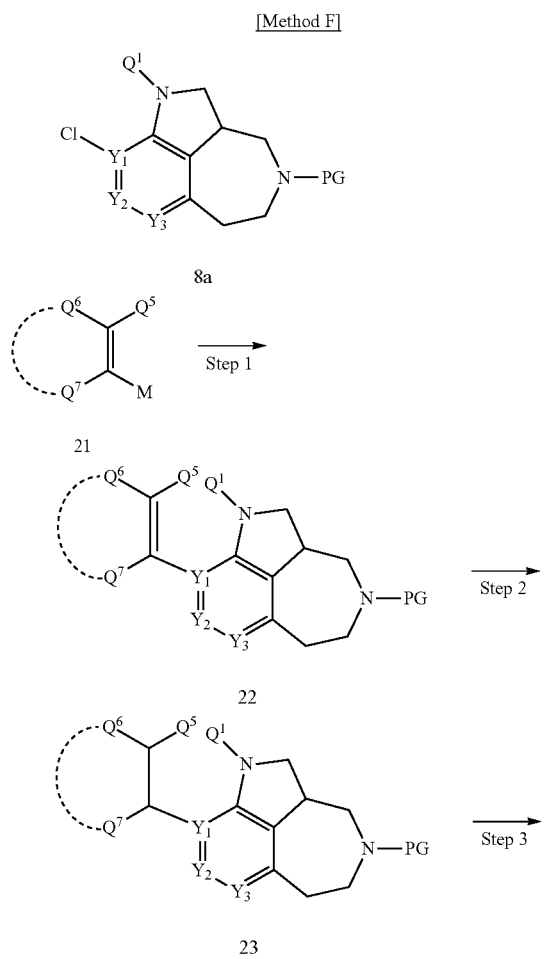

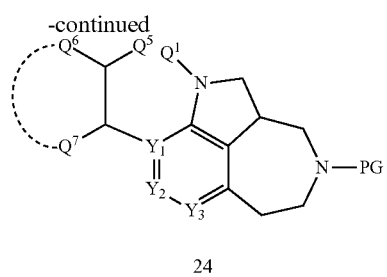

wherein $Q^5$, $Q^6$ and $Q^7$ are each a hydrogen atom, or an alkyl group optionally substituted by a halogen atom or a chalcogen atom, or $Q^6$ and $Q^7$ in combination optionally form a part of ring structure. M is an optionally esterified boric acid, an optionally halogenated magnesium, an optionally halogenated zinc or an optionally alkylated stannum, and the other symbols are as defined above.

Step 1

This step is a step of subjecting Compound 8a to a coupling reaction with Compound 21 or a salt thereof (hereinafter to sometimes be abbreviated as Compound 21) to produce Compound 22.

This step can be carried out according to methods known per se (the method described in Chemical Reviews, 1995, vol. 95, page 2457 and the like), generally, in the presence of a transition metal catalyst and a base, in a solvent that does not adversely influence the reaction. Where necessary, a ligand and a co-catalyst may be added.

The amount of the Compound 21 to be used is generally 1 mol-5 mol, preferably about 1 mol-about 2 mol, per 1 mol of Compound 8a.

Examples of the transition metal catalyst include palladium catalysts (palladium(II) acetate, palladium(II) chloride, tetrakistriphenylphosphine palladium(0) and the like), nickel catalysts (nickel chloride and the like), iron catalysts (acetyl acetone iron and the like) and the like. Among them, palladium catalysts such as palladium(II) acetate and the like are preferable.

The amount of the transition metal catalyst to be used is generally about 0.0001 mol-1 mol, preferably about 0.01 mol-0.5 mol, per 1 mol of Compound 8a.

Examples of the ligand used where necessary include phosphorus ligands (triphenylphosphine, tri-tert-butylphosphine and the like). Among them, triphenylphosphine is preferable.

The amount of the ligand used where necessary to be used is generally about 0.0001 mol-5 mol, preferably about 0.01 mol-2 mol, per 1 mol of Compound 8a.

Examples of the co-catalyst used where necessary include metal oxides (copper(I) oxide, copper(II) oxide, silver oxide and the like) and the like. Among them, copper(II) oxide is preferable.

The amount of the co-catalyst used where necessary to be used is generally about 0.0001 mol-5 mol, preferably about 0.01 mol-2 mol, per 1 mol of Compound 8a.

Examples of the base include organic amines (trimethylamine, triethylamine, diisopropylethylamine, N-methylmorpholine, 1,8-diazabicyclo[5,4,0]undec-7-ene, pyridine and the like), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like), alkali metal hydrides (potassium hydride, sodium hydride and the like), alkali metal alkoxides (sodium methoxide, sodium ethoxide and the like), alkali metal disilazides (lithium hexamethyldisilazide, sodium hexamethyldisilazide, potassium hexamethyldisilazide and the like), alkali metal amides (lithium diisopropylamide, lithium anilide, sodium bis(trimethylsilyl)amide, sodium amide and the like) and the like. Among them, alkali metal salts such as sodium carbonate, potassium carbonate, cesium carbonate, sodium phosphate, potassium phosphate and the like, and alkali metal disilazides such as lithium hexamethyldisilazide, sodium hexamethyldisilazide and the like are preferable.

The amount of the base to be used is generally about 1 mol-about 10 mol, preferably about 1 mol-about 5 mol, per 1 mol of Compound 8a.

Examples of the solvent that does not adversely influence the reaction include the above-mentioned Group A.

The reaction temperature is generally about −10° C.-about 200° C., preferably about 0° C.-about 150° C.

The reaction time is generally about 0.5 hr-about 48 hr, preferably about 0.5 hr-about 16 hr.

Step 2

This step is a step of reducing the double bond of Compound 22 to produce Compound 23. This step can be carried out in the same manner as in the method in the above-mentioned Step 7-A of Method A.

Step 3

This step is a step of removing the protecting group from Compound 23 to produce Compound 24. This step can be carried out in the same manner as in the method in the above-mentioned Step 8 of Method A.

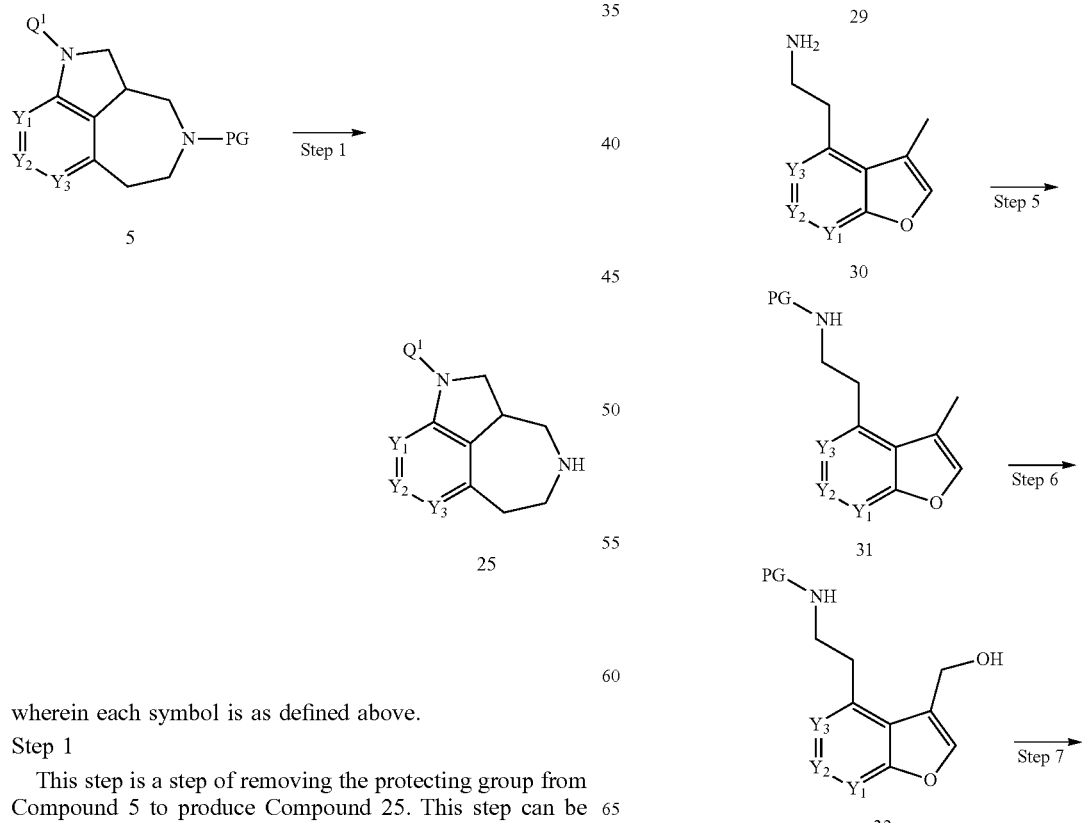

wherein each symbol is as defined above.

Step 1

This step is a step of removing the protecting group from Compound 5 to produce Compound 25. This step can be carried out in the same manner as in the method in the above-mentioned Step 8 of Method A.

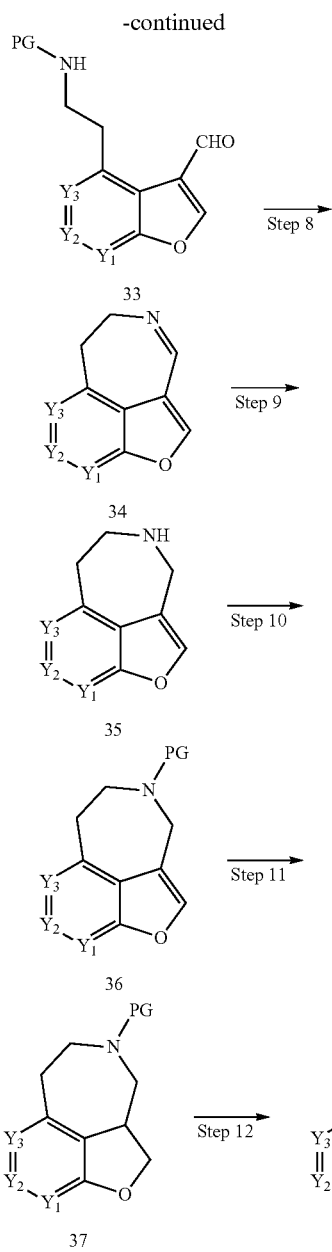

wherein each symbol is as defined above.

Step 1

This step is a step of subjecting Compound 26 to an intramolecular cyclization to produce Compound 27. Compound 26 can be produced according to methods known per se (the method described in Journal of Organic Chemistry, 2004, vol. 69 (1), page 217, and the like) or a method analogous thereto.

This step can be carried out according to methods known per se (the method described in Chemical Reviews, 1995, vol. 95, page 1797, and the like), generally in the presence of an acid catalyst, in a solvent that does not adversely influence the reaction.

Examples of the acid catalyst include mineral acids (sulfuric acid, anhydrous phosphoric acid, polyphosphoric acid and the like), Lewis acids (aluminium chloride, tin tetrachloride, titanium tetrachloride, boron trifluoride, triethylaluminium, diethylaluminum chloride and the like) and the like. Among them, polyphosphoric acid, aluminium chloride and diethylaluminum chloride are preferable.

The amount of the acid catalyst to be used is generally about 0.1 mol-solvent amount, preferably about 1 mol solvent amount, per 1 mol of Compound 26.

Examples of the solvent that does not adversely influence the reaction include the above-mentioned Group A.

The reaction temperature is generally about −100° C.-about 300° C., preferably about 0° C.-about 150° C.

The reaction time is generally about 0.5 hr-about 72 hr, preferably about 0.5 hr-about 16 hr.

Step 2

This step is a step of converting the bromine atom at the 9-position of Compound 27 to produce Compound 28.

This step can be carried out according to methods known per se, generally by reacting Compound 27 with a base in a solvent that does not adversely influence the reaction, and then reacting the resulting compound with a formylating agent.

Examples of the base include organic amines (trimethylamine, triethylamine, diisopropylethylamine, N-methylmorpholine, 1,8-diazabicyclo[5,4,0]undec-7-ene, pyridine and the like), alkali metal hydrides (potassium hydride, sodium hydride and the like), alkali metal alkoxides (sodium methoxide, sodium ethoxide and the like), organic lithium compounds (n-butyllithium, sec-butyllithium, tert-butyllithium and the like), alkali metal disilazides (lithium hexamethyldisilazide, sodium hexamethyldisilazide, potassium hexamethyldisilazide and the like), alkali metal amides (lithium diisopropylamide, lithium anilide, sodium bis(trimethylsilyl)amide, sodium amide and the like) and the like. Among them, organic lithium compounds such as tert-butyllithium and the like are preferable.

The amount of the base to be used is generally about 1 mol-about 10 mol, preferably about 1 mol-about 5 mol, per 1 mol of Compound 27.

Examples of the formylating agent include N,N-dimethylformamide, N-formylpiperidine, N-formylmorpholine, N-formyl-N-methylaniline and the like. Among them, N,N-dimethylformamide is preferable.

The amount of the formylating agent to be used is generally about 1 mol-about 10 mol, preferably about 1 mol-about 5 mol, per 1 mol of Compound 27.

Examples of the solvent that does not adversely influence the reaction include ethers (diethyl ether, tetrahydrofuran, 1,4-dioxane, tert-butyl methyl ether, 1,2-dimethoxyethane and the like), aromatic hydrocarbons (benzene, toluene and the like), aliphatic hydrocarbons (hexane, heptane, cyclohexane and the like) and the like. These solvents are used in a combination of two or more at a suitable ratio.

The reaction temperature is generally about −100° C.-about 200° C., preferably about −80° C.-about 100° C. The reaction time is generally about 0.1 hr-about 100 hr, preferably about 0.5 hr-about 24 hr.

Step 3

This step is a step of reacting Compound 28 with nitromethane to produce Compound 29.

This step is a step of methods known per se (the method described in Tetrahedron Letters, 2001, vol. 42 (12), page 2401, the method described in Chemistry Letters, 2009, vol. 38 (8), page 790, and the like), generally by reacting Compound 28 with nitromethane in a solvent that does not adversely influence the reaction. Where necessary, a base or a catalyst may be added.

The amount of the nitromethane to be used is generally about 1 mol-solvent amount, preferably about 5 mol-solvent amount, per 1 mol of Compound 28.

Examples of the base used where necessary include alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like), alkali metal alkoxides (sodium methoxide, sodium ethoxide and the like) and the like. Among them, alkali metal salts such as sodium carbonate and the like are preferable.

The amount of the base used where necessary to be used is generally about 1 mol-about 10 mol, preferably about 1 mol-about 5 mol, per 1 mol of Compound 28.

Examples of the catalyst used where necessary include ammonium acetate, ammonium formate, tetrabutylammonium chloride and the like. Among them, ammonium acetate is preferable.

The amount of the catalyst used where necessary to be used is generally about 0.01 mol-about 10 mol, preferably about 0.1 mol-about 1 mol, per 1 mol of Compound 28.

Examples of the solvent that does not adversely influence the reaction include the above-mentioned Group A.

The reaction temperature is generally about −100° C.-about 200° C., preferably about 0° C.-about 150° C. The reaction time is generally about 0.1 hr-about 100 hr, preferably about 0.5 hr-about 24 hr.

Step 4

This step is a step of reducing the double bond nitro group of Compound 29 to produce Compound 30. This step can be carried out in the same manner as in the method in the above-mentioned Step 3 of Method A.

Step 5

This step is a step of introducing a protecting group into Compound 30 to produce Compound 31. This step can be carried out in the same manner as in the method in the above-mentioned Step 2 of Method A.

Step 6

This step is a step of introducing a hydroxyl group into Compound 31 to produce Compound 32.

This step can be carried out according to methods known per se, generally by reacting Compound 31 with selenium dioxide in a solvent that does not adversely influence the reaction. Where necessary, a reoxidant may be used.

The amount of the selenium dioxide to be used is generally about 0.1 mol-10 mol, preferably about 1 mol-about 5 mol, per 1 mol of Compound 31.

Examples of the solvent that does not adversely influence the reaction include the above-mentioned Group A.

Examples of the reoxidant used where necessary include hydrogen peroxide water, tert-butylhydroperoxide and the like. Among them, tert-butylhydroperoxide is preferable.

The amount of the reoxidant used where necessary to be used is generally about 1 mol-about 10 mol, preferably about 1 mol-about 5 mol, per 1 mol of Compound 31.

The reaction temperature is generally about −100° C.-about 200° C., preferably about 0° C.-about 150° C. The reaction time is generally about 0.1 hr-about 100 hr, preferably about 0.5 hr-about 24 hr.

Step 7

This step is a step of oxidizing Compound 32 to produce Compound 33.

This step can be carried out according to methods known per se, generally by reacting Compound 32 with an oxidizing agent in a solvent that does not adversely influence the reaction.

Examples of the oxidizing agent include manganese dioxide, chromium complexes (pyridinium chlorochromate, pyridinium dichromate and the like), Swern oxidizing agents (dimethyl sulfoxide-oxalyl chloride, dimethyl sulfoxide-trifluoroacetic anhydride, dimethyl sulfoxide-thionyl chloride and the like), dimethyl sulfoxide-dicyclohexylcarbodiimide under an acidic condition (phosphoric acid, trifluoroacetic acid and the like), sulfur trioxide-pyridine complex, diphosphorus pentaoxide, Kim-Corey oxidizing agents (dimethyl sulfide-N-chlorosuccinimide, dimethyl sulfide-chlorine and the like), tetrapropylammonium perruthenate, hypervalent iodine compounds (1,1,1-triacetoxy-1,1-dihydro-1,2-benziodoxol-3(1H)-one and the like) and the like. Among them, manganese dioxide is preferable.

The amount of the oxidizing agent to be used is generally about 1 mol-about 10 mol, preferably about 1 mol-about 5 mol, per 1 mol of Compound 32.

Examples of the solvent that does not adversely influence the reaction include the above-mentioned Group B.

The reaction temperature is generally about −100° C.-about 200° C., preferably about −50° C.-about 150° C. The reaction time is generally about 0.1 hr-about 100 hr, preferably about 0.5 hr-about 24 hr.

Step 8

This step is a step of removing the protecting group from Compound 33 to produce Compound 34. This step can be carried out in the same manner as in the method in the above-mentioned Step 8 of Method A.

Step 9

This step is a step of reducing the imino group of Compound 34 to produce Compound 35. This step can be carried out in the same manner as in the method in the above-mentioned Step 3 of Method A.

Step 10

This step is a step of introducing a protecting group into Compound 35 to produce Compound 36. This step can be carried out in the same manner as in the method in the above-mentioned Step 2 of Method A.

Step 11

This step is a step of reducing the furan ring of Compound 36 to produce Compound 37. This step can be carried out in the same manner as in the method in the above-mentioned Step 7-A of Method A.

Step 12

This step is a step of removing the protecting group from Compound 37 to produce Compound 38. This step can be carried out in the same manner as in the method in the above-mentioned Step 8 of Method A.

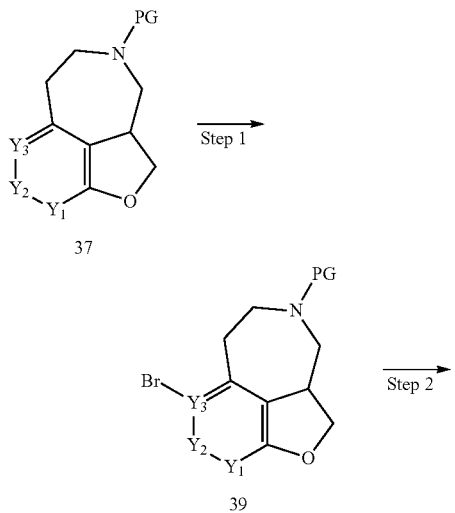

[Method I]

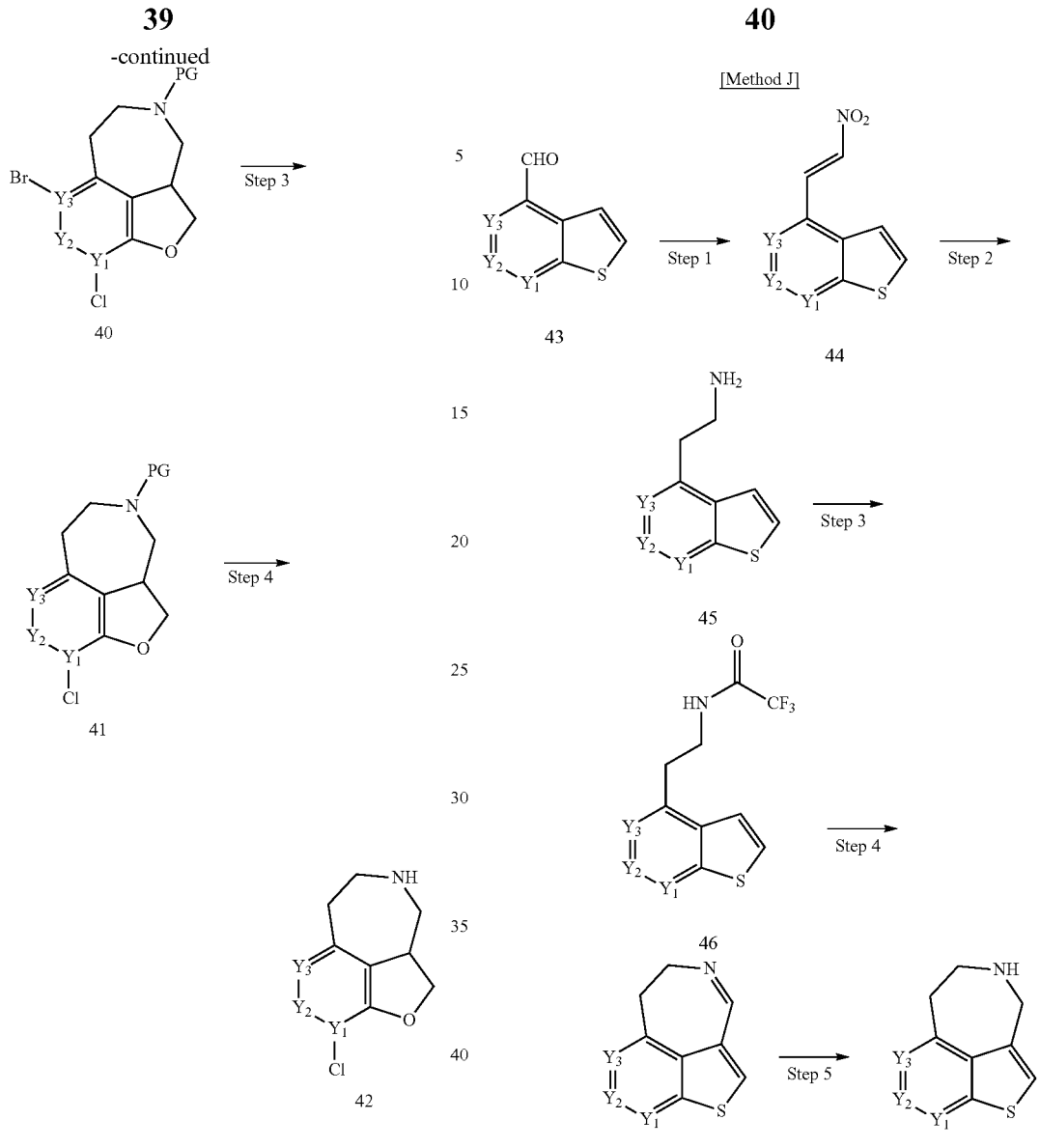

wherein each symbol is as defined above.

Step 1

This step is a step of subjecting Compound 37 to a bromination reaction to produce Compound 39. This step can be carried out in the same manner as in the method in the above-mentioned Step 5 of Method A.

Step 2

This step is a step of subjecting Compound 39 to a chlorination reaction to produce Compound 40. This step can be carried out in the same manner as in the method in the above-mentioned Step 6 of Method A.

Step 3

This step is a step of removing the bromine atom from Compound 40 to produce Compound 41. This step can be carried out in the same manner as in the method in the above-mentioned Steps 7-A or 7-B of Method A.

Step 4

This step is a step of removing the protecting group from Compound 41 to produce Compound 42. This step can be carried out in the same manner as in the method in the above-mentioned Step 8 of Method A.

wherein each symbol is as defined above.

Step 1

This step is a step of reacting Compound 43 with nitromethane to produce Compound 44. This step can be carried out in the same manner as in the method in the above-mentioned Step 3 of Method H.

Step 2

This step is a step of reducing the double bond and nitro group of Compound 44 to produce Compound 45. This step can be carried out in the same manner as in the method in the above-mentioned Step 3 of Method A.

Step 3

This step is a step of introducing a trifluoroacetyl group to Compound 45 to produce Compound 46.

This step can be carried out according to methods known per se, generally by reacting Compound 45 with a trifluoroacetylating agent (trifluoroacetic anhydride, trifluoroethyl acetate and the like), where necessary in the presence of a base, in a solvent that does not adversely influence the reaction.

The amount of the trifluoroacetylating agent to be used is generally 1 mol-10 mol, preferably about 1 mol-about 2 mol, per 1 mol of Compound 45.

Examples of the base used where necessary include organic amines (trimethylamine, triethylamine, diisopropylethylamine, N-methylmorpholine, 1,8-diazabicyclo[5,4,0]undec-7-ene, pyridine and the like), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like) and the like. Among them, organic amines such as triethylamine and the like are preferable.

The amount of the base used where necessary to be used is generally about 0.1 mol-10 mol, preferably about 1 mol-about 5 mol, per 1 mol of Compound 45.

Examples of the solvent that does not adversely influence the reaction include the above-mentioned Group B.

The reaction temperature is generally about −80° C.-about 200° C., preferably about 0° C.-about 100° C.

The reaction time is generally about 0.1 hr-about 200 hr, preferably about 0.5 hr-about 48 hr.

Step 4

This step is a step of introducing a formyl group into Compound 46 and removing the trifluoroacetyl group from Compound 46 to produce Compound 47.

This step can be carried out according to methods known per se (the method described in European Journal of Organic Chemistry, 2007, vol. 12, page 1891 and the like), in the presence of an acid, where necessary in a solvent that does not adversely influence the reaction.

Examples of the acid include titanium tetrachloride, hydrochloric acid, hydrobromic acid, sulfuric acid, trifluoroacetic acid, trifluoromethanesulfonic acid, hydrogen chloride, tosyl acid and the like. Among them, titanium tetrachloride is preferable.

The amount of the acid to be used is generally about 0.01 mol-about 100 mol, per 1 mol of Compound 46.

Examples of the formylating agent include formaldehyde, aqueous formalin, dichloromethyl methyl ether, N,N-dimethylformamide dimethyl acetal and the like. Among them, formaldehyde is preferable.

The amount of the formylating agent to be used is generally 1 mol-10 mol, preferably about 1 mol-about 2 mol, per 1 mol of Compound 46.

Examples of the solvent that does not adversely influence the reaction include the above-mentioned Group A.

The reaction temperature is generally about −80° C.-about 200° C., preferably about −80° C.-about 100° C.

The reaction time is generally about 0.1 hr-about 200 hr, preferably about 0.5 hr-about 48 hr.

Step 5

This step is a step of reducing the imino group of

Compound 47 to produce Compound 48. This step can be carried out in the same manner as in the method in the above-mentioned Step 3 of Method A.

[Method K]

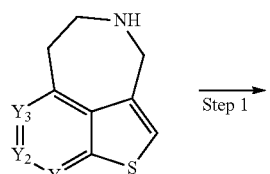

48

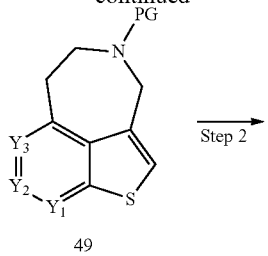

49

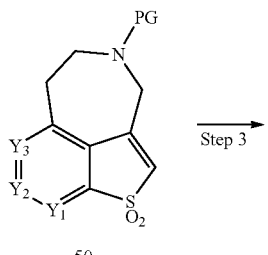

50

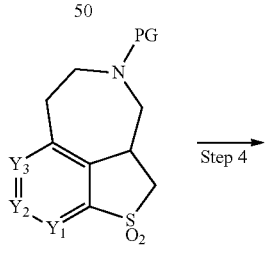

51

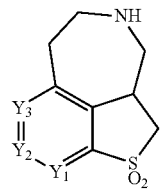

52 wherein each symbol is as defined above.

Step 1

This step is a step of introducing a protecting group into Compound 48 to produce Compound 49. This step can be carried out in the same manner as in the method in the above-mentioned Step 2 of Method A.

Step 2

This step is a step of oxidizing Compound 49 to produce Compound 50. This reaction can be carried out according to methods known per se, generally by reacting Compound 49 with a oxidizing agent in a solvent that does not adversely influence the reaction.

Examples of the oxidizing agent include 3-chlorophenylperbenzoic acid, sodium periodate, hydrogen peroxide water, peracetic acid and the like. Among them, 3-chlorophenylperbenzoic acid is preferable.

The amount of the oxidizing agent to be used is generally about 2 mol-about 100 mol, preferably about 2 mol-about 5 mol, per 1 mol of Compound 49.

Examples of the solvent that does not adversely influence the reaction include the above-mentioned Group A.

The reaction temperature is generally about −80° C.-about 200° C., preferably about −10° C.-about 100° C.

The reaction time is generally about 0.1 hr-about 100 hr, preferably about 0.5 hr-about 24 hr.

Step 3

This step is a step of reducing the double bond of Compound 50 to produce Compound 51. This step can be carried out in the same manner as in the method in the above-mentioned Step 7-A of Method A.

Step 4

This step is a step of removing the protecting group from Compound 51 to produce Compound 52. This step can be carried out in the same manner as in the method in the above-mentioned Step 8 of Method A.

[Method L]

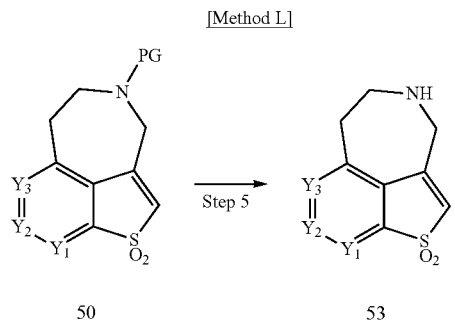

wherein each symbol is as defined above.

Step 1

This step is a step of removing the protecting group from Compound 50 to produce Compound 53. This step can be carried out in the same manner as in the method in the above-mentioned Step 8 of Method A.

The compound of the present invention obtained by the above-mentioned production methods can be isolated and purified by known separation means, for example, recrystallization, distillation, chromatography and the like.

When the compound of the present invention contains an optical isomer, a stereoisomer, a regioisomer or a rotamer, these isomer and mixtures thereof are encompassed in the compound of the present invention, and can be obtained as a single product according to synthetic and separation methods known per se (concentration, solvent extraction, column chromatography, recrystallization and the like). For example, when the compound of the present invention contains an optical isomer, an optical isomer resolved from this compound is also encompassed in the compound of the present invention.

The optical isomer can be produced according to methods known per se. For example, the optical isomer can be obtained using an optically active synthetic intermediate, or by subjecting the final racemate product to optical resolution according to a conventional method. The optical resolution can be carried out according to methods known per se, for example, a fractional recrystallization method, a chiral column method, a diastereomer method, etc.

The compound of the present invention may be a crystal.

The crystal of the compound of the present invention can be produced by crystallizing the compound of the present invention according to crystallization methods known per se. Examples of the crystallization methods include crystallization method from a solution, crystallization method from vapor, crystallization method from the melts, and the like.

Analysis of the obtained crystal is generally carried out by crystal analysis by powder X-ray diffraction. Determination of crystal orientation is carried out by a mechanical method or an optical method and the like.

The compound of the present invention may be a pharmaceutically acceptable cocrystal or cocrystal salt. The cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced according to cocrystallization known per se.

The crystal of the compound of the present invention obtained by the above-mentioned production method has high purity, high quality and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a pharmaceutical composition.

The compound of the present invention may be used as a prodrug. A prodrug of the compound of the present invention means a compound which is converted to the compound of the present invention with a reaction due to an enzyme, an gastric acid, etc. under the physiological condition in the living body, that is, a compound which is converted to the compound of the present invention with oxidation, reduction, hydrolysis, etc. according to an enzyme; or a compound which is converted to the compound of the present invention by hydrolysis etc. due to gastric acid, etc.

A prodrug of the compound of the present invention may be a compound obtained by subjecting an amino group in the compound of the present invention to an acylation, alkylation or phosphorylation (a compound obtained by subjecting an amino group in the compound of the present invention to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxy group in the compound of the present invention to an acylation, alkylation, phosphorylation or boration (a compound obtained by subjecting a hydroxy group in the compound of the present invention to an acetylation, palmitoylation, propanoylation, pivaloylation, succinylation, fumarylation, alanylation, dimethylaminomethylcarbonylation, etc.); a compound obtained by subjecting a carboxyl group in the compound of the present invention to an esterification or amidation (a compound obtained by subjecting a carboxyl group in the compound of the present invention to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, methylamidation, etc.) and the like. Any of these compounds can be produced from the compound of the present invention according to methods known per se.

A prodrug of the compound of the present invention may also be one which is converted to the compound of the present invention under a physiological condition, such as those described in IYAKUHIN no KAIHATSU (Development of Pharmaceuticals), Vol. 7, Design of Molecules, p. 163-198, Published by HIROKAWA SHOTEN (1990).

The compound of the present invention or a prodrug thereof (in the present specification, collectively referred to as "the compound of the present invention") has a superior serotonin 5-HT$_{2C}$ receptor activating action.

In addition, the compound of the present invention has a strong 5-HT$_{2C}$ receptor activity and low toxicity, and it is safe.

The compound of the present invention labeled with a positron-emitting radionuclide such as carbon 11 (11C), fluorine 18 ($^{18}$F), oxygen 15 ($^{15}$O), nitrogen 13 ($^{13}$N) and the like can also be used as a tracer in Positron Emission Tomography (PET).

Since the compound of the present invention has a superior serotonin 5-HT$_2$ receptor activating action, it is useful for as an agent for the treatment or the prophylaxis of all serotonin 5-HT$_{2C}$-related disease, for example, (1) lower urinary tract diseases (including all diseases associated with lower urinary tract symptom mentioned below, overactive bladder, benign prostatic hyperplasia, interstitial cystitis, chronic prostatitis etc.),
urine collection symptom (day time urinary frequency, nocturia, urinary urgency, urinary incontinence, stress urinary incontinence, urge urinary incontinence, mixed urinary incontinence, enuresis, nocturnal enuresis, overflow urinary incontinence, other urinary incontinence, enhanced, decreased or missing bladder sensation etc.), voiding symptom (weak urinary stream, split urinary stream, spraying stream, intermittent urinary stream, voiding postponement, straining at urination, terminal dribbling etc.), post-micturition symptom (sense of residual urine, post-micturition dribble etc.), symptom due to sexual intercourse (coital pain, vaginal dryness, urinary incontinence etc.), symptom due to pelvic organ prolapse (foreign body sensation, lumbago etc.), genital organ pain or lower urinary tract pain (bladder pain, urethral pain, pudendalgia, vaginodynia, scrotal pain, perineal pain, pelvic pain etc.), genital organ or urinary tract pain syndrome (bladder pain syndrome, urethral pain syndrome, pudendalgia syndrome, vaginal syndrome, scrotal pain syndrome, perineal pain syndrome, pelvic pain syndrome etc.), symptom syndrome suggesting lower urinary tract dysfunction (overactive bladder syndrome, a lower urinary tract symptom suggesting bladder outlet obstruction etc.), polyuria, urolithiasis (ureteral calculus, urethral calculus)];

(2) metabolic diseases [diabetes (insulin dependent diabetes, diabetic complications, diabetic retinopathy, diabetic microangiopathy, diabetic neuropathy etc.), impaired glucose tolerance, obesity (malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), benign prostatic hyperplasia, sexual dysfunction etc.];

(3) central nervous system diseases [neurodegenerative diseases (Alzheimer's disease, Down's disease, Parkinson's disease, Creutzfeldt-Jakob disease, amyotrophic lateral sclerosis (ALS), Huntington chorea, diabetic neuropathy, multiple sclerosis etc.), mental diseases (schizophrenia, depression, mania, anxiety neurosis, obsessive-compulsive neurosis, panic disorder, epilepsy, alcohol dependence, drug dependence, anxiety, anxious mental state, emotional abnormality, cyclothymia, nervous erethism, autism, faint, addiction, low sex drive etc.), central nervous system and peripheral nerve disorders (head trauma, spinal damage, brain edema, disorders of sensory function, abnormality of sensory function, disorders of autonomic nervous function, abnormality of autonomic nervous function, whiplash injury etc.), memory disorders (senile dementia, amnesia, cerebrovascular dementia etc.), cerebrovascular disorders (disorders such as cerebral hemorrhage, cerebral infarction etc., and sequelae or complication thereof, asymptomatic cerebrovascular accident, transient cerebral ischemic attack, hypertensive encephalopathia, blood-brain barrier disorder, etc.), recurrence and sequelae of cerebrovascular disorders (neural symptoms, mental symptoms, subjective symptoms, disorders of daily living activities etc.), central nervous system hypofunction after brain blood vessel occlusion, disorder or abnormality of autoregulation ability of brain circulation or renal circulation, sleep disorder etc.];

(4) sexual dysfunction diseases [male erectile dysfunction, dyspermia, female sexual dysfunction etc.];

(5) digestive organ diseases [an irritable bowel syndrome, inflammatory intestine disease, ulcerative colitis, Crohn's disease, diseases caused by a spiral urease-positive gram-negative bacterium (*Helicobacter pylori*, etc.) (gastritis, gastric ulcer, etc.), gastric cancer, postgastrotomy disorder, indigestion, esophageal ulcer, pancreatitis, polyp of the colon, cholelithiasis, hemorrhoids, peptic ulcer, situational ileitis, gluttony, constipation, diarrhea, borborygmus, etc.];

(6) inflammatory or allergic diseases [allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, *meningitidis*, inflammatory ocular disease etc.];

(7) osteoarthropathy diseases [rheumatoid arthritis (rheumatoid arthritis etc.), arthritis deformans, rheumatoid myelitis, osteoporosis, abnormal growth of cells, bone fracture, bone refracture, osteomalacia, osteopenia, Paget's disease of bone, rigid myelitis, articular tissue destruction by gonarthrosis deformans or similar diseases thereto, etc.];

(8) respiratory diseases [cold syndrome, pneumonia, asthma, pulmonary hypertension, pulmonary thrombi/pulmonary obliteration, pulmonary sarcoidosis, pulmonary tuberculosis, interstitial pneumonia, silicosis, adult respiratory distress syndrome, chronic obstructive pulmonary disease, cough etc.];

(9) infectious diseases [HIV infectious diseases, virus infectious diseases due to cytomegalo virus, influenza virus, herpes virus and the like, *rickettsia* infectious diseases, bacterial infectious diseases, sexually-transmitted diseases, *carinii* pneumonia, *Helicobacter pylori* infectious disease, systemic fungal infectious diseases, tuberculosis, invasive staphylococcal infectious diseases, acute viral encephalitis, acute bacterial *meningitidis*, AIDS encephalitis, septicemia, sepsis, sepsis gravis, septic shock, endotoxin shock, toxic shock syndromes etc.];

(10) cancers [primary, metastatic or recurrent breast cancer, prostatic cancer, pancreatic cancer, gastric cancer, lung cancer, colorectal cancers (colon cancer, rectal cancer, anal cancer), esophagus cancer, duodenal cancer, head and neck cancers (cancer of the tongue, pharynx cancer, laryngeal cancer), brain tumor, schwannoma, non-small cell lung cancer, small cell lung cancer, liver cancer, kidney cancer, cancer of the bile duct, uterine cancers (uterine body cancer, cervical cancer), ovary cancer, urinary bladder cancer, skin cancer, hemangioma, malignant lymphoma, malignant melanoma, thyroid cancer, bone tumor, vascular fibroma, retinosarcoma, penile cancer, solid cancer in childhood, Kaposi's sarcoma, Kaposi's sarcoma caused by AIDS, maxillary tumor, fibrous histiocytoma, leiomyosarcoma, rhabdomyosarcoma, liposarcoma, fibroid tumors of the uterus, osteoblastoma, osteosarcoma, chondrosarcoma, cancerous mesothelioma, tumors such as leukemia and the like, Hodgkin's disease etc.];
(11) circulatory diseases [acute coronary artery syndromes (acute myocardial infarction, unstable angina, etc.), peripheral arterial occlusion, Raynaud's disease, Buerger's disease, restenosis after coronary-artery intervention (percutaneous transluminal coronary angioplasty (PTCA), atherectomy (DCA), stenting, etc.), restenosis after coronary-artery bypass operation, restenosis after intervention (angioplasty, atherectomy, stenting, etc.) and bypass operation in other peripheral artery, ischemic cardiac diseases (myocardial infarction, angina, etc.), myocarditis, intermittent claudication, lacunar infarction, arteriosclerosis (atherosclerosis, etc.), cardiac failure (acute cardiac failure, chronic cardiac failure including congestive cardiac failure), arrhythmia, progress of atherosclerotic plaque, thrombosis, hypertension, hypertensive tinnitus, hypotension etc.];
(12) pains [headache, migraine, neuralgia, pelvic organ pain (including bladder pain) etc.];
(13) autoimmune diseases [collagen disease, systemic lupus erythematosus, *scleroderma*, polyarteritis, myasthenia gravis, multiple sclerosis, Sjogren's syndrome, Behcet's disease etc.];
(14) hepatic diseases [hepatitis (including chronic hepatitis), cirrhosis, interstitial hepatic disease etc.];
(15) pancreatic diseases [pancreatitis (including chronic pancreatitis) etc.];
(16) renal diseases [nephritis, glomerulonephritis, glomerulosclerosis, renal failure, thrombotic microangiopathy, dialysis complications, organ disorders including nephropathia by radiation, diabetic nephropathy etc.];
(17) endocrine diseases [Addison's disease, Cushing's syndrome, melanocytoma, primary aldosteronism];
(18) other diseases [for example,
(a) transplant rejection (posttransplantational rejection, posttransplantational polycythemia, hypertension, organ disorder, vascular hypertrophy or graft-versus-host disease etc.);
(b) abnormality in characteristic of blood and/or blood components (enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy etc.);
(c) gynecologic diseases [climacteric disorder, gestational toxicosis, endometriosis, hysteromyoma, ovarian disease, mammary disease, premenstrual syndrome, pelvic organ prolapse, rectum prolapse, cystocele, enterocele etc.],
(d) dermatic diseases (keloid, hemangioma, psoriasis, pruritus etc.);
(e) ophthalmic diseases (glaucoma, ocular hypertension disease etc.);
(f) otolaryngological diseases (Menuel syndrome, tinnitus, gustation disorder, dizziness, disequilibrium, dysphagia etc.);
(g) diseases due to environmental and/or occupational factors (radiation disorder, disorders by ultraviolet ray/infrared ray/laser ray, altitude sickness etc.);
(h) ataxia, stiffness, tremor, motion impairment, akinesia etc.;
(i) chronic fatigue syndrome;
(j) sudden infant death syndrome;
(k) hiccup;
(l) diseases causing palpitation, vertigo, heartburn or the like;
(m) fibromyalgia;
in mammals (mice, rats, hamster, rabbits, cats, dogs, cows, sheep, monkeys, humans etc.).

In addition, serotonin 5-HT$_{2C}$ receptor activators including the compound of the present invention can also be used for the treatment or the prophylaxis of diseases (rectum prolapse etc.) caused by prolapse of organ from the normal position due to weakening of pelvic floor muscles (e.g., cystocele, enterocele). Pelvic organ prolapse, rectum prolapse, cystocele and enterocele are diseases wherein the contractile force of the pelvic floor muscle is insufficient, and bladder, uterus, small intestine, rectum and the like protrudes beyond the vaginal orifice or anal area of the rectal.

That is, the present invention provides to a medicament comprising the compound of the present invention, which is used for the treatment or the prophylaxis of the above-mentioned disease.

The medicament of the present invention is useful as an serotonin 5-HT$_{2C}$ receptor activator, from among these diseases, and also useful for the treatment or the prophylaxis of lower urinary tract symptom, obesity and/or organ prolapse.

When the compound of the present invention is used as the above-mentioned medicament, it is used alone, or in admixture with a suitable, pharmacologically acceptable carrier, for example, excipients (starch, lactose, sucrose, calcium carbonate, calcium phosphate, etc.), binders (starch, arabic gum, carboxymethyl cellulose, hydroxypropyl cellulose, crystalline cellulose, alginic acid, gelatin, polyvinylpyrrolidone, etc.), lubricants (stearic acid, magnesium stearate, calcium stearate, talc, etc.), disintegrants (calcium carboxymethylcellulose, talc, etc.), diluents (water for injection, physiological saline, etc.) and where necessary, with the additives (a stabilizer, a preservative, a colorant, a fragrance, a solubilizing agent, an emulsifier, a buffer, an isotonic agent, etc.) and the like, by ordinary methods, and it can be safely administered orally or parenterally (e.g., intravenous, intramuscular, subcutaneous, intraorgan, intranasal, intradermal, instillation, intracerebral, intrarectal, vaginal, intraperitoneal and intratumor administrations, administration to the vicinity of tumor etc., and direct administration to the lesion), as tablet (including sugar-coated tablet, film-coated tablet, sublingual tablet, orally disintegrating tablet, buccal tablet, and the like), pill, powder, granule, capsule (including soft capsule, microcapsule), troche, syrup, liquid, emulsion, suspension, controlled-release preparation (immediate-release preparation, sustained-release preparation, sustained-release microcapsule), aerosol, films (orally disintegrable films, mouth cavity mucous membrane patch film), injection (subcutaneous injection, intravenous injection, intramuscular injection, intraperitoneal injection), drip infusion, transdermal absorption type preparation, ointment, lotion, adhesive preparation, suppository (rectal suppository, vaginal suppository), pellet, nasal preparation, pulmonary preparation (inhalant), eye drop and the like.

The medicament of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to.

In the medicament of the present invention, while the content of the compound of the present invention varies depending on the form of the preparation, it is generally 0.01-100 wt %, preferably 0.1-50 wt %, more preferably about 0.5-20 wt %, relative to the whole preparation.

While the dose of the compound of the present invention varies depending on administration route, symptom and the like, for example, for oral administration to a patient (adult, body weight: 40 to 80 kg, for example 60 kg) with lower urinary tract symptom, it is 0.01 to 1000 mg/kg body weight/day, preferably 0.01 to 100 mg/kg body weight/day, more preferably 0.05 to 100 mg/kg body weight/day, further preferably 0.1 to 50 mg/kg body weight/day, still more preferably 1 to 50 mg/kg body weight/day, particularly preferably 1 to 25 mg/kg body weight/day, which can be administered in 1, 2 or 3 portions.

The pharmaceutical composition of the present invention is low toxic and can be used safely. Particularly, the following compounds of Examples are superior in the absorbability by oral administration, and can be advantageously used for an oral preparation.

The compound of the present invention can be used along with other medicament.

As a drug that can be blended or combined with the compound of the present invention (hereinafter to be abbreviated as concomitant drug), the following drugs and the like can be used.

(1) Other Drugs for Treating Stress Urinary Incontinence

Adrenaline α1 receptor agonists (e.g., ephedrine hydrochloride, midodrine hydrochloride), adrenaline β2 receptor agonists (e.g., Clenbuterol), noradrenaline reuptake inhibitors, noradrenaline and serotonin reuptake inhibitors (e.g., duloxetine), tricyclic antidepressants (e.g., imipramine hydrochloride), anticholinergic agents or smooth muscle stimulants (e.g., oxybutynin hydrochloride, propiverine hydrochloride, celimeverine hydrochloride), female hormone drugs (e.g., conjugated estrogen (premarin), estriol) and the like.

(2) Agents for Treating Diabetes

Insulin preparations [e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin], insulin sensitizers (e.g., pioglitazone hydrochloride, troglitazone, rosiglitazone or its maleate, reglitazar, isaglitazone, 2,2'-[2(Z)-Butene-1,4-Diyl]Dioxybis(1,4-Phenylene)-bis(methylene)bis[1,2,4-oxadiazole-3,5(2h,4h)-dione], farglitazar, N-[1-(2,4-Dichlorobenzyl)-2-methyl-1H-benzimidazol-6-ylcarbonyl]pentanesulfonamide, rivoglitazone hydrochloride), α-glucosidase inhibitors (e.g., voglibose, acarbose, miglitol, emiglitate), biguanides (e.g., phenformin, metformin, buformin), sulfonylureas (e.g., tolbutamide, glibenclamide, gliclazide, chlorpropamide, tolazamide, acetohexamide, glyclopyramide, glimepiride) and other insulin secretagogues (e.g., repaglinide, senaglinide, mitiglinide or its calcium salt hydrate, GLP-1, nateglinide), dipeptidylpeptidase IV inhibitors (e.g., vildagliptin, sitagliptin, saxagliptin, alogliptin, 6-[2-[2-[2(S)-Cyanopyrrolidin-1-yl]-2-oxoethylamino]ethylamino]pyridine-3-carbonitrile, isoleucine-thiazolidid), β3 agonists (e.g., mirabegron, (R,R)-5-[2-[2-(3-Chlorophenyl)-2-hydroxyethylamino]propyl]-1,3-benzodioxole-2,2-dicarboxylic acid disodium salt), amylin agonists (e.g., pramlintide), phosphotyrosine phosphatase inhibitors (e.g., vanadic acid), gluconeogenesis inhibitors (e.g., glycogen phosphorylase inhibitors, glucose-6-phosphatase inhibitors, glucagon antagonists), SGLT (sodium-glucose cotransporter) inhibitors (e.g., 6-[6-O-(methoxycarbonyl)-beta-D-glucopyranosyloxy]-4-methylphenyl]-1-propanone) and the like.

(3) Agents for Treating Diabetic Complications

Aldose reductase inhibitors (e.g., tolrestat, epalrestat, zenarestat, zopolrestat, fidarestat, minalrestat), neurotrophic factors (e.g., NGF, NT-3), AGE inhibitors (e.g., pimagedine, pyratoxathine, N-phenacylthiazolium bromide), active oxygen scavengers (e.g., thioctic acid), cerebral vasodilators (e.g., tiapride) and the like.

(4) Antihyperlipidemic Agents

Statin compounds inhibiting cholesterol synthesis (e.g., pravastatin, simvastatin, lovastatin, atorvastatin, fluvastatin, cerivastatin or their salt (e.g., sodium salt)), squalene synthase inhibitors, fibrate compounds having triglyceride lowering action (e.g., bezafibrate, clofibrate, simfibrate, clinofibrate) and the like.

(5) Hypotensive Agents

Angiotensin converting enzyme inhibitors (e.g., captopril, enalapril, delapril), angiotensin II antagonists (e.g., losartan, candesartan cilexetil), calcium antagonists (e.g., manidipine, nifedipine, amlodipine, efonidipine, nicardipine), clonidine, and the like.

(6) Antiobesity Agents

Antiobesity drugs acting on the central nervous system (e.g. dexfenfluramine, fenfluramine, phentermine, sibutramine, anfepramone, dexamphetamine, mazindol, phenylpropanolamine, clobenzorex), pancreatic lipase inhibitors (e.g. orlistat), β3 agonists (e.g. mirabegron, anorectic peptides (e.g. leptin, CNTF (Ciliary Neurotrophic Factor)), cholecystokinin agonists (e.g. lintitript) and the like.

(7) Diuretic Agents

Xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide, etc.

(8) Chemotherapeutic Agents

Alkylating agents (e.g., cyclophosphamide, ifosamide), metabolic antagonists (e.g., methotrexate, 5-fluorouracil), antitumor antibiotics (e.g., mitomycin, adriamycin), plant-derived antitumor agents (e.g., vincristine, vindesine, taxol), cisplatin, carboplatin, etoposide, etc. Among these, 5-fluorouracil derivatives such as Furtulon and Neo-Furtulon are preferred.

(9) Immunotherapeutic Agents

Microorganism- or bacterium-derived components (e.g., muramyl dipeptide derivatives, Picibanil), immunopotentiator polysaccharides (e.g., lentinan, schizophyllan, krestin), genetically engineered cytokines (e.g., interferons, interleukins (IL)), colony stimulating factors (e.g., granulocyte colony stimulating factor, erythropoietin) and the like. Among these, IL-1, IL-2 and IL-12 are preferred.

(10) Therapeutic Agents Recognized to Ameliorate Cachexia in Animal Models or Clinical Practice Progesterone derivatives (e.g., megestrol acetate) [Journal of Clinical Oncology, vol. 12, pp. 213, 1994], metoclopramide pharmaceuticals, tetrahydrocannabinol pharmaceuticals (the above references are applied to both), fat metabolism ameliorating drugs (e.g., eicosapentaenoic acid) [British Journal of Cancer, vol. 68, pp. 314, 1993], growth hormones, IGF-1, antibodies to the cachexia-inducing factors such as TNF-α, LIF, IL-6 and oncostatin M, and the like.

(11) Antiinflammatory Agents

Steroids (e.g., dexamethasone), sodium hyaluronate, cyclooxygenase inhibitors (e.g., indomethacin, ketoprofen, loxoprofen, meloxicam, ampiroxicam, celecoxib, rofecoxib) and the like.

(12) Miscellaneous

Glycosylation inhibitors, nerve regeneration promoting drugs (e.g., Timcodar dimesylate), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ebanicline), endothelin receptor antagonists (e.g., atrasentan), monoamine uptake inhibitors (e.g., tramadol), indoleamine uptake inhibitors (e.g., fluoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), local analgesics (e.g., capsaicin), protein kinase C inhibitors (e.g., ruboxistaurin mesylate hydrate), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), hypnotics (e.g., triazolam, zolpidem), anticholinergic agents, $\alpha_1$ receptor blocking agents (e.g., tamsulosin, silodosin, naftopidil), muscle relaxants (e.g., baclofen), potassium channel openers (e.g., nicorandil), calcium channel blocking agents (e.g., nifedipine), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast), etc.

The anticholinergic agent include atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin hydrochloride, tolterodine tartrate) and the like, preferably oxybutynin, propiverine, darifenacin, tolterodine, temiverine, trospium chloride or a salt thereof (e.g., oxybutynin hydrochloride, tolterodine tartrate) can be used. In addition, acetylcholinesterase inhibitors (e.g., distigmine) and the like can be used.

Examples of the NK-2 receptor antagonist include piperidine derivatives such as (S)-5-Fluoro-3-[2-[4-methoxy-4-(phenylsulfinylmethyl)piperidin-1-yl]ethyl]-1H-indole, saredutant, N-[2-(3,4-Dichlorophenyl)-4-[spiro[isobenzofuran-1(3H),4'-piperidin]-1'-yl]butyl]-N-methylbenzamide, N-[2-(3,4-Dichlorophenyl)- 4-[spiro[benzo[b]thiophene-1 (3H),4'-piperidin]-1'-yl]butyl]-N-methylbenzamide S-oxide, 3(R)-[1(S)-( 3,4-Dichlorophenyl)-3-[4-[[S(S)]-2-(methylsulfinyl)phenyl]piperidin-1-yl]propyl]-2-ethyl-2,3-dihydro-1H-isoindol-1-one, N-[2(S)-(3,4-Dichlorophenyl)-4-(spiro [indene-1,4'-piperidin]-1'-yl)butyl]-N-methyl-3,5-bis (trifluoromethyl)benzamide, 1-[2-[3-(3,4-Dichlorophenyl)-1-(3,4,5-trimethoxybenzoyl)pyrrolidin-3(R)-yl]ethyl]-4-phenylpiperidine-4-carboxamide hydrochloride, 3-Cyano-N-[2(S)-( 3,4-dichlorophenyl)-4-[4-[2-[(S)-methylsulfinyl] phenyl]piperidin-1-yl]butyl]-N-methylnaphthalene-1-carboxamide fumarate, (R)-3-(3,4-Dichlorophenyl)-3-[2-[4-(morpholin-4-ylcarbonyl)-4-phenylpiperidin-1-yl]ethyl]-1-(3,4,5-trimethoxybenzoyl)pyrrolidine hydrochloride, N-[3 (R)-(3,4-Dichlorophenyl)-5-[4-(2-oxopiperidin-1-yl) piperidin-1-yl]-2(Z)-(methoxyimino)pentyl]-N-methyl-3,5-dichlorobenzamide, 1-Benzyl-N-[2-[2-(3,4-dichlorophenyl)-4-(3,5-dimethylbenzoyl)piperazin-1-yl]-2-oxoethyl]piperidin-4-amine and the like; perhydroisoindole derivatives such as (3aR,4R,5R,7aR)-2-[2-(Indol-3-yl) acetyl]-4-(2-methoxyphenyl)-7,7-diphenylperhydroisoindole-4,5-diol and the like; quinoline derivatives such as 2-Phenyl-3-[4-(1-piperidinyl)piperidin-1-ylmethyl]-N-[1 (S),2,2-trimethylpropyl]quinoline-4-carboxamide and the like; pyrrolopyrimidine derivatives such as 4-(4-Chlorophenylamino)-2-[4-[2-(hydroxyimino)propanoyl]piperazin-1-yl]-6-isopropyl-6,7-dihydro-5H-pyrrolo[3,4-d]pyrimidin-7-one and the like; pseudopeptide derivatives such as Cyclo [N-[2-(acetylamino)-2-deoxy-beta-D-glucopyranosyl]-L-asparaginyl-L -aspartyl-L-tryptophyl-L-phenylalanyl-[2(S), 3-diaminopropionyl]-L-leucine]-C-4,2-N-3,5-lactam and the like; in addition, Cyclohexylcarbonyl-glycyl-alanyl-D-tryptophyl -phenylalanine dimethylamide, 5-(3,4-Dichlorophenyl)-4(R)-[N -methyl-3,5-bis(trifluoromethyl)benzamido]-N-[2-oxoperhydroazepin-3(R)-yl]-2(E)-pentenamide, N-[1(R)-(3,4-Dichlorobenzyl)-4-[hexahydro-2-oxo-1H-azepin-3(R)-ylamino]-4-oxo-2(E)-butenyl]-N-methyl-3,5-bis(trifluoromethyl)benzamide, Benzoyl-alanyl-alanyl-D-tryptophyl-phenylalanyl-D-prolyl-prolyl-norleucylamide, 4-[1-[2-[1-(Cyclopropylmethyl)-3(S)-(3,4-dichlorophenyl)-6-oxopiperidin-3-yl]ethyl]azetidin-3-yl] piperazine-1-sulfonamide, Cyclo[L-Methionyl-L-aspartyl-L-tryptophyl-L-phenylalanyl-[2(S),3-diaminopropionyl]-leucine]C-4,2-N-3,5-lactam, or a salt thereof, and the like.

In the combination drug, the administration time of the compound of the present invention and the concomitant drug is not restricted, and the compound of the present invention or a pharmaceutical composition thereof and the concomitant drug or a pharmaceutical composition thereof can be administered to the administration subject simultaneously, or may be administered at different times. The dosage of the concomitant drug may be determined according to the dose clinically used, and can be appropriately selected depending on the administration subject, administration route, disease, combination and the like.

The administration mode of the combination drug is not particularly restricted, and it is sufficient that the compound of the present invention and the concomitant drug are combined in administration. Examples of such administration mode include the following methods:

(1) The compound of the present invention or a pharmaceutical composition thereof and the concomitant drug are simultaneously produced to give a single preparation which is administered;

(2) The compound of the present invention or a pharmaceutical composition thereof and the concomitant drug or a pharmaceutical composition thereof are separately produced to give two kinds of preparations which are administered simultaneously by the same administration route;

(3) The compound of the present invention or a pharmaceutical composition thereof and the concomitant drug or a pharmaceutical composition thereof are separately produced to give two kinds of preparations which are administered by the same administration route at different times;

(4) The compound of the present invention or a pharmaceutical composition thereof and the concomitant drug or a pharmaceutical composition thereof are separately produced to give two kinds of preparations which are administered simultaneously by different administration routes;

(5) The compound of the present invention or a pharmaceutical composition thereof and the concomitant drug or a pharmaceutical composition thereof are separately produced to give two kinds of preparations which are administered by different administration routes at different times (e.g., the compound of the present invention or a pharmaceutical composition thereof; the concomitant drug or a pharmaceutical composition thereof are administered in this order, or in the reverse order); and the like.

The mixing ratio of the compound of the present invention and the concomitant drug in the combination drug of the present invention can be appropriately determined according to the subject of administration, administration route, disease and the like.

For example, while the content of the compound of the present invention in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the concomitant drug in the combination drug of the present invention varies depending on the form of the preparation, it is generally about 0.01 to 5 about 100 wt %, preferably about 0.1 to about 50 wt %, more preferably about 0.5 to about 20 wt %, relative to the whole preparation.

While the content of the additive such as a carrier and the like in the combination drug of the present invention varies depending on the form of the preparation, it is generally about 1 to about 99.99 wt %, preferably about 10 to about 90 wt %, relative to the whole preparation.

Similar contents can be employed when the compound of the present invention and the concomitant drug are independently formulated.

While the dose varies depending on the kind of the compound of the present invention, administration route, symptom, age of patients and the like, for example, for oral administration to an adult patient with stress urinary incontinence and/or obesity, it is about 0.005 to 50 mg, preferably about 0.05 to 10 mg, more preferably about 0.2 to 4 mg/kg body weight/day, which can be administered in 1 to about 3 portions.

When the pharmaceutical composition of the present invention is a sustained-release preparation, the dose varies depending on the kind and content of the compound of the present invention, dosage form, period of sustained drug release, subject animal of administration (e.g., mammals such as human, rat, mouse, cat, dog, rabbit, bovine, swine and the like) and administration object. For parenteral administration, for example, about 0.1 to about 100 mg of the compound of the present invention only needs to be released in one week from the administered preparation.

The dose of the concomitant drug may be set within the range such that it causes no problems of side effects. The daily dose as the concomitant drug varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of drugs is usually in the order of about 0.001 to 2000 mg, preferably about 0.01 to 500 mg, and more preferably about 0.1 to 100 mg, per 1 kg body weight of mammals, which may be administered once a day or in one to four divided portions a day.

The combination drug of the present invention has low toxicity, for example, the compound of the present invention or/and the above-mentioned concomitant drug are mixed with a pharmacologically acceptable carrier according to methods known per se to give pharmaceutical composition, or formulated into tablet (including sugar-coated tablet, film-coated tablet), powder, granule, capsule (including soft capsule), liquid, injection, suppository, sustained-release preparation and the like. It can be safely administered orally or parenterally (topically, intrarectal, intravenous and the like).

Examples of the pharmacologically acceptable carrier for preparation of the combination drug of the present invention include those similar to the carrier used for the above-mentioned pharmaceutical composition of the present invention.

EXAMPLE

The present invention is explained in detail in the following by referring to Reference Examples, Examples, Formulation Examples and Experimental Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH silica gel means use of aminopropylsilane-bound silica gel. In HPLC (high performance liquid chromatography), C18 means use of octadecyl-bound silica gel. The ratios of elution solvents are volume mixing ratios, unless otherwise specified.

In Formulation Examples, as an additive for formulation (e.g., lactose, cornstarch), products conforming to standards Japanese Pharmacopoeia Sixteen Edition or Japanese Pharmaceutical Excipients 2003 can be used.

In the following Reference Examples and Examples, following abbreviations are used.

LC: liquid chromatography
MS: mass analysis spectrum
ESI: Electrospray ionization method
NMR: nuclear magnetic resonance spectrum
Hz: hertz
J: coupling constant
m: multiplet
q: quartet
t: triplet
d: doublet
dd: double doublet
s: singlet
br: broad
dt: double triplet
dq: double quartet
td: triple doublet
brs: broad singlet Boc₂O: di-tert-butyl dicarbonate
M: mol/L
CDCl₃: deuterochloroform
DMF: N,N-dimethylformamide
THF: tetrahydrofuran
DMSO: dimethyl sulfoxide
DMA: N,N-dimethylacetamide
DME: dimethoxyethane
IPE: diisopropyl ether
TFA: trifluoroacetic acid
AcONH₄: ammonium acetate
NH₄HCO₃: ammonium bicarbonate
DMAP: 4-dimethylaminopyridine
Pd₂(dba)₃: tris(dibenzylideneacetone)dipalladium(O)

¹H NMR (proton nuclear magnetic resonance spectrum) was measured by Fourier-transform type NMR. For the analysis, ACD/SpecManager (trade name) and the like were used. Peaks with very broad protons such as a hydroxy group, an amino group and the like are not described.

MS (mass spectrum) was measured by LC/MS (liquid chromatography mass spectrometer). As ionization method, ESI (Electro Spray Ionization) method, or APCI (Atomospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxy group (—OH), a peak after elimination of H₂O may be observed as a fragment ion. In the case of a salt, a molecular ion peak or fragment ion peak of free form is generally observed.

Example 1

3,4,5,6-tetrahydro-1H-azepino[3,4,5-cd]indole hydrochloride

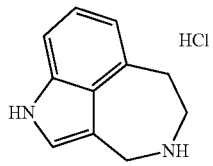 [SMILES: c1cc2c3c(c[nH]c3c1)CNCC2 ; Cl]

A) tert-butyl 1,3,5,6-tetrahydro-4H-azepino[3,4,5-cd]indole-4-carboxylate

To a mixture of 2-(1H-indol-4-yl)ethanamine (400 mg) and 1M hydrochloric acid (10 mL) was added saturated aqueous sodium bicarbonate solution until the pH became 6.5. Then, aqueous formalin (37 wt %, 195 μL) was added thereto. The reaction mixture was stirred at room temperature for 5 hr while maintaining the pH to 6.5. The pH of the reaction mixture was adjusted to 11-12 with 25% aqueous ammonia, and the mixture was extracted with ethyl acetate. The extract was washed with saturated brine, dried over anhydrous sodium sulfate, and filtered, and the solvent was evaporated under reduced pressure. The residue was diluted with THF (10 mL), and the Boc₂O (599 μL) was added thereto. The reaction mixture was stirred at room temperature for 2 hr, and the solvent was evaporated under reduced pressure. The residue was purified by silica gel column chromatography (ethyl acetate/hexane) to give the title compound (406 mg).

¹H NMR (300 MHz, CDCl₃) δ 1.38-1.51 (9H, m), 3.24-3.41 (2H, m), 3.70-3.89 (2H, m), 4.71-4.85 (2H, m), 6.85-6.97 (1H, m), 7.04 (1H, brs), 7.11 (1H, dd, J=7.7 Hz), 7.19-7.25 (1H, m), 8.06 (1H, brs).

B) 3,4,5,6-tetrahydro-1H-azepino[3,4,5-cd]indole hydrochloride

A reaction mixture of tert-butyl 1,3,5,6-tetrahydro-4H-azepino[3,4,5-cd]indole-4-carboxylate (200 mg), 4M hydrogen chloride/ethyl acetate (2 mL) and ethanol (1 mL) was stirred at room temperature for 2 hr, and the solvent was evaporated under reduced pressure. The residue was recrystallized from methanol-ethanol-IPE to give the title compound (131 mg).

Example 2

2,2a,3,4,5,6-hexahydro-1H-azepino[3,4,5-cd]indole dihydrochloride

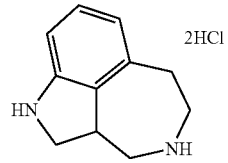 [SMILES: c1cc2c3c(c1)NCC3CNCC2 ; "2HCl"]

A) tert-butyl 1,2,2a,3,5,6-hexahydro-4H-azepino[3,4,5-cd]indole-4-carboxylate

To a mixture of tert-butyl 1,3,5,6-tetrahydro-4H-azepino[3,4,5-cd]indole-4-carboxylate (15.3 g) and acetic acid (150 mL) was added sodium cyanoborohydride (10.1 g). The reaction mixture was stirred at room temperature for 5 hr. To the reaction mixture was added water (150 mL), and the mixture was basified with sodium hydroxide, and extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (12.7 g).

MS (ESI+): [M+H]⁺ 275.2.

B) 2,2a,3,4,5,6-hexahydro-1H-azepino[3,4,5-cd]indole dihydrochloride

The title compound was obtained in the same manner as in Step B of Example 1.

Example 3

1-methyl-3,4,5,6-tetrahydro-1H-azepino[3,4,5-cd]indole

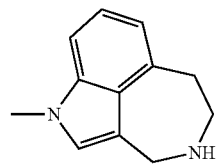

A) tert-butyl 1-methyl-1,3,5,6-tetrahydro-4H-azepino[3,4,5-cd]indole-4-carboxylate To a mixture of tert-butyl 1,3,5,6-tetrahydro-4H-azepino [3,4,5-cd]indole-4-carboxylate (300 mg), methyl iodide (103 µL), THF (3 mL) and DMF (1 mL) was added sodium hydride (60%, 66 mg). The reaction mixture was stirred at room temperature for 3 hr, water was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (271 mg).

$^1$H NMR (300 MHz, CDCl$_3$) δ 1.37-1.49 (9H, m), 3.21-3.40 (2H, m), 3.67-3.86 (5H, m), 4.65-4.85 (2H, m), 6.91 (2H, s), 7.14 (2H, d, J=3.8 Hz).

B) 1-methyl-3,4,5,6-tetrahydro-1H-azepino[3,4,5-cd]indole

A reaction mixture of tert-butyl 1-methyl-1,3,5,6-tetrahydro-4H-azepino[3,4,5-cd]indole-4-carboxylate (271 mg) and 4M hydrogen chloride/ethyl acetate (2 mL) was stirred at room temperature for 2 hr, 1M aqueous sodium hydroxide solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (NH silica gel, ethyl acetate/hexane) to give the title compound (83 mg).

Example 4

1-methyl-2,2a,3,4,5,6-hexahydro-1H-azepino[3,4,5-cd]indole hydrochloride

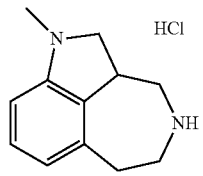

A) tert-butyl 1-methyl-1,2,2a,3,5,6-hexahydro-4H-azepino[3,4,5-cd]indole-4-carboxylate A reaction mixture of tert-butyl 1,2,2a,3,5,6-hexahydro-4H-azepino[3,4,5-cd]indole-4-carboxylate (300 mg), aqueous formalin (37 wt %, 178 µL), sodium triacetoxyborohydride (348 mg), acetic acid (188 µL) and acetonitrile (5 mL) was stirred at room temperature for 16 hr, water was added thereto, and the mixture was extracted with ethyl acetate. The extract was washed with water and saturated brine, dried over anhydrous sodium sulfate, and the solvent was evaporated under reduced pressure. The residue was purified by silica gel column chromatography (ethyl acetate/hexane) to give the title compound (261 mg).

MS (ESI+): [M+H]$^+$ 289.4.

B) 1-methyl-2,2a,3,4,5,6-hexahydro-1H-azepino[3,4,5-cd]indole hydrochloride A reaction mixture of tert-butyl 1-methyl-1,2,2a,3,5,6-hexahydro-4H-azepino[3,4,5-cd]indole-4-carboxylate (261 mg) and 4M hydrogen chloride/ethyl acetate (5 mL) was stirred at room temperature for 2 hr, 1M aqueous sodium hydroxide solution was added thereto, and the mixture was extracted with ethyl acetate. The extract was washed with saturated brine, dried over anhydrous sodium sulfate, and filtered, and the solvent was evaporated under reduced pressure. To the obtained residue was added 6M hydrochloric acid (152 µL), and the solvent was evaporated under reduced pressure. The residue was recrystallized from ethanol-IPE to give the title compound (170 mg).

Example 5

9-chloro-1-methyl-2,2a,3,4,5,6-hexahydro-1H-azepino[3,4,5-cd]indole hydrochloride

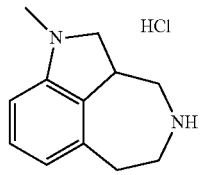

A) tert-butyl 7-bromo-1-methyl-1,2,2a,3,5,6-hexahydro-4H-azepino[3,4,5-cd]indole-4-carboxylate To a mixture of tert-butyl 1-methyl-1,2,2a,3,5,6-hexahydro-4H-azepino[3,4,5-cd]indole-4-carboxylate (5.0 g) and acetonitrile (100 mL) was added N-bromosuccinimide (3.3 g) at 0° C. The reaction mixture was stirred at 0° C. for 1 hr, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (5.6 g).

MS (ESI+): [M+H]+367.1.

B) tert-butyl 7-bromo-9-chloro-1-methyl-1,2,2a,3,5,6-hexahydro-4H-azepino[3,4,5-cd]indole-4-carboxylate To a mixture of tert-butyl 7-bromo-1-methyl-1,2,2a,3,5,6-hexahydro-4H-azepino[3,4,5-cd]indole-4-carboxylate (5.5 g) and acetonitrile (100 mL) was added N-chlorosuccinimide (2.2 g) at room temperature. The reaction mixture was stirred at 40° C. for 4 hr, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (3.2 g).

MS (ESI+): [M+H]$^+$ 401.1.

C) tert-butyl 9-chloro-1-methyl-1,2,2a,3,5,6-hexahydro-4H-azepino[3,4,5-cd]indole-4-carboxylate To a mixture of tert-butyl 7-bromo-9-chloro-1-methyl-1,2,2a,3,5,6-hexahydro-4H-azepino[3,4,5-cd]indole-4-carboxylate (2.4 g) and THF (50 mL) was added tert-butyllithium/hexane solution (1.6 M, 5.3 mL) at −78° C. under argon atmosphere. The reaction mixture was stirred at −78° C. for 30 min, water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (1.4 g).

MS (ESI+): [M+H]$^+$ 323.2.

D) 9-chloro-1-methyl-2,2a,3,4,5,6-hexahydro-1H-azepino[3,4,5-cd]indole hydrochloride The title compound was obtained in the same manner as in Step B of Example 4.

Example 6

7-chloro-1-methyl-2,2a,3,4,5,6-hexahydro-1H-azepino[3,4,5-cd]indole hydrochloride

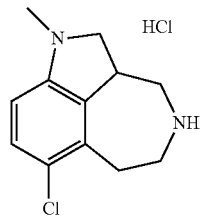

A) tert-butyl 7-chloro-1-methyl-1,2,2a,3,5,6-hexahydro-4H-azepino[3,4,5-cd]indole-4-carboxylate To a mixture of tert-butyl 1-methyl-1,2,2a,3,5,6-hexahydro-4H-azepino[3,4,5-cd]indole-4-carboxylate (182 mg) and acetonitrile (5 mL) was added N-chlorosuccinimide (89 mg). The reaction mixture was stirred at room temperature for 2 hr, water was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) and HPLC (C18, mobile phase: water/acetonitrile (5 mM, containing AcONH$_4$)) to give the title compound (134 mg).

MS (ESI+): [M+H]$^+$ 323.3.

B) 7-chloro-1-methyl-2,2a,3,4,5,6-hexahydro-1H-azepino[3,4,5-cd]indole hydrochloride A reaction mixture of tert-butyl 7-chloro-1-methyl-1,2,2a,3,5,6-hexahydro-4H-azepino[3,4,5-cd]indole-4-carboxylate (134 mg) and 4M hydrogen chloride/ethyl acetate (2 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and the solvent was evaporated under reduced pressure. The residue was purified by silica gel column chromatography (NH silica gel, ethyl acetate/hexane). To the obtained residue were added ethanol and 6M hydrochloric acid (31 μL), and the solvent was evaporated under reduced pressure. The residue was recrystallized from ethanol-IPE to give the title compound (40 mg).

Example 7

7,9-dichloro-1-methyl-2,2a,3,4,5,6-hexahydro-1H-azepino[3,4,5-cd]indole

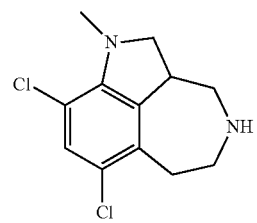

A) tert-butyl 7,9-dichloro-1-methyl-1,2,2a,3,5,6-hexahydro-4H-azepino[3,4,5-cd]indole-4-carboxylate To a mixture of tert-butyl 1-methyl-1,2,2a,3,5,6-hexahydro-4H-azepino[3,4,5-cd]indole-4-carboxylate (182 mg) and acetonitrile (5 mL) was added N-chlorosuccinimide (89 mg). The reaction mixture was stirred at room temperature for 2 hr, water was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) and HPLC (C18, mobile phase: water/acetonitrile (5 mM, containing AcONH$_4$)) to give the title compound (8 mg).

MS (ESI+): [M+H]$^+$ 357.4.

B) 7,9-dichloro-1-methyl-2,2a,3,4,5,6-hexahydro-1H-azepino[3,4,5-cd]indole

A reaction mixture of tert-butyl 7,9-dichloro-1-methyl-1,2,2a,3,5,6-hexahydro-4H-azepino[3,4,5-cd]indole-4-carboxylate (8 mg) and 4M hydrogen chloride/ethyl acetate (2 mL) was stirred at room temperature for 2 hr, saturated aqueous sodium bicarbonate solution was added thereto, and the mixture was extracted with ethyl acetate. The extract was m washed with saturated brine, dried over anhydrous sodium sulfate, and filtered, and the solvent was evaporated under reduced pressure to give the title compound (4 mg).

Example 8

(2aR)-9-chloro-1-methyl-2,2a,3,4,5,6-hexahydro-1H-azepino[3,4,5-cd]indole hydrochloride

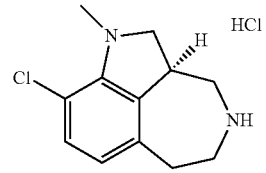

A reaction mixture of tert-butyl 9-chloro-1-methyl-1,2,2a,3,5,6-hexahydro-4H-azepino[3,4,5-cd]indole-4-carboxylate (1.0 g) and 4M hydrogen chloride/ethyl acetate (20 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. The residue was resolved by HPLC (column: CHIRALPAK ADH (trade name), 20 mmID×250 mmL, manufactured by Daicel Chemical Industries, mobile phase: carbon dioxide/methanol/diethylamine=840/160/3) to give the compound (258 mg) having a shorter retention time. To a mixture of the obtained compound and ethanol (1 mL) was added 4M hydrogen chloride/ethyl acetate (319 μL), and the solvent was evaporated under reduced pressure. The residue was recrystallized from ethanol-IPE to give the title compound (264 mg).

Example 9

(2aS)-9-chloro-1-methyl-2,2a,3,4,5,6-hexahydro-1H-azepino[3,4,5-cd]indole hydrochloride

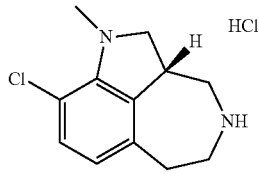

A reaction mixture of tert-butyl 9-chloro-1-methyl-1,2,2a, 3,5,6-hexahydro-4H-azepino[3,4,5-cd]indole-4-carboxylate (1.0 g) and 4M hydrogen chloride/ethyl acetate (20 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and the solvent was evaporated under reduced pressure. The residue was resolved by HPLC (column: CHIRALPAK ADH (trade name), 20 mmID×250 mmL, manufactured by Daicel Chemical Industries, mobile phase: carbon dioxide/methanol/diethylamine=840/160/3) to give the compound (282 mg) having a longer retention time. To a mixture of the obtained compound and ethanol (1 mL) was added 4M hydrogen chloride/ethyl acetate (348 μL), and the solvent was evaporated under reduced pressure. The residue was recrystallized from ethanol-IPE to give the title compound (283 mg).

$^1$H NMR (300 MHz, DMSO-$d_6$) δ 2.78-3.00 (4H, m), 3.02 (3H, s), 3.06-3.21 (1H, m), 3.36-3.60 (2H, m), 3.64-3.85 (2H, m), 6.51 (1H, d, J=7.9 Hz), 6.98 (1H, d, J=7.9 Hz), 9.06-9.46 (2H, m).

Example 10

1,9-dimethyl-2,2a,3,4,5,6-hexahydro-1H-azepino[3,4,5-cd]indole hydrochloride

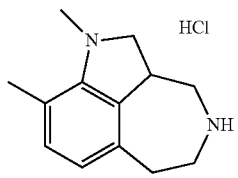

A) tert-butyl 7,9-dibromo-1-methyl-1,2,2a,3,5,6-hexahydro-4H-azepino[3,4,5-cd]indole-4-carboxylate To a mixture of tert-butyl 1-methyl-1,2,2a,3,5,6-hexahydro-4H-azepino[3,4,5-cd]indole-4-carboxylate (5.0 g) and acetonitrile (100 mL) was added N-bromosuccinimide (3.3 g) at 0° C. The reaction mixture was stirred at 0° C. for 1 hr, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (514 mg).

$^1$H NMR (300 MHz, CDCl$_3$) δ 1.49 (9H, s), 2.52-3.02 (2H, m), 3.08 (3H, s), 3.31 (1H, dd, J=16.2, 5.7 Hz), 3.46-3.74 (2H, m), 4.00-4.33 (2H, m), 7.43 (1H, s).

B) tert-butyl 7-bromo-1,9-dimethyl-1,2,2a,3,5,6-hexahydro-4H-azepino[3,4,5-cd]indole-4-carboxylate To a mixture of tert-butyl 7,9-dibromo-1-methyl-1,2,2a, 3,5,6-hexahydro-4H-azepino[3,4,5-cd]indole-4-carboxylate (100 mg) and THF (2 mL) was added tert-butyllithium/hexane solution (1.6 M, 282 μL) at −78° C. under argon atmosphere, and the mixture was stirred at −78° C. for 10 min. Methyl iodide (21 μL) was added thereto, and the reaction mixture was stirred at −78° C. under argon atmosphere for 2 hr. Water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (39 mg).

MS (ESI+): [M+H]$^+$ 381.2.

C) tert-butyl 1,9-dimethyl-1,2,2a,3,5,6-hexahydro-4H-azepino[3,4,5-cd]indole-4-carboxylate A mixture of tert-butyl 7-bromo-1,9-dimethyl-1,2,2a,3,5, 6-hexahydro-4H-azepino[3,4,5-cd]indole-4-carboxylate (39 mg), 10% palladium on carbon (5 mg), triethylamine (21 μL) and ethanol (2 mL) was stirred under hydrogen atmosphere for 30 min. The catalyst was removed by filtration, and the solvent was evaporated under reduced pressure. The residue was purified by silica gel column chromatography (ethyl acetate/hexane) to give the title compound (29 mg).

MS (ESI+): [M+H]$^+$ 303.2.

D) 1,9-dimethyl-2,2a,3,4,5,6-hexahydro-1H-azepino[3,4,5-cd]indole hydrochloride

The title compound was obtained in the same manner as in Step B of Example 4.

Example 11

(2aS)-1,9-dimethyl-2,2a,3,4,5,6-hexahydro-1H-azepino[3,4,5-cd]indole 0.5 sulfate

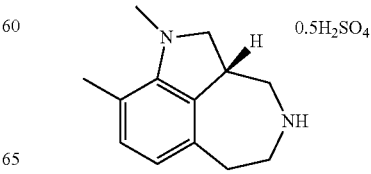

A) tert-butyl(2aR)-1,2,2a,3,5,6-hexahydro-4H-azepino[3,4,5-cd]indole-4-carboxylate tert-Butyl 1,2,2a,3,5,6-hexahydro-4H-azepino[3,4,5-cd]indole-4-carboxylate (3.6 g) was resolved by HPLC (column: CHIRALPAK IC (trade name), 50 mmID×500 mmL, manufactured by Daicel Chemical Industries, mobile phase: hexane/2-propanol=800/200) to give the compound (1.5 g, the title compound) having a shorter retention time.

MS (ESI+): [M+H]$^+$ 275.3.

B) tert-butyl(2aR)-1-methyl-1,2,2a,3,5,6-hexahydro-4H-azepino[3,4,5-cd]indole-4-carboxylate A reaction mixture of tert-butyl(2aR)-1,2,2a,3,5,6-hexahydro-4H-azepino[3,4,5-cd]indole-4-carboxylate (300 mg), aqueous formalin (37 wt %, 256 μL), sodium triacetoxyborohydride (348 mg), acetic acid (188 μL) and acetonitrile (5 mL) was stirred at 0° C. for 1 hr, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (272 mg).

MS (ESI+): [M+H]$^+$ 289.2.

C) tert-butyl(2aR)-7,9-dibromo-1-methyl-1,2,2a,3,5,6-hexahydro-4H-azepino[3,4,5-cd]indole-4-carboxylate To a mixture of tert-butyl(2aR)-1-methyl-1,2,2a,3,5,6-hexahydro-4H-azepino[3,4,5-cd]indole-4-carboxylate (272 mg) and acetonitrile (10 mL) was added N-bromosuccinimide (369 mg) at 0° C. The reaction mixture was stirred at 0° C. for 1 hr, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (274 mg).

MS (ESI+): [M+H]$^+$ 445.0.

D) tert-butyl(2aR)-7-bromo-1,9-dimethyl-1,2,2a,3,5,6-hexahydro-4H-azepino[3,4,5-cd]indole-4-carboxylate To a mixture of tert-butyl(2aR)-7,9-dibromo-1-methyl-1,2,2a,3,5,6-hexahydro-4H-azepino[3,4,5-cd]indole-4-carboxylate (274 mg) and THF (5 mL) was added tert-butyllithium/hexane solution (1.6 M, 811 μL) at −78° C. under argon atmosphere, and the mixture was stirred at −78° C. for 20 min. Methyl iodide (57 μL) was added thereto, and the reaction mixture was stirred at −78° C. under argon atmosphere for 2 hr. Water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (150 mg).

MS (ESI+): [M+H]$^+$ 381.2.

E) tert-butyl(2aR)-1,9-dimethyl-1,2,2a,3,5,6-hexahydro-4H-azepino[3,4,5-cd]indole-4-carboxylate A mixture of tert-butyl(2aR)-7-bromo-1,9-dimethyl-1,2,2a,3,5,6-hexahydro-4H-azepino[3,4,5-cd]indole-4-carboxylate (150 mg), 10% palladium on carbon (20 mg), triethylamine (55 μL) and ethanol (5 mL) was stirred under hydrogen atmosphere for 30 min. The catalyst was removed by filtration, and the solvent was evaporated under reduced pressure. The residue was purified by silica gel column chromatography (ethyl acetate/hexane) to give the title compound (97 mg).

MS (ESI+): [M+H]$^+$ 303.2.

F) (2aS)-1,9-dimethyl-2,2a,3,4,5,6-hexahydro-1H-azepino[3,4,5-cd]indole 0.5 sulfate A reaction mixture of tert-butyl(2aR)-1,9-dimethyl-1,2,2a,3,5,6-hexahydro-4H-azepino[3,4,5-cd]indole-4-carboxylate (97 mg) and 4M hydrogen chloride/ethyl acetate (4 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. To the obtained residue were added ethanol and 1M sulfuric acid (99 μL), and the solvent was evaporated under reduced pressure. The residue was recrystallized from ethanol-IPE to give the title compound (30 mg).

$^1$H NMR (300 MHz, DMSO-d$_6$) δ 2.24 (3H, s), 2.67-2.88 (7H, m), 2.89-3.04 (1H, m), 3.19-3.65 (4H, m), 6.42 (1H, d, J=7.5 Hz), 6.73 (1H, d, J=7.5 Hz), 8.54 (2H, brs).

Example 12

(2aR)-1,9-dimethyl-2,2a,3,4,5,6-hexahydro-1H-azepino[3,4,5-cd]indole 0.5 sulfate

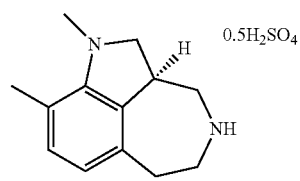

A) tert-butyl(2aS)-1,2,2a,3,5,6-hexahydro-4H-azepino[3,4,5-cd]indole-4-carboxylate tert-Butyl 1,2,2a,3,5,6-hexahydro-4H-azepino[3,4,5-cd]indole-4-carboxylate (3.6 g) was resolved by HPLC (column: CHIRALPAK IC (trade name), 50 mmID×500 mmL, manufactured by Daicel Chemical Industries, mobile phase: hexane/2-propanol=800/200) to give the compound (1.7 g, the title compound) having a longer retention time.

MS (ESI+): [M+H]$^+$ 275.2.

B) (2aR)-1,9-dimethyl-2,2a,3,4,5,6-hexahydro-1H-azepino[3,4,5-cd]indole 0.5 sulfate The title compound was obtained in the same manner as in Steps B-F of Example 11.

Example 13

7-bromo-1-methyl-2,2a,3,4,5,6-hexahydro-1H-azepino[3,4,5-cd]indole hydrochloride

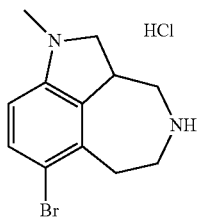

A reaction mixture of tert-butyl 7-bromo-1-methyl-1,2,2a,3,5,6-hexahydro-4H-azepino[3,4,5-cd]indole-4-carboxylate (100 mg) and 4M hydrogen chloride/ethyl acetate (3 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. To the obtained residue were added ethanol and 1M hydrochloric acid (272 μL), and the solvent was evaporated under reduced pressure. The residue was recrystallized from ethanol-IPE to give the title compound (59 mg).

Example 14

7,9-dibromo-1-methyl-2,2a,3,4,5,6-hexahydro-1H-azepino[3,4,5-cd]indole hydrochloride

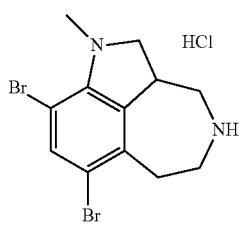

The title compound was obtained from tert-butyl 7,9-dibromo-1-methyl-1,2,2a,3,5,6-hexahydro-4H-azepino[3,4,5-cd]indole-4-carboxylate in the same manner as in Example 13.

Example 15

1-isopropyl-2,2a,3,4,5,6-hexahydro-1H-azepino[3,4,5-cd]indole hydrochloride

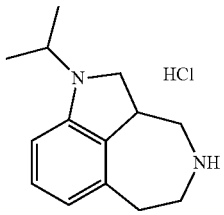 [SMILES: CC(C)N1CC2CNCCc3cccc1c32 ; Cl]

A) tert-butyl 1-isopropyl-1,2,2a,3,5,6-hexahydro-4H-azepino[3,4,5-cd]indole-4-carboxylate The title compound was obtained from tert-butyl 1,2,2a,3,5,6-hexahydro-4H-azepino[3,4,5-cd]indole-4-carboxylate and acetone in the same manner as in Step A of 5 Example 4.

MS (ESI+): [M+H]$^+$ 317.2.

B) 1-isopropyl-2,2a,3,4,5,6-hexahydro-1H-azepino[3,4,5-cd]indole hydrochloride

The title compound was obtained in the same manner as in Step B of Example 6.

EXAMPLE 16

9-chloro-1-isopropyl-2,2a,3,4,5,6-hexahydro-1H-azepino[3,4,5-cd]indole hydrochloride

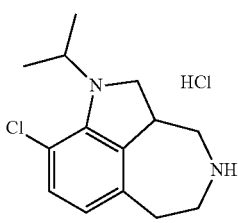 [SMILES: CC(C)N1CC2CNCCc3ccc(Cl)c1c32 ; Cl]

The title compound was obtained from tert-butyl 1-isopropyl-1,2,2a,3,5,6-hexahydro-4H-azepino[3,4,5-cd]indole-4-carboxylate in the same manner as in Steps A-D of Example 5.

Example 17

(2aS)-9-chloro-1-isopropyl-2,2a,3,4,5,6-hexahydro-1H-azepino[3,4,5-cd]indole hydrochloride

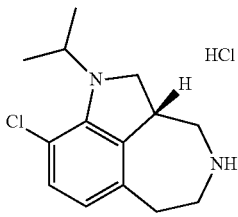 [SMILES: CC(C)N1C[C@@H]2CNCCc3ccc(Cl)c1c32 ; Cl]

A) tert-butyl(2aR)-1-isopropyl-1,2,2a,3,5,6-hexahydro-4H-azepino[3,4,5-cd]indole-4-carboxylate A reaction mixture of tert-butyl(2aR)-1,2,2a,3,5,6-hexahydro-4H-azepino[3,4,5-cd]indole-4-carboxylate (500 mg), acetone (201 μL), sodium triacetoxyborohydride (579 mg), acetic acid (313 μL) and acetonitrile (10 mL) was stirred at 0° C. for 1 hr, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (473 mg).

MS (ESI+): [M+H]$^+$ 317.2.

B) tert-butyl(2aR)-7-bromo-1-isopropyl-1,2,2a,3,5,6-hexahydro-4H-azepino[3,4,5-cd]indole-4-carboxylate To a mixture of tert-butyl(2aR)-1-isopropyl-1,2,2a,3,5,6-hexahydro-4H-azepino[3,4,5-cd]indole-4-carboxylate (473 mg) and acetonitrile (10 mL) was added N-bromosuccinimide (266 mg). The reaction mixture was stirred for 3 hr, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (528 mg).

MS (ESI+): [M+H]$^+$ 395.2.

C) tert-butyl(2aR)-7-bromo-9-chloro-1-isopropyl-1,2,2a,3,5,6-hexahydro-4H-azepino[3,4,5-cd]indole-4-carboxylate To a mixture of tert-butyl(2aR)-7-bromo-1-isopropyl-1,2,2a,3,5,6-hexahydro-4H-azepino[3,4,5-cd]indole-4-carboxylate (473 mg) and acetonitrile (10 mL) was added N-chlorosuccinimide (176 mg) at room temperature. The reaction mixture was stirred overnight at 35° C. under nitrogen atmosphere, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (188 mg).

$^1$H NMR (300 MHz, CDCl$_3$) δ 1.08-1.20 (6H, m), 1.49 (9H, s), 2.50-3.05 (4H, m), 3.27-3.35 (1H, m), 3.50-3.75 (2H, m), 4.05-4.30 (2H, m), 4.71 (1H, brs), 7.23 (1H, s).

D) tert-butyl(2aR)-9-chloro-1-isopropyl-1,2,2a,3,5,6-hexahydro-4H-azepino[3,4,5-cd]indole-4-carboxylate To a mixture of tert-butyl(2aR)-7-bromo-9-chloro-1-isopropyl-1,2,2a,3,5,6-hexahydro-4H-azepino[3,4,5-cd]indole-4-carboxylate (188 mg) and THF (5 mL) was added tert-butyllithium/hexane solution (1.6 M, 386 μL) at −78° C. under argon atmosphere. The reaction mixture was stirred at −78° C. for 30 min, water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (88 mg).

MS (ESI+): [M+H]$^+$ 351.2.

E) (2aS)-9-chloro-1-isopropyl-2,2a,3,4,5,6-hexahydro-1H-azepino[3,4,5-cd]indole hydrochloride A reaction mixture of tert-butyl(2aR)-9-chloro-1-isopropyl-1,2,2a,3,5,6-hexahydro-4H-azepino[3,4,5-cd]indole-4-carboxylate (88 mg) and 4M hydrogen chloride/ethyl acetate (2 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. To the obtained residue were added ethanol and 1M hydrochloric acid (250 μL), and the solvent was evaporated under reduced pressure. The residue was recrystallized from ethanol-IPE to give the title compound (50 mg).

$^1$H NMR (300 MHz, DMSO-d$_6$) δ 1.06 (3H, d, J=6.8 Hz), 1.12 (3H, d, J=6.8 Hz), 2.76-3.22 (5H, m), 3.32-3.84 (4H, m), 4.64 (1H, quin, J=6.6 Hz), 6.50 (1H, d, J=7.9 Hz), 6.97 (1H, d, J=7.9 Hz), 9.00-9.48 (2H, m).

Example 18

(2aR)-9-chloro-1-isopropyl-2,2a,3,4,5,6-hexahydro-1H-azepino[3,4,5-cd]indole hydrochloride

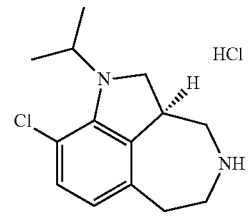 [SMILES: CC(C)N1C[C@H]2CNCCc3ccc(Cl)c1c32 ; Cl]

The title compound was obtained from tert-butyl(2aS)-1,2,2a,3,5,6-hexahydro-4H-azepino[3,4,5-cd]indole-4-carboxylate in the same manner as in Steps A-E of Example 17.

Example 19

1-benzyl-2,2a,3,4,5,6-hexahydro-1H-azepino[3,4,5-cd]indole hydrochloride

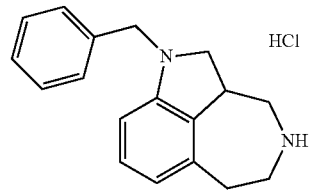 [SMILES: c1ccc(CN2CC3CNCCc4cccc2c43)cc1 ; Cl]

A) tert-butyl 1-benzyl-1,2,2a,3,5,6-hexahydro-4H-azepino[3,4,5-cd]indole-4-carboxylate The title compound was obtained from tert-butyl 1,2,2a,3,5,6-hexahydro-4H-azepino[3,4,5-cd]indole-4-carboxylate and benzaldehyde in the same manner as in Step A of Example 4.

MS (ESI+): [M+H]$^+$ 365.2.

B) 1-benzyl-2,2a,3,4,5,6-hexahydro-1H-azepino[3,4,5-cd]indole hydrochloride

The title compound was obtained in the same manner as in Step B of Example 6.

EXAMPLE 20

1-(2,2a,3,4,5,6-hexahydro-1H-azepino[3,4,5-cd]indol-1-yl)ethanone hydrochloride

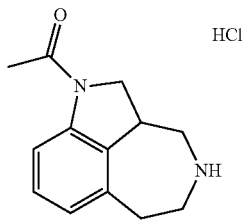 [SMILES: CC(=O)N1CC2CNCCc3cccc1c32 ; Cl]

A) tert-butyl 1-acetyl-1,2,2a,3,5,6-hexahydro-4H-azepino[3,4,5-cd]indole-4-carboxylate A reaction mixture of tert-butyl 1,2,2a,3,5,6-hexahydro-4H-azepino[3,4,5-cd]indole-4-carboxylate (300 mg), acetyl chloride (117 μL) and DMA (3 mL) was stirred at room temperature for 16 hr, water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (281 mg).

$^1$H NMR (300 MHz, CDCl$_3$) δ 1.51 (9H, s), 2.13-2.46 (3H, m), 2.60-3.13 (4H, m), 3.43-3.60 (1H, m), 3.73 (1H, brs), 4.22 (3H, t, J=10.4 Hz), 6.81 (1H, d, J=7.9 Hz), 7.12 (1H, dd, J=7.9 Hz), 8.10 (1H, d, J=7.9 Hz).

B) 1-(2,2a,3,4,5,6-hexahydro-1H-azepino[3,4,5-cd]indol-1-yl)ethanone hydrochloride A reaction mixture of tert-butyl 1-acetyl-1,2,2a,3,5,6-hexahydro-4H-azepino[3,4,5-cd]indole-4-carboxylate (281 mg), 4M hydrogen chloride/ethyl acetate (5 mL) and ethanol (3 mL) was stirred at room temperature for 2 hr, and the solvent was evaporated under reduced pressure. The residue was recrystallized from methanol-ethanol-IPE to give the title compound (211 mg).

Example 21

1-(9-chloro-2,2a,3,4,5,6-hexahydro-1H-azepino[3,4,5-cd]indol-1-yl)ethanone hydrochloride

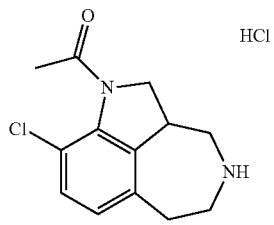 [SMILES: CC(=O)N1CC2CNCCc3ccc(Cl)c1c32 ; Cl]

A) tert-butyl 1-acetyl-9-chloro-1,2,2a,3,5,6-hexahydro-4H-azepino[3,4,5-cd]indole-4-carboxylate A reaction mixture of tert-butyl 1-acetyl-1,2,2a,3,5,6-hexahydro-4H-azepino[3,4,5-cd]indole-4-carboxylate (120 mg), palladium(II) acetate (4 mg), N-chlorosuccinimide (76 mg) and acetic acid (2 mL) was stirred at 100° C. under nitrogen atmosphere for 5 hr, basified with aqueous sodium bicarbonate, and extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (16 mg).

$^1$H NMR (300 MHz, CDCl$_3$) δ 1.50 (9H, s), 2.26 (3H, s), 2.49-3.13 (4H, m), 3.29-3.54 (1H, m, J=12.1 Hz), 3.60-3.86 (1H, m), 4.02-4.64 (3H, m), 6.84 (1H, d, J=7.2 Hz), 7.13 (1H, d, J=8.3 Hz).

B) 1-(9-chloro-2,2a,3,4,5,6-hexahydro-1H-azepino[3,4,5-cd]indol-1-yl)ethanone hydrochloride The title compound was obtained in the same manner as in Step B of Example 20.

Example 22

1-(7-chloro-2,2a,3,4,5,6-hexahydro-1H-azepino[3,4,5-cd]indol-1-yl)ethanone hydrochloride

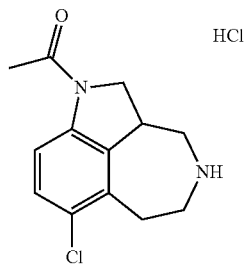 [SMILES: CC(=O)N1CC2CNCCc3c(Cl)ccc1c32 ; Cl]

A) tert-butyl 1-acetyl-7-chloro-1,2,2a,3,5,6-hexahydro-4H-azepino[3,4,5-cd]indole-4-carboxylate A reaction mixture of tert-butyl 1-acetyl-1,2,2a,3,5,6-hexahydro-4H-azepino[3,4,5-cd]indole-4-carboxylate (120 mg), palladium(II) acetate (4 mg), N-chlorosuccinimide (76 mg) and acetic acid (2 mL) was stirred at 100° C. under nitrogen atmosphere for 5 hr, basified with aqueous sodium bicarbonate, and extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (63 mg).

$^1$H NMR (300 MHz, CDCl$_3$) δ 1.50 (9H, s), 2.19-2.45 (3H, m), 2.64-3.06 (3H, m), 3.47 (1H, dd, J=16.0, 5.5 Hz), 3.54-3.62 (1H, m), 3.74 (1H, d, J=10.2 Hz), 4.04-4.34 (3H, m), 7.22 (1H, d, J=8.7 Hz), 8.04 (1H, d, J=8.7 Hz).

B) 1-(7-chloro-2,2a,3,4,5,6-hexahydro-1H-azepino[3,4,5-cd]indol-1-yl)ethanone hydrochloride The title compound was obtained in the same manner as in Step B of Example 20.

Example 23

1-(7,9-dichloro-2,2a,3,4,5,6-hexahydro-1H-azepino[3,4,5-cd]indol-1-yl)ethanone

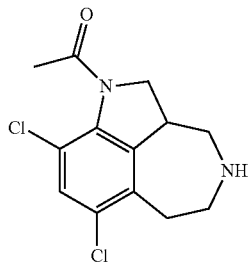 [SMILES: CC(=O)N1CC2CNCCc3c(Cl)cc(Cl)c1c32]

A) tert-butyl 1-acetyl-7,9-dichloro-1,2,2a,3,5,6-hexahydro-4H-azepino[3,4,5-cd]indole-4-carboxylate A reaction mixture of tert-butyl 1-acetyl-1,2,2a,3,5,6-hexahydro-4H-azepino[3,4,5-cd]indole-4-carboxylate (288 mg), palladium(II) acetate (10 mg), N-chlorosuccinimide (182 mg) and acetic acid (5 mL) was stirred overnight at 100° C. under nitrogen atmosphere, basified with aqueous sodium bicarbonate, and extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (17 mg).

$^1$H NMR (300 MHz, CDCl$_3$) δ 1.50 (9H, s), 2.29 (3H, s), 2.57-2.90 (2H, m, J=11.7 Hz), 2.91-3.08 (1H, m), 3.30-3.61 (2H, m, J=16.4, 5.1 Hz), 3.77 (1H, brs), 4.04-4.33 (2H, m), 4.39-4.60 (1H, m), 7.31 (1H, s).

B) 1-(7,9-dichloro-2,2a,3,4,5,6-hexahydro-1H-azepino[3,4,5-cd]indol-1-yl)ethanone A reaction mixture of tert-butyl 1-acetyl-7,9-dichloro-1,2,2a,3,5,6-hexahydro-4H-azepino[3,4,5-cd]indole-4-carboxylate (17 mg) and 4M hydrogen chloride/ethyl acetate (2 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. The residue was purified by HPLC (C18, mobile phase: water/acetonitrile (containing 0.1% TFA)), to the obtained fraction was added saturated aqueous sodium bicarbonate solution, and the mixture was extracted with ethyl acetate. The extract was dried over anhydrous magnesium sulfate, filtered, and concentrated under reduced pressure to give the title compound (4 mg).

Example 24

1-((2aS)-9-chloro-2,2a,3,4,5,6-hexahydro-1H-azepino[3,4,5-cd]indol-1-yl)ethanone hydrochloride

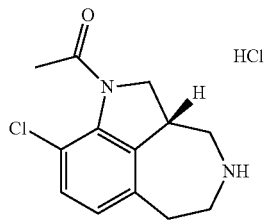 [SMILES: CC(=O)N1C[C@@H]2CNCCc3ccc(Cl)c1c32 ; Cl]

A) tert-butyl(2aR)-1-acetyl-1,2,2a,3,5,6-hexahydro-4H-azepino[3,4,5-cd]indole-4-carboxylate A reaction mixture of tert-butyl(2aR)-1,2,2a,3,5,6-hexahydro-4H-azepino[3,4,5-cd]indole-4-carboxylate (300 mg), acetyl chloride (93 μL) and DMA (5 mL) was stirred at room temperature for 16 hr, water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (327 mg).

$^1$H NMR (300 MHz, CDCl$_3$) δ 1.50 (9H, s), 2.08-2.48 (3H, m), 2.60-3.16 (4H, m), 3.38-3.60 (1H, m), 3.73 (1H, brs), 4.06-4.59 (3H, m), 6.81 (1H, d, J=7.2 Hz), 7.12 (1H, t, J=7.7 Hz), 8.10 (1H, d, J=7.9 Hz).

B) tert-butyl(2aR)-1-acetyl-9-chloro-1,2,2a,3,5,6-hexahydro-4H-azepino[3,4,5-cd]indole-4-carboxylate A reaction mixture of tert-butyl(2aR)-1-acetyl-1,2,2a,3,5,6-hexahydro-4H-azepino[3,4,5-cd]indole-4-carboxylate (326 mg), palladium(II) acetate (230 mg), N-chlorosuccinimide (179 mg) and acetic acid (10 mL) was stirred at 75° C. under nitrogen atmosphere for 5 hr, basified with saturated aqueous sodium bicarbonate solution, and extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (46 mg).

$^1$H NMR (300 MHz, CDCl$_3$) δ 1.50 (9H, s), 2.26 (3H, s), 2.50-3.08 (4H, m), 3.26-3.51 (1H, m), 3.75 (1H, brs), 4.03-4.61 (3H, m), 6.84 (1H, d, J=7.2 Hz), 7.13 (1H, d, J=8.3 Hz).

C) 1-((2aS)-9-chloro-2,2a,3,4,5,6-hexahydro-1H-azepino[3,4,5-cd]indol-1-yl)ethanone hydrochloride A reaction mixture of tert-butyl(2aR)-1-acetyl-9-chloro-1,2,2a,3,5,6-hexahydro-4H-azepino[3,4,5-cd]indole-4-carboxylate (46 mg) and 4M hydrogen chloride/ethyl acetate (2 mL) was stirred at room temperature for 2 hr, and the solvent was evaporated under reduced pressure. The residue was recrystallized from ethanol-heptane to give the title compound (20 mg).
$^1$H NMR (300 MHz, DMSO-$d_6$) δ 2.19 (3H, s), 2.98 (3H, dd, J=15.8, 5.7 Hz), 3.19 (1H, d, J=13.9 Hz), 3.39-3.66 (3H, m), 3.94-4.20 (1H, m), 4.46 (1H, dd, J=10.7, 8.9 Hz), 6.99 (1H, d, J=8.3 Hz), 7.23 (1H, d, J=8.3 Hz), 9.44 (2H, brs).

Example 25

1-((2aR)-9-chloro-2,2a,3,4,5,6-hexahydro-1H-azepino[3,4,5-cd]indol-1-yl)ethanone hydrochloride

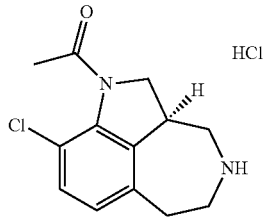 [SMILES: CC(=O)N1C[C@H]2CNCCc3ccc(Cl)c1c32 ; Cl]

The title compound was synthesized from tert-butyl(2aS)-1-acetyl-9-chloro-1,2,2a,3,5,6-hexahydro-4H-azepino[3,4,5-cd]indole-4-carboxylate in the same manner as in Steps A-C of Example 24.

Example 26

9-chloro-2,2a,3,4,5,6-hexahydro-1H-azepino[3,4,5-cd]indole

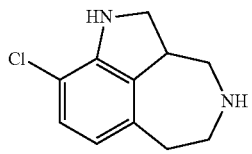 [SMILES: Clc1ccc2c3c1NCC3CNCC2]

A) tert-butyl 9-chloro-1,2,2a,3,5,6-hexahydro-4H-azepino[3,4,5-cd]indole-4-carboxylate A reaction mixture of tert-butyl 1-acetyl-9-chloro-1,2,2a,3,5,6-hexahydro-4H-azepino[3,4,5-cd]indole-4-carboxylate (14 mg), THF (2 mL) and 1M aqueous sodium hydroxide solution was stirred overnight at room temperature. To the reaction mixture was added water, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (6 mg).
$^1$H NMR (300 MHz, CDCl$_3$) b 1.49 (9H, s), 2.58-3.09 (4H, m), 3.09-3.27 (1H, m), 3.75 (2H, brs), 3.97 (1H, brs), 4.26 (2H, brs), 6.41 (1H, d, J=6.8 Hz), 6.92 (1H, d, J=8.3 Hz).

B) 9-chloro-2,2a,3,4,5,6-hexahydro-1H-azepino[3,4,5-cd]indole

The title compound was obtained in the same manner as in Step B of Example 20.

Example 27

(2aS)-9-chloro-2,2a,3,4,5,6-hexahydro-1H-azepino[3,4,5-cd]indole dihydrochloride

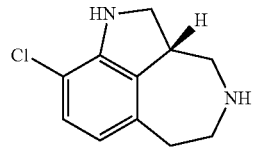

A) di-tert-butyl(2aS)-9-chloro-2a,3,5,6-tetrahydro-1H-azepino[3,4,5-cd]indole-1,4(2H)-dicarboxylate A reaction mixture of tert-butyl(2aR)-1,2,2a,3,5,6-hexahydro-4H-azepino[3,4,5-cd]indole-4-carboxylate (760 mg), triethylamine (579 μL), Boc$_2$O (907 mg), DMAP (34 mg) and DMA was stirred overnight at room temperature. To the reaction mixture was added water, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (360 mg).
$^1$H NMR (300 MHz, CDCl$_3$) δ 1.50 (9H, s), 1.56 (9H, s), 2.62-3.13 (4H, m), 3.34-3.49 (1H, m), 3.61 (1H, brs), 4.04-4.49 (3H, m), 6.72 (1H, d, J=7.5 Hz), 7.08 (1H, dd, J=7.7 Hz), 7.37-7.85 (1H, m).

B) (2aS)-9-chloro-2,2a,3,4,5,6-hexahydro-1H-azepino[3,4,5-cd]indole dihydrochloride The title compound was obtained in the same manner as in Steps B-D of Example 17 and Step B of Example 20.

Example 28

(2aS)-1-benzyl-9-chloro-2,2a,3,4,5,6-hexahydro-1H-azepino[3,4,5-cd]indole hydrochloride

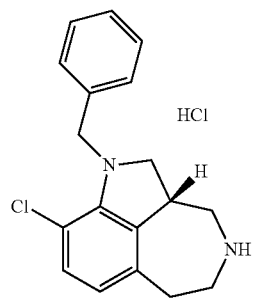

A) tert-butyl(2aR)-9-chloro-1,2,2a,3,5,6-hexahydro-4H-azepino[3,4,5-cd]indole-4-carboxylate A reaction mixture of (2aS)-9-chloro-2,2a,3,4,5,6-hexahydro-1H-azepino[3,4,5-cd]indole dihydrochloride (525 mg), Boc$_2$O (433 μL), ethyl acetate and saturated aqueous sodium bicarbonate solution was stirred overnight at room temperature. To the reaction mixture was added water, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (472 mg).

$^1$H NMR (300 MHz, CDCl$_3$) δ 1.49 (9H, s), 2.52-3.08 (4H, m), 3.17 (1H, brs), 3.76 (2H, brs), 3.95 (1H, brs), 4.04-4.47 (2H, m), 6.41 (1H, d, J=7.5 Hz), 6.92 (1H, d, J=8.3 Hz).

B) tert-butyl(2aR)-1-benzyl-9-chloro-1,2,2a,3,5,6-hexahydro-4H-azepino[3,4,5-cd]indole-4-carboxylate To a mixture of tert-butyl(2aR)-9-chloro-1,2,2a,3,5,6-hexahydro-4H-azepino[3,4,5-cd]indole-4-carboxylate (50 mg), benzyl bromide (29 μL) and DMF (2 mL) was added sodium hydride (60%, 8 mg). The reaction mixture was stirred at room temperature under nitrogen atmosphere for 2 hr. To the reaction mixture was added water, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (40 mg).

MS (ESI+): [M+H]$^+$ 399.2.

C) (2aS)-1-benzyl-9-chloro-2,2a,3,4,5,6-hexahydro-1H-azepino[3,4,5-cd]indole hydrochloride A reaction mixture of tert-butyl(2aR)-1-benzyl-9-chloro-1,2,2a,3,5,6-hexahydro-4H-azepino[3,4,5-cd]indole-4-carboxylate (40 mg) and 4M hydrogen chloride/ethyl acetate (2 mL) was stirred overnight at room temperature, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. The residue was purified by HPLC (C18, mobile phase: water/acetonitrile (5 mM, containing AcONH$_4$)). To the obtained residue (26 mg) were added ethanol and 1M hydrochloric acid (91 μL), and the solvent was evaporated under reduced pressure. The residue was recrystallized from ethanol-IPE to give the title compound (15 mg).

Example 29

(2aS)-9-chloro-1-ethyl-2,2a,3,4,5,6-hexahydro-1H-azepino[3,4,5-cd]indole hydrochloride

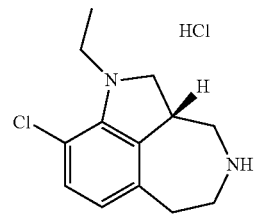 [SMILES: CCN1C[C@@H]2CNCCc3ccc(Cl)c1c32 ; Cl]

A) tert-butyl(2aR)-1-ethyl-1,2,2a,3,5,6-hexahydro-4H-azepino[3,4,5-cd]indole-4-carboxylate A reaction mixture of tert-butyl(2aR)-1,2,2a,3,5,6-hexahydro-4H-azepino[3,4,5-cd]indole-4-carboxylate (151 mg), ethyl iodide (66 μL), triethylamine (115 μL) and DMA (5 mL) was stirred overnight at 50° C., water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (124 mg).

MS (ESI+): [M+H]$^+$ 303.2.

B) tert-butyl(2aR)-7-bromo-1-ethyl-1,2,2a,3,5,6-hexahydro-4H-azepino[3,4,5-cd]indole-4-carboxylate To a mixture of tert-butyl(2aR)-1-ethyl-1,2,2a,3,5,6-hexahydro-4H-azepino[3,4,5-cd]indole-4-carboxylate (150 mg) and acetonitrile (5 mL) was added N-bromosuccinimide (266 mg) at 0° C. The reaction mixture was stirred at room temperature for 2 hr, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (168 mg).

MS (ESI+): [M+H]$^+$ 381.1.

C) tert-butyl(2aR)-7-bromo-9-chloro-1-ethyl-1,2,2a,3,5,6-hexahydro-4H-azepino[3,4,5-cd]indole-4-carboxylate To a mixture of tert-butyl(2aR)-7-bromo-1-ethyl-1,2,2a,3,5,6-hexahydro-4H-azepino[3,4,5-cd]indole-4-carboxylate (473 mg) and acetonitrile (10 mL) was added N-chlorosuccinimide (65 mg) at room temperature. The reaction mixture was stirred overnight at 40° C. under nitrogen atmosphere, saturated aqueous sodium bicarbonate solution was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (109 mg).

MS (ESI+): [M+H]$^+$ 415.1.

D) tert-butyl(2aR)-9-chloro-1-ethyl-1,2,2a,3,5,6-hexahydro-4H-azepino[3,4,5-cd]indole-4-carboxylate To a mixture of tert-butyl(2aR)-7-bromo-9-chloro-1-ethyl-1,2,2a,3,5,6-hexahydro-4H-azepino[3,4,5-cd]indole-4-carboxylate (109 mg) and THF (3 mL) was added tert-butyllithium/hexane solution (1.6 M, 231 μL) at −78° C. under argon atmosphere. The reaction mixture was stirred at −78° C. for 20 min, water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (51 mg).

MS (ESI+): [M+H]$^+$ 337.1.

E) (2aS)-9-chloro-1-ethyl-2,2a,3,4,5,6-hexahydro-1H-azepino[3,4,5-cd]indole hydrochloride A reaction mixture of tert-butyl(2aR)-9-chloro-1-ethyl-1,2,2a,3,5,6-hexahydro-4H-azepino[3,4,5-cd]indole-4-carboxylate (40 mg) and 4M hydrogen chloride/ethyl acetate (3 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. The residue was purified by HPLC (C18, mobile phase: water/acetonitrile (5 mM, containing AcONH$_4$)). To the obtained residue were added ethanol and 1M hydrochloric acid, and the solvent was evaporated under reduced pressure. The residue was recrystallized from ethanol-IPE to give the title compound (21 mg).

$^1$H NMR (300 MHz, DMSO-d$_6$) δ 1.06 (3H, t, J=7.0 Hz), 2.67-3.17 (5H, m), 3.32-3.60 (4H, m), 3.67-3.83 (2H, m), 6.49 (1H, =8.3 Hz), 6.97 (1H, d, J=8.3 Hz), 9.01 (1H, brs), 9.24 (1H, brs).

Example 30

(2aS)-9-chloro-1-cyclopropyl-2,2a,3,4,5,6-hexahydro-1H-azepino[3,4,5-cd]indole

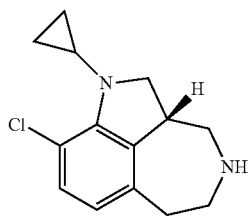 [SMILES: Clc1ccc2c3c1N(C1CC1)C[C@@H]3CNCC2]

A) tert-butyl(2aR)-1-cyclopropyl-1,2,2a,3,5,6-hexahydro-4H-azepino[3,4,5-cd]indole-4-carboxylate A reaction mixture of tert-butyl(2aR)-1,2,2a,3,5,6-hexahydro-4H-azepino[3,4,5-cd]indole-4-carboxylate (200 mg), copper(II) acetate (132 mg), 2,2'-bipyridyl (114 mg), sodium carbonate (155 mg), cyclopropylboronic acid (125 mg) and acetonitrile (5 mL) was stirred at 70° C. under air atmosphere for 5 hr. To the reaction mixture was added water, and the insoluble substance was removed by filtration through Celite. To the filtrate was added water, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (91 mg).

$^1$H NMR (300 MHz, CDCl$_3$) δ 0.50-0.61 (2H, m), 0.62-0.71 (1H, m, J=8.3, 4.1, 4.1 Hz), 0.77 (1H, brs), 1.48 (9H, s), 2.08-2.18 (1H, m), 2.57-3.11 (5H, m), 3.38-3.67 (2H, m), 4.05-4.41 (2H, m), 6.42-6.56 (1H, m), 6.70 (1H, d, J=7.9 Hz), 6.92-7.06 (1H, m).

B) tert-butyl(2aR)-9-chloro-1-cyclopropyl-1,2,2a,3,5,6-hexahydro-4H-azepino[3,4,5-cd]indole-4-carboxylate The title compound was obtained in the same manner as in Steps B-D of Example 17.

C) (2aS)-9-chloro-1-cyclopropyl-2,2a,3,4,5,6-hexahydro-1H-azepino[3,4,5-cd]indole A reaction mixture of tert-butyl(2aR)-9-chloro-1-cyclopropyl-1,2,2a,3,5,6-hexahydro-4H-azepino[3,4,5-cd]indole-4-carboxylate (10 mg) and 4M hydrogen chloride/ethyl acetate (2 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. The residue was purified by HPLC (C18, mobile phase: water/acetonitrile (5 mM, containing AcONH$_4$)) to give the title compound (3 mg).

Example 31

3,4,5,6-tetrahydrofuro[4,3,2-ef][3]benzazepine hydrochloride

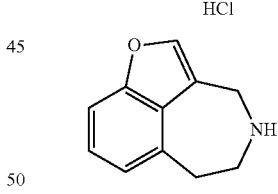

A) 3-methyl-1-benzofuran-4-carbaldehyde

To a mixture of 1-(3-bromophenoxyl)acetone (40.2 g) and toluene (439 mL) was added polyphosphoric acid (39.6 g). The reaction mixture was refluxed with vigorously stirring for 17 hr. The mixture was allowed to be cooled to room temperature, poured into ice water, and extracted with ethyl acetate. The extract was washed with saturated aqueous sodium bicarbonate solution, dried over anhydrous sodium sulfate, and filtered, and the solvent was evaporated under reduced pressure. The residue was purified by silica gel column chromatography (ethyl acetate/hexane) to give a mixture (32.2 g) of 4-bromo-3-methyl-1-benzofuran and 6-bromo-3-methyl-1-benzofuran. The obtained mixture (30 g) was diluted with ether (632 mL), and tert-butyllithium/ hexane solution (1.7 M, 209 mL) was added thereto at −78° C. under argon atmosphere. The reaction mixture was stirred at −78° C. for 40 min, and DMF (36.4 g) was added thereto. The reaction mixture was warmed to 0° C. over 1 hr, and water was added thereto. The mixture was extracted with ethyl acetate, the extract was washed with saturated brine, dried over anhydrous sodium sulfate, and filtered, and the solvent was evaporated under reduced pressure. The residue was purified by silica gel column chromatography (ethyl acetate/hexane) to give the title compound (12 g).

$^1$H NMR (400 MHz, CDCl$_3$) δ 2.37 (3H, d, J=1.2 Hz), 7.27 (1H, t, J=8.0 Hz), 7.43 (1H, d, J=0.8 Hz), 7.55 (1H, dd, J=8.4, 0.8 Hz), 7.69 (1H, d, J=7.0 Hz), 10.31 (1H, s).

B) 3-methyl-4-(2-nitrovinyl)-1-benzofuran

To a mixture of 3-methyl-1-benzofuran-4-carbaldehyde (12 g) and nitromethane (102 mL) was added ammonium acetate (1.7 g). The reaction mixture was refluxed for 4 hr, and allowed to be cooled to room temperature, and the solvent was evaporated under reduced pressure. The residue was purified by silica gel column chromatography (ethyl acetate/hexane) to give the title compound (11 g).

$^1$H NMR (400 MHz, CDCl$_3$) δ 2.48 (3H, d, J=1.2 Hz), 7.32 (1H, t, J=8.0 Hz), 7.50 (1H, d, J=7.6 Hz), 7.53 (1H, d, J=1.2 Hz), 7.58 (1H, d, J=8.0 Hz), 7.63 (1H, d, J=13.2 Hz), 8.67 (1H, d, J=13.6 Hz).

C) tert-butyl(2-(3-methyl-1-benzofuran-4-yl)ethyl)carbamate

To a mixture of lithium aluminium hydride (13 g) and ether (70 mL) was added dropwise a mixture of 3-methyl-4-(2-nitrovinyl)-1-benzofuran (11 g) and ether (347 mL) at 0° C. The reaction mixture was stirred at room temperature for 2 hr, and a large excess of sodium sulfate decahydrate was added thereto at 0° C. The mixture was stirred at room temperature for 30 min, the insoluble substance was removed by filtration through Celite, and the Celite was washed with ethyl acetate. The solvent of the filtrate was evaporated under reduced pressure. The residue was diluted with THF (139 mL), and Boc$_2$O (13 mL) was added thereto. The reaction mixture was stirred at room temperature for 1 hr, and the solvent was evaporated under reduced pressure. The residue was purified by silica gel column chromatography (ethyl acetate/hexane) to give the title compound (12 g).

$^1$H NMR (400 MHz, CDCl$_3$) δ 1.43 (9H, s), 2.39 (3H, d, J=1.6 Hz), 3.15 (2H, t, J=6.8 Hz), 3.42-3.47 (2H, m), 4.59 (1H, brs), 6.99 (1H, d, J=7.2 Hz), 7.20 (1H, t, J=7.8 Hz), 7.33 (1H, d, J=8.4 Hz), 7.37 (1H, d, J=1.2 Hz).

D) tert-butyl(2-(3-(hydroxymethyl)-1-benzofuran-4-yl)ethyl)carbamate

A reaction mixture of tert-butyl(2-(3-methyl-1-benzofuran-4-yl)ethyl)carbamate (12 g), selenium dioxide (5.5 g) and dioxane (108 mL) was refluxed for 12.5 hr. The mixture was allowed to be cooled to room temperature, the insoluble substance was removed by filtration through Celite, and the Celite was washed with ethyl acetate. The solvent of the filtrate was evaporated under reduced pressure, and the residue was purified by silica gel column chromatography (ethyl acetate/hexane) to give the title compound (5.4 g).

$^1$H NMR (400 MHz, CDCl$_3$) δ 1.44 (9H, s), 3.17-3.21 (2H, m), 3.40-3.45 (2H, m), 3.64 (1H, brs), 4.84-4.94 (3H, m), 7.04 (1H, d, J=7.2 Hz), 7.23 (1H, t, J=7.8 Hz), 7.36 (1H, d, J=8.0 Hz), 7.61 (1H, s).

E) tert-butyl 5,6-dihydrofuro[4,3,2-ef][3]benzazepine-4(3H)-carboxylate

To a mixture of tert-butyl(2-(3-(hydroxymethyl)-1-benzofuran-4-yl)ethyl)carbamate (5.4 g), triethylamine (10.2 mL) and dichloromethane (21 mL) was added dropwise a mixture of sulfur trioxide pyridine complex (8.8 g) and DMSO (19.6 mL) at 0° C. The reaction mixture was stirred at 0° C. for 1 hr, and diluted with dichloromethane. The mixture was washed with water, 10% aqueous tartaric acid and saturated brine, dried over anhydrous sodium sulfate, and filtered, and the solvent was evaporated under reduced pressure. The residue (5.3 g) was diluted with dichloromethane (45.4 mL), and a mixture of trifluoroacetic acid (14 mL) and dichloromethane (15.1 mL) was added dropwise thereto at −10° C. The mixture was stirred at room temperature for 30 min, and the solvent was evaporated under reduced pressure. The residue was diluted with dichloromethane (182 mL), and acetic acid (1.6 mL) and sodium triacetoxyborohydride (7.7 g) were added thereto at room temperature. The reaction mixture was stirred at room temperature for 1 hr, and the pH of the mixture was adjusted to 8-9 with 2M aqueous sodium hydroxide solution under ice-cooling. To the reaction mixture was added Boc$_2$O (4.2 mL), and the mixture was stirred at room temperature for 30 min. The organic layer was separated, and the aqueous layer was extracted with dichloromethane. The combined organic layers were washed with saturated aqueous sodium bicarbonate solution, dried over anhydrous sodium sulfate, and filtered, and the solvent was evaporated under reduced pressure. The residue was purified by silica gel column chromatography (ethyl acetate/hexane) to give the title compound (4.2 g).

$^1$H NMR (400 MHz, CDCl$_3$) 51.43 and 1.47 (9H, each s), 3.26-3.33 (2H, m), 3.76-3.82 (2H, m), 4.71 and 4.76 (2H, each s), 7.00-7.06 (1H, m), 7.21 (1H, t, J=7.8 Hz), 7.31-7.33 (1H, m), 7.44-7.48 (1H, m).

F) 3,4,5,6-tetrahydrofuro[4,3,2-ef][3]benzazepine hydrochloride

The title compound was obtained in the same manner as in Example 13.

Example 32

2,2a,3,4,5,6-hexahydrofuro[4,3,2-ef][3]benzazepine hydrochloride

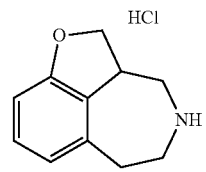 [SMILES: Cl ; c1cc2c3c(c1)OCC3CNCC2]

A) tert-butyl 2a,3,5,6-tetrahydrofuro[4,3,2-ef][3]benzazepine-4(2H)-carboxylate

A reaction mixture of tert-butyl 5,6-dihydrofuro[4,3,2-ef][3]benzazepine-4(3H)-carboxylate (1.0 g), 10% palladium on carbon (195 mg) and ethyl acetate was stirred at room temperature under hydrogen atmosphere for 24 hr. The insoluble substance was removed by filtration through Celite, and the Celite was washed with ethyl acetate. The solvent of the filtrate was evaporated under reduced pressure to give the title compound (1.0 g).

$^1$H NMR (400 MHz, CDCl$_3$) 51.50 (9H, s), 2.70-3.12 (4H, m), 3.70-3.90 (1H, m), 4.00 (1H, t, J=9.6 Hz), 4.10-4.48 (2H, m), 4.71 (1H, t, J=9.2 Hz), 6.62-6.65 (2H, m), 7.03 (1H, t, J=7.8 Hz).

B) 2,2a,3,4,5,6-hexahydrofuro[4,3,2-ef][3]benzazepine hydrochloride

The title compound was obtained in the same manner as in Example 13.

Example 33

9-chloro-2,2a,3,4,5,6-hexahydrofuro[4,3,2-ef][3] benzazepine hydrochloride

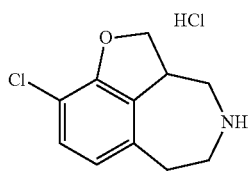 [SMILES: Cl ; Clc1ccc2c3c1OCC3CNCC2]

A) tert-butyl 7-bromo-9-chloro-2a,3,5,6-tetrahydrofuro[4,3,2-ef][3]benzazepine-4(2H)-carboxylate The title compound was obtained from tert-butyl 2a,3,5,6-tetrahydrofuro[4,3,2-ef][3]benzazepine-4(2H)-carboxylate in the same manner as in Steps B and C of Example 17.

$^1$H NMR (300 MHz, CDCl$_3$) δ 1.49 (9H, s), 2.70-3.10 (3H, m), 3.25-3.40 (1H, m), 3.80-4.40 (4H, m), 4.70-4.85 (1H, m), 7.35-7.50 (1H, m).

B) tert-butyl 9-chloro-2a,3,5,6-tetrahydrofuro[4,3,2-ef][3]benzazepine-4(2H)-carboxylate To a mixture of tert-butyl 7-bromo-9-chloro-2a,3,5,6-tetrahydrofuro[4,3,2-ef][3]benzazepine-4(2H)-carboxylate (70 mg) and THF (3 mL) was added sec-butyllithium/pentane solution (1.0 M, 199 μL) at −78° C. under argon atmosphere. The reaction mixture was stirred at −78° C. for 2 hr, water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) and HPLC (C18, mobile phase: water/acetonitrile (10 mM, containing NH$_4$HCO$_3$)) to give the title compound (15 mg).

$^1$H NMR (300 MHz, CDCl$_3$) δ 1.50 (9H, s), 2.65-3.10 (4H, m), 3.89 (1H, brs), 4.05-4.40 (3H, m), 4.80 (1H, t, J=9.5 Hz), 6.59 (1H, t, J=8.0 Hz), 7.03 (1H, t, J=7.9 Hz).

C) 9-chloro-2,2a,3,4,5,6-hexahydrofuro[4,3,2-ef][3] benzazepine hydrochloride

The title compound was obtained in the same manner as in Step B of Example 1.

Example 34

1-(2,2a,3,4,5,6-hexahydro-1H-azepino[3,4,5-cd]indol-1-yl)-2-methylpropan-1-one hydrochloride

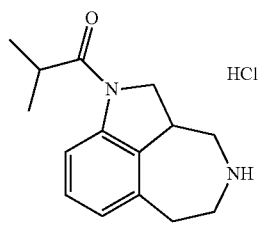 [SMILES: CC(C)C(=O)N1CC2CNCCc3cccc1c32 ; Cl]

The title compound was obtained from tert-butyl 1,2,2a,3,5,6-hexahydro-4H-azepino[3,4,5-cd]indole-4-carboxylate and 2-methylpropanoyl chloride in the same manner as in Step A of Example 20 and Step B of Example 1.

Example 35

1-(7-chloro-2,2a,3,4,5,6-hexahydro-1H-azepino[3,4,5-cd]indol-1-yl)-2-methylpropan-1-one hydrochloride

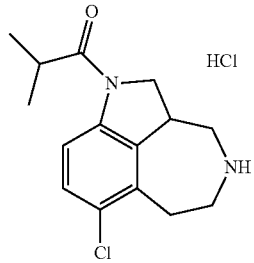 [SMILES: CC(C)C(=O)N1CC2CNCCc3c(Cl)ccc1c32 ; Cl]

The title compound was obtained from tert-butyl 1,2,2a,3,5,6-hexahydro-4H-azepino[3,4,5-cd]indole-4-carboxylate and 2-methylpropanoyl chloride in the same manner as in Step A of Example 20, Step A of Example 22 and Step B of Example 1.

Example 36

2,2a,3,4,5,6-hexahydro-1H-azepino[3,4,5-cd]indol-1-yl(phenyl)methanone hydrochloride

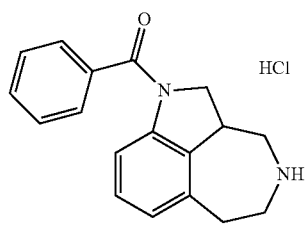 [SMILES: O=C(c1ccccc1)N1CC2CNCCc3cccc1c32 ; Cl]

A) tert-butyl 1-benzoyl-1,2,2a,3,5,6-hexahydro-4H-azepino[3,4,5-cd]indole-4-carboxylate The title compound was obtained from tert-butyl 1,2,2a,3,5,6-hexahydro-4H-azepino[3,4,5-cd]indole-4-carboxylate and benzoyl chloride in the same manner as in Step A of Example 20.

$^1$H NMR (300 MHz, CDCl$_3$) δ 1.48 (9H, s), 2.57-3.15 (4H, m), 3.42-3.85 (2H, m), 4.04-4.51 (3H, m), 6.83 (1H, d, J=7.2 Hz), 7.06 (1H, brs), 7.40-7.60 (5H, m), 7.78 (1H, brs).

B) 2,2a,3,4,5,6-hexahydro-1H-azepino[3,4,5-cd]indol-1-yl(phenyl)methanone hydrochloride The title compound was obtained in the same manner as in Step B of Example 1.

Example 37

(9-chloro-2,2a,3,4,5,6-hexahydro-1H-azepino[3,4,5-cd]indol-1-yl)(phenyl)methanone hydrochloride

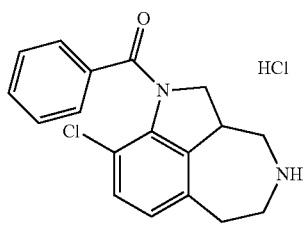 [SMILES: O=C(c1ccccc1)N1CC2CNCCc3ccc(Cl)c1c32 ; Cl]

A) tert-butyl 1-benzoyl-9-chloro-1,2,2a,3,5,6-hexahydro-4H-azepino[3,4,5-cd]indole-4-carboxylate A reaction mixture of tert-butyl 1-benzoyl-1,2,2a,3,5,6-hexahydro-4H-azepino[3,4,5-cd]indole-4-carboxylate (136 mg), palladium(II) acetate (4 mg), N-chlorosuccinimide (72 mg) and acetic acid (5 mL) was stirred at 100° C. under nitrogen atmosphere for 5 hr, basified with aqueous sodium bicarbonate, and extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) and HPLC (C18, mobile phase: water/acetonitrile (5 mM, containing AcONH$_4$)) to give the title compound (8 mg).

$^1$H NMR (300 MHz, CDCl$_3$) δ 1.47 (9H, s), 2.56-3.05 (4H, m), 3.56-3.87 (2H, m), 4.02-4.45 (3H, m), 6.88 (1H, d, J=8.3 Hz), 7.17 (1H, d, J=7.9 Hz), 7.41-7.59 (3H, m), 7.74 (2H, d, J 6.0 Hz).

B) (9-chloro-2,2a,3,4,5,6-hexahydro-1H-azepino[3,4,5-cd]indol-1-yl) (phenyl)methanone hydrochloride The title compound was obtained in the same manner as in Step B of Example 1.

Example 38

(7-chloro-2,2a,3,4,5,6-hexahydro-1H-azepino[3,4,5-cd]indol-1-yl)(phenyl)methanone hydrochloride

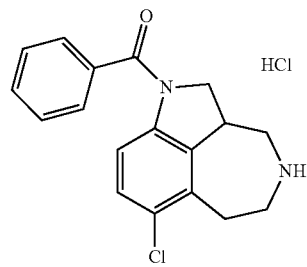 [SMILES: O=C(c1ccccc1)N1CC2CNCCc3c(Cl)ccc1c32 ; Cl]

A) tert-butyl 1-benzoyl-7-chloro-1,2,2a,3,5,6-hexahydro-4H-azepino[3,4,5-cd]indole-4-carboxylate A reaction mixture of tert-butyl 1-benzoyl-1,2,2a,3,5,6-hexahydro-4H-azepino[3,4,5-cd]indole-4-carboxylate (136 mg), palladium(II) acetate (4 mg), N-chlorosuccinimide (72 mg) and acetic acid (5 mL) was stirred at 100° C. under nitrogen atmosphere for 5 hr, basified with aqueous sodium bicarbonate, and extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) and HPLC (C18, mobile phase: water/acetonitrile (5 mM, containing AcONH$_4$)) to give the title compound (53 mg).

$^1$H NMR (300 MHz, CDCl$_3$) δ 1.48 (9H, s), 2.62-3.07 (3H, m), 3.48 (1H, dd, J=16.1, 5.1 Hz), 3.55-3.78 (2H, m), 4.00-4.41 (3H, m), 7.19 (1H, brs), 7.42-7.55 (5H, m), 7.91 (1H, brs).

B) (7-chloro-2,2a,3,4,5,6-hexahydro-1H-azepino[3,4,5-cd]indol-yl)(phenyl)methanone hydrochloride The title compound was obtained in the same manner as in Step B of Example 1.

Example 39

7,9-dichloro-1-(phenylcarbonyl)-2,2a,3,4,5,6-hexahydro-1H-azepino[3,4,5-cd]indole hydrochloride

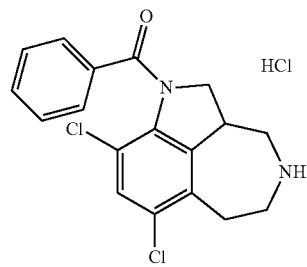 [SMILES: O=C(c1ccccc1)N1CC2CNCCc3c(Cl)cc(Cl)c1c32 ; Cl]

A) tert-butyl 1-benzoyl-7,9-dichloro-1,2,2a,3,5,6-hexahydro-4H-azepino[3,4,5-cd]indole-4-carboxylate A reaction mixture of tert-butyl 1-benzoyl-1,2,2a,3,5,6-hexahydro-4H-azepino[3,4,5-cd]indole-4-carboxylate (136 mg), palladium(II) acetate (4 mg), N-chlorosuccinimide (72 mg) and acetic acid (5 mL) was stirred at 100° C. under nitrogen atmosphere for 5 hr, basified with saturated aqueous sodium bicarbonate solution, and extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) and HPLC (C18, mobile phase: water/acetonitrile (5 mM, containing AcONH$_4$)) to give the title compound (22 mg).
$^1$H NMR (300 MHz, CDCl$_3$) δ 1.47 (9H, s), 2.39-2.89 (3H, m), 2.93-3.08 (1H, m), 3.36-3.51 (1H, m), 3.62-3.87 (2H, m), 4.09-4.35 (2H, m), 7.34 (1H, s), 7.41-7.61 (3H, m), 7.69-7.83 (2H, m).

B) 7,9-dichloro-1-(phenylcarbonyl)-2,2a,3,4,5,6-hexahydro-1H-azepino[3,4,5-cd]indole hydrochloride The title compound was obtained in the same manner as in Step B of Example 1.

Example 40

9-isopropyl-1-methyl-2,2a,3,4,5,6-hexahydro-1H-azepino[3,4,5-cd]indole

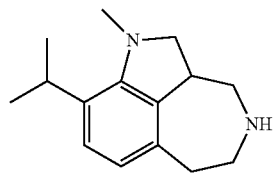 [SMILES: CC(C)c1ccc2c3c1N(C)CC3CNCC2]

A) tert-butyl 9-isopropyl-1-methyl-1,2,2a,3,5,6-hexahydro-4H-azepino[3,4,5-cd]indole-4-carboxylate A reaction mixture of tert-butyl 9-chloro-1-methyl-1,2,2a,3,5,6-hexahydro-4H-azepino[3,4,5-cd]indole-4-carboxylate (80 mg), 4,4,5,5-tetramethyl-2-(prop-1-en-2-yl)-1,3,2-dioxaborolane (140 μL), palladium(II) acetate (2.8 mg), tricyclohexyl phosphine (7.0 mg), potassium phosphate (263 mg), toluene (2 mL) and water (2 mL) was stirred overnight at 100° C. under argon atmosphere, and water was added thereto. The reaction mixture was filtered through Celite, and the filtrate was extracted with ethyl acetate. The extract was washed with saturated brine, dried over anhydrous sodium sulfate, and filtered, and the solvent was evaporated under reduced pressure. A reaction mixture of the residue, 10% palladium on carbon (10 mg) and ethanol (2 mL) was stirred overnight at 50° C. under hydrogen atmosphere. The catalyst was removed by filtration, and the solvent was evaporated under reduced pressure. The residue was purified by silica gel column chromatography (ethyl acetate/hexane) to give the title compound (74 mg).
MS (ESI+): [M+H]$^+$ 337.1.

B) 9-isopropyl-1-methyl-2,2a,3,4,5,6-hexahydro-1H-azepino[3,4,5-cd]indole

A reaction mixture of tert-butyl 9-isopropyl-1-methyl-1,2,2a,3,5,6-hexahydro-4H-azepino[3,4,5-cd]indole-4-carboxylate (74 mg) and 4M hydrogen chloride/ethyl acetate (2 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (NH silica gel, ethyl acetate/hexane) to give the title compound.

Example 41

3,4,5,6-tetrahydrothieno[4,3,2-ef][3]benzazepine hydrochloride

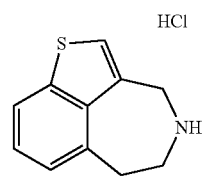 [SMILES: Cl ; c1cc2c3c(csc3c1)CNCC2]

A) 4-(2-nitrovinyl)-1-benzothiophene

The title compound was obtained from 1-benzothiophene-4-carbaldehyde in the same manner as in Step B of Example 31.
$^1$NMR (400 MHz, CDCl$_3$) δ 7.42 (1H, t, J=7.8 Hz), 7.62-7.74 (4H, m), 8.03 (1H, d, J=8.0 Hz), 8.53 (1H, d, J=13.6 Hz).

B) N-(2-(1-benzothiophen-4-yl)ethyl)-2,2,2-trifluoroacetamide

To a mixture of lithium aluminium hydride (5.1 g) and ether (179 mL) was added dropwise a mixture of 4-(2-nitrovinyl)-1-benzothiophene (5.5 g) and ether (89 mL) at 0° C. The reaction mixture was stirred at room temperature for 2 hr, 2M aqueous sodium hydroxide solution was added thereto at 0° C., and the mixture was extracted with ethyl acetate. The extract was washed with saturated brine, dried over anhydrous sodium sulfate, and filtered, and the solvent was evaporated under reduced pressure. The obtained residue (4.5 g) was diluted with dichloromethane (127 mL), and pyridine (4.1 mL) and trifluoroacetic anhydride (5.4 mL) were added thereto at 0° C. The reaction mixture was stirred at room temperature for 1 hr, and dichloromethane (100 mL) was added thereto. The mixture was washed with 10% aqueous tartaric acid and saturated brine, dried over anhydrous sodium sulfate, and filtered, and the solvent was evaporated under reduced pressure. The residue was purified by silica gel column chromatography (ethyl acetate/hexane) to give the title compound.
$^1$H NMR (400 MHz, CDCl$_3$) δ 3.24 (2H, t, J=7.0 Hz), 3.72 (2H, q, J=6.7 Hz), 6.34 (1H, brs), 7.16 (1H, d, J=7.2

Hz), 7.31 (1H, t, J=7.6 Hz), 7.46 (1H, d, J=5.6 Hz), 7.52 (1H, d, J=5.6 Hz), 7.82 (1H, d, J=8.0 Hz).

C) 5,6-dihydrothieno[4,3,2-ef][3]benzazepine

To a mixture of N-(2-(1-benzothiophen-4-yl)ethyl)-2,2,2-trifluoroacetamide (5.0 g) and dichloromethane (183 mL) were added dichloromethyl methyl ether (3.3 mL) and titanium tetrachloride (4.0 mL) at 0° C. The reaction mixture was stirred at room temperature for 18 hr, and aqueous sodium bicarbonate/ice was added thereto. The mixture was stirred for 30 min, and extracted with dichloromethane. The extract was washed with saturated brine, dried over anhydrous sodium sulfate, and filtered, and the solvent was evaporated under reduced pressure. The residue was purified by silica gel column chromatography (ethyl acetate/hexane) to give the title compound (650 mg).
$^1$H NMR (400 MHz, CDCl$_3$) δ 3.12-3.18 (2H, m), 4.06-4.14 (2H, m), 7.17 (1H, dd, J=7.2, 0.8 Hz), 7.31 (1H, t, J=7.8 Hz), 7.74 (1H, d, J=8.0 Hz), 7.78 (1H, s), 8.48-8.52 (1H, m).

D) tert-butyl 5,6-dihydrothieno[4,3,2-ef][3]benzazepine-4(3H)-carboxylate 5,6-Dihydrothieno[4,3,2-ef][3]benzazepine (650 mg) was diluted with dichloromethane (23 mL), and acetic acid (298 μL) and sodium triacetoxyborohydride (1.5 g) were added thereto at 0° C. The reaction mixture was stirred at room temperature for 1 hr, and the pH was adjusted to 9-10 with saturated aqueous sodium bicarbonate solution. To the reaction mixture was added Boc$_2$O (806 μL), the mixture was stirred at room temperature for 1 hr, and water (100 mL) and dichloromethane (50 mL) were added thereto. The organic layer was separated, and the aqueous layer was extracted with dichloromethane. The combined organic layer were washed with saturated aqueous sodium bicarbonate solution, dried over anhydrous sodium sulfate, and filtered, and the solvent was evaporated under reduced pressure. The residue was purified by silica gel column chromatography (ethyl acetate/hexane) to give the title compound (898 mg).
$^1$H NMR (400 MHz, CDCl$_3$) δ 1.39-1.43 (9H, m), 3.33 (2H, q, J=5.2 Hz), 3.84 (1H, t, J=6.0 Hz), 3.90 (1H, t, J=6.2 Hz), 4.72 (1H, s), 4.86 (1H, s), 7.07-7.25 (3H, m), 7.68-7.72 (1H, m).

E) 3,4,5,6-tetrahydrothieno[4,3,2-ef][3]benzazepine hydrochloride

A reaction mixture of tert-butyl 5,6-dihydrothieno[4,3,2-ef][3]benzazepine-4(3H)-carboxylate (150 mg) and 4M hydrogen chloride/ethyl acetate (3 mL) was stirred at room temperature for 2 hr, and the solvent was evaporated under reduced pressure. The residue was recrystallized from ethanol-ether to give the title compound (100 mg).

Example 42

2,2a,3,4,5,6-hexahydrothieno[4,3,2-ef][3]benzazepine 1,1-dioxide hydrochloride

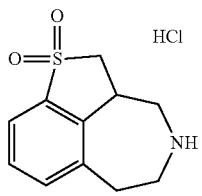 [SMILES: O=S1(=O)CC2CNCCc3cccc1c32 ; Cl]

A) tert-butyl 5,6-dihydrothieno[4,3,2-ef][3]benzazepine-4(3H)-carboxylate 1,1-dioxide To a mixture of tert-butyl 5,6-dihydrothieno[4,3,2-ef][3]benzazepine-4(3H)-carboxylate (50 mg) and methanol (2 mL) was added 3-chloroperbenzoic acid (104 mg) at 0° C. The reaction mixture was stirred at room temperature for 5 hr, water was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane) to give the title compound (43 mg).
$^1$H NMR (300 MHz, CDCl$_3$) δ 1.43 (9H, s), 3.08-3.22 (2H, m), 3.68-3.87 (2H, m), 4.39-4.63 (2H, m), 6.39-6.58 (1H, m), 7.33-7.40 (1H, m), 7.46 (1H, t, J=7.5 Hz), 7.61 (1H, d, J=7.5 Hz).

B) tert-butyl 2a,3,5,6-tetrahydrothieno[4,3,2-ef][3]benzazepine-4(2H)-carboxylate 1,1-dioxide A mixture of tert-butyl 5,6-dihydrothieno[4,3,2-ef][3]benzazepine-4(3H)-carboxylate 1,1-dioxide (40 mg), 10% palladium on carbon (50 mg) and acetic acid (2 mL) was stirred at room temperature under hydrogen atmosphere for 2 hr. The catalyst was removed by filtration, and the solvent was evaporated under reduced pressure. The residue was purified by silica gel column chromatography (ethyl acetate/hexane) to give the title compound (40 mg).
$^1$H NMR (300 MHz, CDCl$_3$) δ 1.50 (9H, s), 2.71-3.21 (5H, m), 3.62-3.92 (2H, m), 4.17-4.47 (2H, m), 7.35-7.47 (2H, m), 7.57-7.66 (1H, m).

C) 2,2a,3,4,5,6-hexahydrothieno[4,3,2-ef][3]benzazepine 1,1-dioxide hydrochloride The title compound was obtained in the same manner as in Step B of Example 1.
$^1$H NMR (300 MHz, CDCl$_3$) δ 2.93-3.30 (4H, m), 3.44 (1H, dd, J=14.2, 6.6 Hz), 3.51-3.66 (2H, m), 3.95 (1H, dd, J=14.0, 8.3 Hz), 4.14 (1H, d, J=6.8 Hz), 7.50-7.63 (2H, m), 7.65-7.72 (1H, m), 9.37 (2H, brs).

Example 43

2,2a,3,4,5,6-hexahydrothieno[4,3,2-ef][3]benzazepine hydrochloride

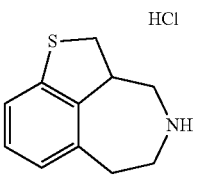 [SMILES: Cl ; c1cc2c3c(c1)SCC3CNCC2]

A) tert-butyl 2a,3,5,6-tetrahydrothieno[4,3,2-ef][3]benzazepine-4(2H)-carboxylate A reaction mixture of tert-butyl 2a,3,5,6-tetrahydrothieno[4,3,2-ef][3]benzazepine-4(2H)-carboxylate 1,1-dioxide (78 mg), lithium aluminium hydride (23 mg) and ether (3 mL) was stirred at room temperature for 1 hr, water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (25 mg).

¹H NMR (300 MHz, CDCl₃) 51.49 (9H, s),2.70-3.15 (5H, m), 3.30-3.55 (1H, m), 3.75-3.90 (1H, m), 4.10-4.35 (2H, m), 6.80 (1H, brs), 7.00-7.05 (2H, m).

B) 2,2a,3,4,5,6-hexahydrothieno[4,3,2-ef][3]benzazepine hydrochloride

The title compound was obtained in the same manner as in Step B of Example 1.

EXAMPLE 44 methyl(2aS)-9-chloro-2,2a,3,4,5,6-hexahydro-1H-azepino[3,4,5-cd]indole-1-carboxylate hydrochloride

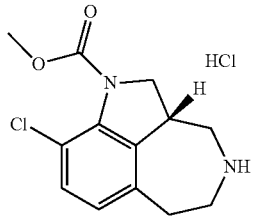 [SMILES: COC(=O)N1C[C@@H]2CNCCc3ccc(Cl)c1c32 ; Cl]

The title compound was obtained from tert-butyl(2aR)-9-chloro-1,2,2a,3,5,6-hexahydro-4H-azepino[3,4,5-cd]indole-4-carboxylate and methyl chloroformate in the same manner as in Step A of Example 20 and Step C of Example 28.

Example 45

(2a5)-9-chloro-1-(methylsulfonyl)-2,2a,3,4,5,6-hexahydro-1H-azepino[3,4,5-cd]indole hydrochloride

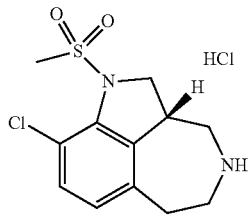 [SMILES: CS(=O)(=O)N1C[C@@H]2CNCCc3ccc(Cl)c1c32 ; Cl]

A) tert-butyl(2aS)-9-chloro-1-(methylsulfonyl)-1,2,2a,3,5,6-hexahydro-4H-azepino[3,4,5-cd]indole-4-carboxylate To a mixture of tert-butyl(2aR)-9-chloro-1,2,2a,3,5,6-hexahydro-4H-azepino[3,4,5-cd]indole-4-carboxylate (50 mg), triethylamine (34 μL) and acetonitrile (2 ml) was added mesyl chloride (19 μL). The reaction mixture was stirred overnight at room temperature under nitrogen atmosphere, water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (40 mg).

¹H NMR (300 MHz, CDCl₃) δ 1.49 (9H, s), 2.42-3.09 (4H, m), 3.20-3.45 (4H, m), 3.86 (1H, brs), 4.06-4.43 (2H, m), 4.54 (1H, dd, J=11.9, 7.7 Hz), 6.87 (1H, d, J=8.3 Hz), 7.13 (1H, d, J=8.3 Hz).

B) (2aS)-9-chloro-1-(methylsulfonyl)-2,2a,3,4,5,6-hexahydro-1H-azepino[3,4,5-cd]indole hydrochloride The title compound was obtained in the same manner as in Step B of Example 1.

Example 46

(2aS)-9-chloro-1-propyl-2,2a,3,4,5,6-hexahydro-1H-azepino[3,4,5-cd]indole

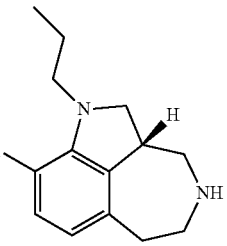

To a mixture of tert-butyl(2aR)-9-chloro-1,2,2a,3,5,6-hexahydro-4H-azepino[3,4,5-cd]indole-4-carboxylate (50 mg), 1-propyl iodide (24 μl) and DMF (2 mL) was added sodium hydride (60%, 8 mg). The reaction mixture was stirred overnight at room temperature under nitrogen atmosphere, water was added thereto, and the mixture was extracted with ethyl acetate. The extract was washed with water and saturated brine, dried over anhydrous sodium sulfate, and filtered, and the solvent was evaporated under reduced pressure. The residue was purified by silica gel column chromatography (ethyl acetate/hexane). A reaction mixture of the obtained residue (9 mg) and 4M hydrogen chloride/ethyl acetate (2 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. The residue was purified by HPLC (C18, mobile phase: water/acetonitrile (5 mM, containing AcONH₄)) to give the title compound (3 mg).

Example 47

(2aS)-9-chloro-1-phenyl-2,2a,3,4,5,6-hexahydro-1H-azepino[3,4,5-cd]indole

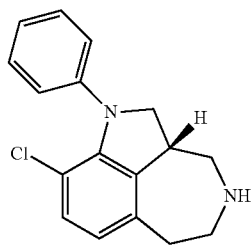 [SMILES: Clc1ccc2c3c1N(c1ccccc1)C[C@@H]3CNCC2]

A) tert-butyl(2aR)-9-chloro-1-phenyl-1,2,2a,3,5,6-hexahydro-4H-azepino [3,4,5-cd] indole-4-carboxylate A reaction mixture of tert-butyl(2aR)-9-chloro-1,2,2a,3,5,6-hexahydro-4H-azepino[3,4,5-cd]indole-4-carboxylate (50 mg), Pd$_2$(dba)$_3$ (3 mg), 2-dicyclohexyl phosphino-2',4',6'-triisopropylbiphenyl (6 mg), sodium tert-butoxide (23 mg), benzene iodide (54 µL) and toluene (3 mL) was stirred at 100° C. for 2 hr under argon atmosphere, water was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (ethyl acetate/hexane) to give the title compound (63 mg).

MS (ESI+): [M+H]$^+$ 385.2.

B) (2aS)-9-chloro-1-phenyl-2,2a,3,4,5,6-hexahydro-1H-azepino[3,4,5-cd]indole

A reaction mixture of tert-butyl(2aR)-9-chloro-1-phenyl-1,2,2a,3,5,6-hexahydro-4H-azepino[3,4,5-cd]indole-4-carboxylate (63 mg) and 4M hydrogen chloride/ethyl acetate (2 mL) was stirred at room temperature for 2 hr, saturated aqueous sodium bicarbonate solution was added thereto, and the mixture was extracted with ethyl acetate. The extract was washed with saturated brine, dried over anhydrous sodium sulfate, and filtered, and the solvent was evaporated under reduced pressure. The residue was purified by silica gel column chromatography (NH silica gel, ethyl acetate/methanol) and HPLC (C18, mobile phase: water/acetonitrile (5 mM, containing AcONH$_4$)). The obtained residue was diluted with ethanol, 1M hydrochloric acid (172 µL) was added thereto, and the solvent was evaporated under reduced pressure to give the title compound (170 mg).

The compounds of Examples produced according to the above-mentioned method or a method analogous thereto are shown in the following tables. Mass in the tables means measured value.

| Example | IUPAC Name | Structure | Salt | MS |
|---|---|---|---|---|
| 1 | 3,4,5,6-tetrahydro-1H-azepino[3,4,5-cd]indole | 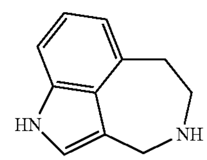 [SMILES: c1cc2c3c(c[nH]c3c1)CNCC2] | HCl | 173 |
| 2 | 2,2a,3,4,5,6-hexahydro-1H-azepino[3,4,5-cd]indole | 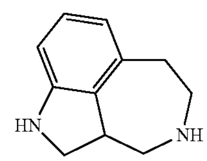 [SMILES: c1cc2c3c(c1)NCC3CNCC2] | 2HCl | 175 |
| 3 | 1-methyl-3,4,5,6-tetrahydro-1H-azepino[3,4,5-cd]indole | 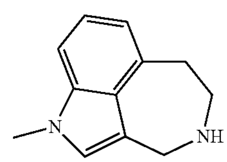 | | 187 |
| 4 | 1-methyl-2,2a,3,4,5,6-hexahydro-1H-azepino[3,4,5-cd]indole | 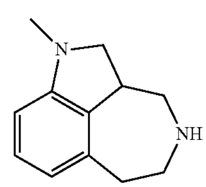 | HCl | 189 |
| 5 | 9-chloro-1-methyl-2,2a,3,4,5,6-hexahydro-1H-azepino[3,4,5-cd]indole | 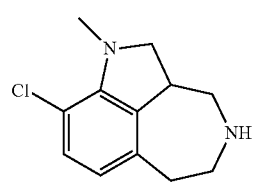 | HCl | 223 |

-continued

| Example | IUPAC Name | Structure | Salt | MS |
|---|---|---|---|---|
| 6 | 7-chloro-1-methyl-2,2a,3,4,5,6-hexahydro-1H-azepino[3,4,5-cd]indole | 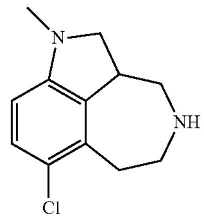 | HCl | 223 |
| 7 | 7,9-dichloro-1-methyl-2,2a,3,4,5,6-hexahydro-1H-azepino[3,4,5-cd]indole | 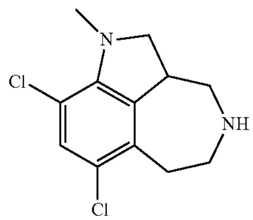 [SMILES: CN1CC2CNCCc3c(Cl)cc(Cl)c1c32] | | 257 |
| 8 | (2aR)-9-chloro-1-methyl-2,2a,3,4,5,6-hexahydro-1H-azepino[3,4,5-cd]indole | 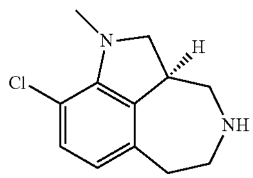 | HCl | 223 |
| 9 | (2aS)-9-chloro-1-methyl-2,2a,3,4,5,6-hexahydro-1H-azepino[3,4,5-cd]indole | 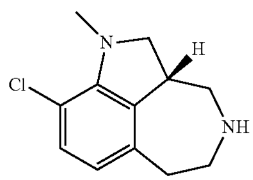 | HCl | 223 |
| 10 | 1,9-dimethyl-2,2a,3,4,5,6-hexahydro-1H-azepino[3,4,5-cd]indole | 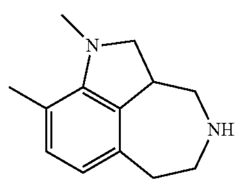 | HCl | 203 |
| 11 | (2aS)-1,9-dimethyl-2,2a,3,4,5,6-hexahydro-1H-azepino[3,4,5-cd]indole | 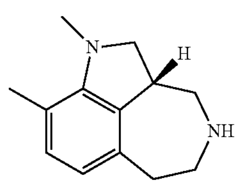 | 0.5 $H_2SO_4$ | 203 |
| 12 | (2aR)-1,9-dimethyl-2,2a,3,4,5,6-hexahydro-1H-azepino[3,4,5-cd]indole | 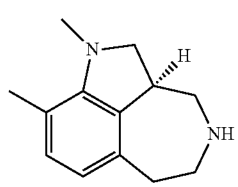 | 0.5 $H_2SO_4$ | 203 |
| 13 | 7-bromo-1-methyl-2,2a,3,4,5,6-hexahydro-1H-azepino[3,4,5-cd]indole | 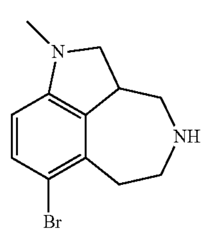 | HCl | 267 |

-continued

| Example | IUPAC Name | Structure | Salt | MS |
|---|---|---|---|---|
| 14 | 7,9-dibromo-1-methyl-2,2a,3,4,5,6-hexahydro-1H-azepino[3,4,5-cd]indole | 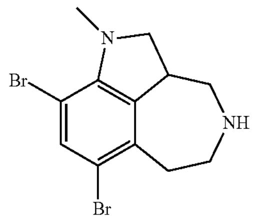 | HCl | 345 |
| 15 | 1-isopropyl-2,2a,3,4,5,6-hexahydro-1H-azepino[3,4,5-cd]indole | 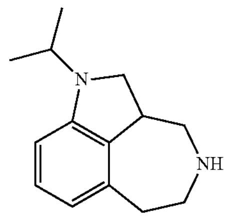 [SMILES: CC(C)N1CC2CNCCc3cccc1c32] | HCl | 217 |
| 16 | 9-chloro-1-isopropyl-2,2a,3,4,5,6-hexahydro-1H-azepino[3,4,5-cd]indole | 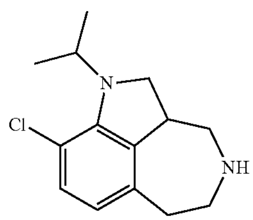 [SMILES: CC(C)N1CC2CNCCc3ccc(Cl)c1c32] | HCl | 251 |
| 17 | (2aS)-9-chloro-1-isopropyl-2,2a,3,4,5,6-hexahydro-1H-azepino[3,4,5-cd]indole | 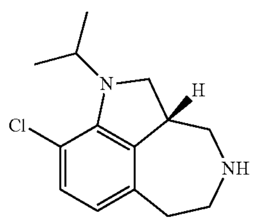 [SMILES: CC(C)N1C[C@@H]2CNCCc3ccc(Cl)c1c32] | HCl | 251 |
| 18 | (2aR)-9-chloro-1-isopropyl-2,2a,3,4,5,6-hexahydro-1H-azepino[3,4,5-cd]indole | 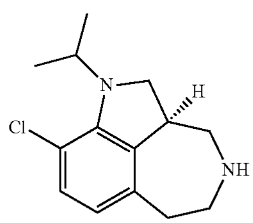 [SMILES: CC(C)N1C[C@H]2CNCCc3ccc(Cl)c1c32] | HCl | 251 |
| 19 | 1-benzyl-2,2a,3,4,5,6-hexahydro-1H-azepino[3,4,5-cd]indole | 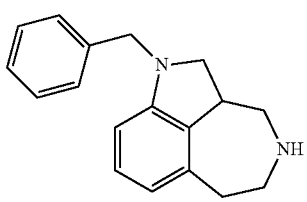 [SMILES: c1ccc(CN2CC3CNCCc4cccc2c43)cc1] | HCl | 265 |
| 20 | 1-(2,2a,3,4,5,6-hexahydro-1H-azepino[3,4,5-cd]indol-1-yl)ethanone | 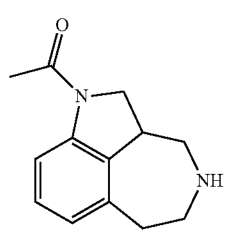 [SMILES: CC(=O)N1CC2CNCCc3cccc1c32] | HCl | 217 |

-continued

| Example | IUPAC Name | Structure | Salt | MS |
|---|---|---|---|---|
| 21 | 1-(9-chloro-2,2a,3,4,5,6-hexahydro-1H-azepino[3,4,5-cd]indol-1-yl)ethanone | 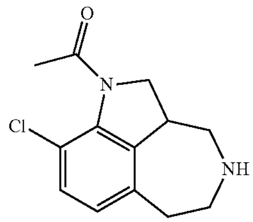 [SMILES: CC(=O)N1CC2CNCCc3ccc(Cl)c1c32] | HCl | 251 |
| 22 | 1-(7-chloro-2,2a,3,4,5,6-hexahydro-1H-azepino[3,4,5-cd]indol-1-yl)ethanone | 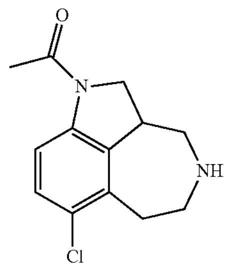 [SMILES: CC(=O)N1CC2CNCCc3c(Cl)ccc1c32] | HCl | 251 |
| 23 | 1-(7,9-dichloro-2,2a,3,4,5,6-hexahydro-1H-azepino[3,4,5-cd]indol-1-yl)ethanone | 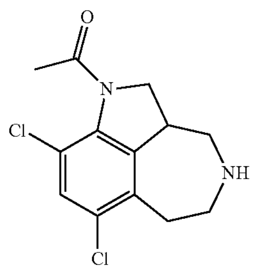 [SMILES: CC(=O)N1CC2CNCCc3c(Cl)cc(Cl)c1c32] | | 285 |
| 24 | 1-((2aS)-9-chloro-2,2a,3,4,5,6-hexahydro-1H-azepino[3,4,5-cd]indol-1-yl)ethanone | 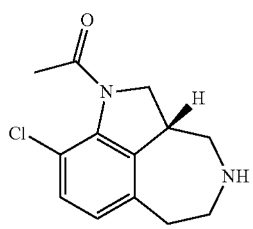 [SMILES: CC(=O)N1C[C@@H]2CNCCc3ccc(Cl)c1c32] | HCl | 251 |
| 25 | 1-((2aR)-9-chloro-2,2a,3,4,5,6-hexahydro-1H-azepino[3,4,5-cd]indol-1-yl)ethanone | 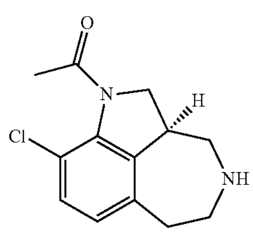 [SMILES: CC(=O)N1C[C@H]2CNCCc3ccc(Cl)c1c32] | HCl | 251 |
| 26 | 9-chloro-2,2a,3,4,5,6-hexahydro-1H-azepino[3,4,5-cd]indole | 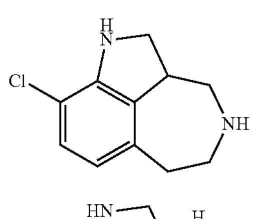 | | 209 |
| 27 | (2aS)-9-chloro-2,2a,3,4,5,6-hexahydro-1H-azepino[3,4,5-cd]indole | 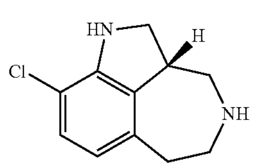 [SMILES: Clc1ccc2c3c1NC[C@@H]3CNCC2] | 2HCl | 209 |

-continued

| Example | IUPAC Name | Structure | Salt | MS |
|---|---|---|---|---|
| 28 | (2aS)-1-benzyl-9-chloro-2,2a,3,4,5,6-hexahydro-1H-azepino[3,4,5-cd]indole | 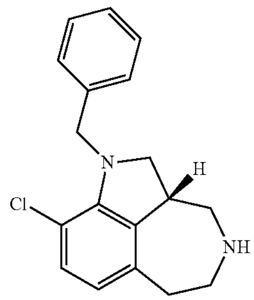 [SMILES: Clc1ccc2c3c1N(Cc1ccccc1)C[C@@H]3CNCC2] | HCl | 299 |
| 29 | (2aS)-9-chloro-1-ethyl-2,2a,3,4,5,6-hexahydro-1H-azepino[3,4,5-cd]indole | 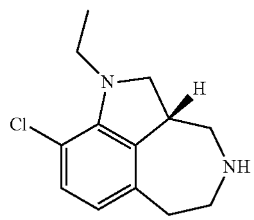 [SMILES: CCN1C[C@@H]2CNCCc3ccc(Cl)c1c32] | HCl | 237 |
| 30 | (2aS)-9-chloro-1-cyclopropyl-2,2a,3,4,5,6-hexahydro-1H-azepino[3,4,5-cd]indole | 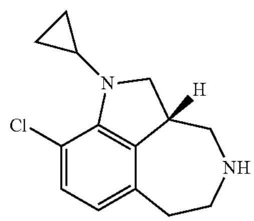 [SMILES: Clc1ccc2c3c1N(C1CC1)C[C@@H]3CNCC2] | | 249 |
| 31 | 3,4,5,6-tetrahydrofuro[4,3,2-ef][3]benzazepine | 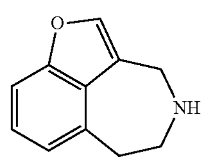 [SMILES: c1cc2c3c(coc3c1)CNCC2] | HCl | 174 |
| 32 | 2,2a,3,4,5,6-hexahydrofuro[4,3,2-ef][3]benzazepine | 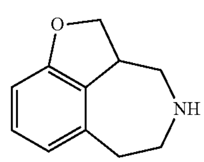 [SMILES: c1cc2c3c(c1)OCC3CNCC2] | HCl | 176 |
| 33 | 9-chloro-2,2a,3,4,5,6-hexahydrofuro[4,3,2-ef][3]benzazepine | 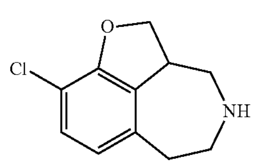 [SMILES: Clc1ccc2c3c1OCC3CNCC2] | HCl | 210 |
| 34 | 1-(2,2a,3,4,5,6-hexahydro-1H-azepino[3,4,5-cd]indol-1-yl)-2-methylpropan-1-one | 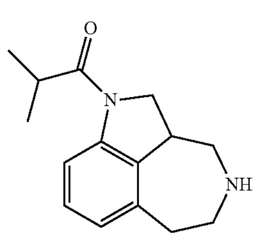 [SMILES: CC(C)C(=O)N1CC2CNCCc3cccc1c32] | HCl | 245 |

-continued

| Example | IUPAC Name | Structure | Salt | MS |
|---|---|---|---|---|
| 35 | 1-(7-chloro-2,2a,3,4,5,6-hexahydro-1H-azepino[3,4,5-cd]indol-1-yl)-2-methylpropan-1-one | 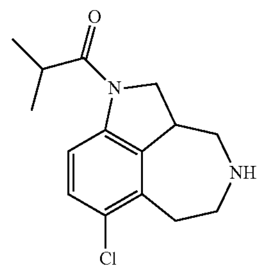 [SMILES: CC(C)C(=O)N1CC2CNCCc3c(Cl)ccc1c32] | HCl | 279 |
| 36 | 2,2a,3,4,5,6-hexahydro-1H-azepino[3,4,5-cd]indol-1-yl(phenyl)methanone | 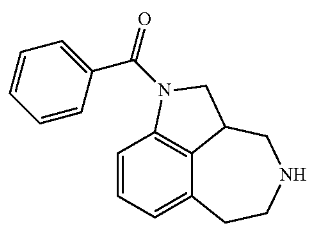 [SMILES: O=C(c1ccccc1)N1CC2CNCCc3cccc1c32] | HCl | 279 |
| 37 | (9-chloro-2,2a,3,4,5,6-hexahydro-1H-azepino[3,4,5-cd]indol-1-yl)(phenyl)methanone | 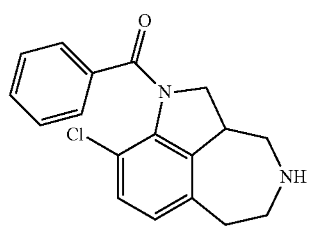 [SMILES: O=C(c1ccccc1)N1CC2CNCCc3ccc(Cl)c1c32] | HCl | 313 |
| 38 | (7-chloro-2,2a,3,4,5,6-hexahydro-1H-azepino[3,4,5-cd]indol-1-yl)(phenyl)methanone | 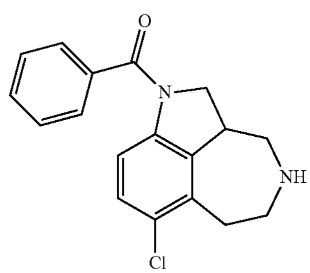 [SMILES: O=C(c1ccccc1)N1CC2CNCCc3c(Cl)ccc1c32] | HCl | 313 |
| 39 | 7,9-dichloro-1-(phenylcarbonyl)-2,2a,3,4,5,6-hexahydro-1H-azepino[3,4,5-cd]indole | 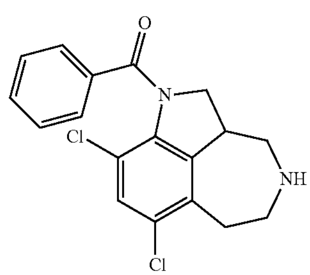 [SMILES: O=C(c1ccccc1)N1CC2CNCCc3c(Cl)cc(Cl)c1c32] | HCl | 347 |
| 40 | 9-isopropyl-1-methyl-2,2a,3,4,5,6-hexahydro-1H-azepino[3,4,5-cd]indole | 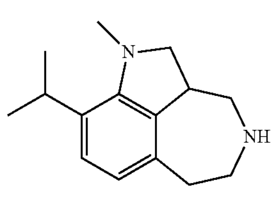 [SMILES: CC(C)c1ccc2c3c1N(C)CC3CNCC2] | | 231 |

-continued

| Example | IUPAC Name | Structure | Salt | MS |
|---|---|---|---|---|
| 41 | 3,4,5,6-tetrahydrothieno[4,3,2-ef][3]benzazepine | | HCl | 190 |
| 42 | 2,2a,3,4,5,6-hexahydrothieno[4,3,2-ef][3]benzazepine 1,1-dioxide | | HCl | |

¹H NMR (300 MHz, CDCl₃) δ 2.93-3.30 (4H, m), 3.44 (1H, dd, J = 14.2, 6.6 Hz), 3.51-3.66 (2H, m), 3.95 (1H, dd, J = 14.0, 8.3 Hz), 4.14 (1H, d, J = 6.8 Hz), 7.50-7.63 (2H, m), 7.65-7.72 (1H, m), 9.37 (2H, brs).

| Example | IUPAC Name | Structure | Salt | MS |
|---|---|---|---|---|
| 43 | 2,2a,3,4,5,6-hexahydrothieno[4,3,2-ef][3]benzazepine | 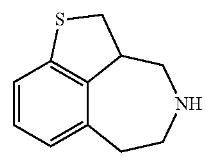 [SMILES: c1cc2c3c(c1)SCC3CNCC2] | HCl | 192 |
| 44 | methyl (2aS)-9-chloro-2,2a,3,4,5,6-hexahydro-1H-azepino[3,4,5-cd]indole-1-carboxylate | 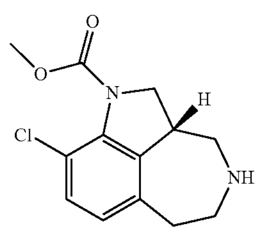 [SMILES: COC(=O)N1C[C@@H]2CNCCc3ccc(Cl)c1c32] | HCl | 267 |
| 45 | (2aS)-9-chloro-1-(methylsulfonyl)-2,2a,3,4,5,6-hexahydro-1H-azepino[3,4,5-cd]indole | 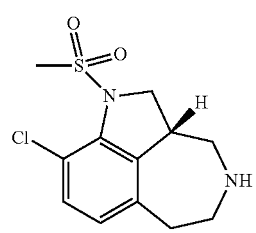 [SMILES: CS(=O)(=O)N1C[C@@H]2CNCCc3ccc(Cl)c1c32] | HCl | 287 |
| 46 | (2aS)-9-chloro-1-propyl-2,2a,3,4,5,6-hexahydro-1H-azepino[3,4,5-cd]indole | 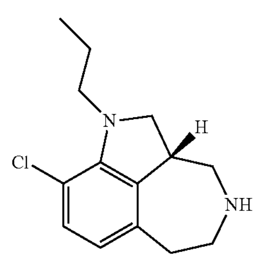 [SMILES: CCCN1C[C@@H]2CNCCc3ccc(Cl)c1c32] | | 251 |
| 47 | (2aS)-9-chloro-1-phenyl-2,2a,3,4,5,6-hexahydro-1H-azepino[3,4,5-cd]indole | 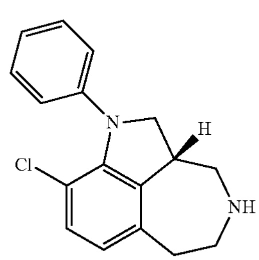 [SMILES: Clc1ccc2c3c1N(c1ccccc1)C[C@@H]3CNCC2] | | 285 |

Formulation Example 1

(1) The compound of Example 1　10 mg
(2) Lactose　60 mg
(3) Cornstarch　35 mg
(4) Hydroxypropylmethylcellulose　3 mg
(5) Magnesium stearate　2 mg A mixture of 10 mg of the compound obtained in Example 1, 60 mg of lactose and 35 mg of corn starch is granulated using 0.03 mL of a 10 wt % aqueous hydroxypropylmethylcellulose solution (3 mg as hydroxypropylmethylcellulose), and then dried at 40° C. and sieved. The obtained granules are mixed with 2 mg of magnesium stearate and compressed. The obtained uncoated tablets are sugar-coated with an aqueous suspension of sucrose, titanium dioxide, talc and gum arabic. The thus-coated tablets are glazed with beeswax to give finally-coated tablets.

Formulation Example 2

| | | |
|---|---|---|
| (1) | The compound of Example 1 | 10 mg |
| (2) | Lactose | 70 mg |
| (3) | Cornstarch | 50 mg |
| (4) | Soluble starch | 7 mg |
| (5) | Magnesium stearate | 3 mg |

The compound (10 mg) obtained in Example 1 and 3 mg of magnesium stearate are granulated with 0.07 mL of an aqueous solution of soluble starch (7 mg as soluble starch), dried, and mixed with 70 mg of lactose and 50 mg of corn starch. The mixture is compressed to give tablets.

Reference Formulation Example 1

| | | |
|---|---|---|
| (1) | Rofecoxib | 5.0 mg |
| (2) | Sodium chloride | 20.0 mg |
| (3) | Distilled water | amount to make total volume 2.0 mL |

Rofecoxib (5.0 mg) and 20.0 mg of sodium chloride are dissolved in distilled water, and water is added to make the total volume 2.0 mL. The solution is filtered, and filled into 2 mL of ampoule under sterile condition. The ampoule is sterilized, and then sealed to give a solution for injection.

Reference Formulation Example 2

| | | |
|---|---|---|
| (1) | Rofecoxib | 50 mg |
| (2) | Lactose | 34 mg |
| (3) | Cornstarch | 10.6 mg |
| (4) | Cornstarch (paste) | 5 mg |
| (5) | Magnesium stearate | 0.4 mg |
| (6) | Calcium carboxymethylcellulose | 20 mg |
| | total | 120 mg |

The above-mentioned (1) to (6) are mixed according to a conventional method and the mixture is tableted by a tableting machine to give a tablet.

Formulation Example 3

The formulation prepared in Formulation Example 1 or 2, and the formulation prepared in Reference Formulation Example 1 or 2 are combined.

Experimental Example 1

The serotonin 5-HT$_{2C}$ receptor agonist activity of the compound of the present invention was evaluated based on the changes in the intracellular calcium concentration by the following method. After transcription, 5-HT$_{2C}$ undergoes RNA editing of the second intracellular loop, which results in the change of three amino acids and 14 receptor isoforms. 5-HT$_{2C}$ stably expressing CHO cell that expresses VSV type of the isoform stably was purchased from Euroscreen S.A., and cultured in UltraCHO (BioWhittaker) medium containing 1% dialyzed bovine serum and 400 μg/mL G418. The cells were plated in a 384-well black clear bottom plate (PE Biosystems) at 5000 cells/well, and cultured for 24 hr in a CO$_2$ incubator, and changes in the intracellular calcium concentration mediated by the 5-HT$_{2C}$ receptor were evaluated using Calcium Kit-Fluo 3 (Dojindo Laboratories). A calcium kit buffer containing 2.5 mM probenecid, 0.04% Pluronic F-127 and 2.5 mg Fluo-3 AM (calcium indicator fluorescent dye) was prepared and used as a Fluo-3 loading solution (contained in Dojindo Laboratories Calcium Kit). The loading solution was incubated at 37° C., the medium in the wells of the cell culture plate was removed, and the loading solution was added to each well by 40 μl. The cells were reacted at 37° C. for 1 hr to allow uptake of Fluo-3 AM into the cells and washed.

The compound of the present invention was diluted with a calcium kit buffer, and dispensed to each well of the 384-well plate (REMP) by 40 μL to give a test compound plate. The cell culture plate and test compound plate were set on a Fluometric Imaging Plate Reader (FLIPR, Molecular Devices), and changes in the intracellular calcium concentration were measured. An increase in the fluorescence intensity of Fluo-3 matches with an increase in the intracellular calcium concentration mediated by a receptor. The changes in the intracellular fluorescence intensity were measured every second with a CCD camera of FLIPR and, after measurement for 5 seconds before addition of the compound, a diluted solution of the compound of the present invention was added by 20 μL to each well of the cell culture plate using an automatic dispenser in FLIPR.

The agonist activity was evaluated based on the difference in the fluorescence level obtained by subtracting the fluorescence intensity before addition of the compound from the maximum fluorescence intensity after the addition thereof. The results are shown in Table 1. The activity of the test compound is shown by the ratio (%) relative to the maximum response by 5-HT.

TABLE 1

| Example No. of test compound | ratio (%) relative to maximum response by 5-HT (10 μM) |
|---|---|
| 1 | 104 |
| 2 | 107 |
| 3 | 106 |
| 4 | 100 |
| 5 | 108 |
| 6 | 98 |
| 7 | 97 |
| 8 | 105 |
| 9 | 109 |
| 10 | 100 |
| 11 | 102 |
| 12 | 102 |
| 13 | 81 |
| 14 | 87 |
| 15 | 98 |

TABLE 1-continued

| Example No. of test compound | ratio (%) relative to maximum response by 5-HT (10 μM) |
|---|---|
| 16 | 101 |
| 17 | 99 |
| 18 | 105 |
| 19 | 96 |
| 20 | 94 |
| 21 | 109 |
| 22 | 105 |
| 23 | 100 |
| 24 | 96 |
| 25 | 96 |
| 26 | 98 |
| 29 | 93 |
| 30 | 94 |
| 31 | 85 |
| 32 | 97 |
| 33 | 94 |
| 34 | 77 |
| 35 | 99 |
| 36 | 79 |
| 37 | 95 |
| 38 | 93 |
| 39 | 93 |
| 40 | 93 |
| 41 | 91 |
| 42 | 102 |
| 43 | 107 |

Industrial Applicability

Since the compound of the present invention has a superior serotonin 5-HT$_{2C}$ receptor activating action or a salt thereof, it is useful as a safe agent for treatment or the prophylaxis of all serotonin 5-HT$_{2C}$-related disease such as a lower urinary tract symptom, obesity and/or organ prolapse and the like.

The invention claimed is:

1. A compound represented by the formula (1)

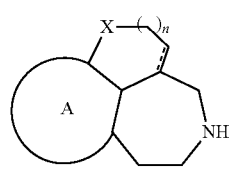

(1)

wherein
ring A is benzene optionally having substituent(s),
X is —N(R$^1$)—,
R$^1$ is a hydrogen atom, an alkyl group optionally having substituent(s), a cycloalkyl group optionally having substituent(s), an alkylcarbonyl group optionally having substituent(s), an arylcarbonyl group optionally having substituent(s), an alkoxycarbonyl group optionally having substituent(s), or an alkylsulfonyl group optionally having substituent(s),
------ is a single bond, and
n is 0,
or a salt thereof.

2. The compound or salt of claim 1, which is a compound represented by the formula (2)

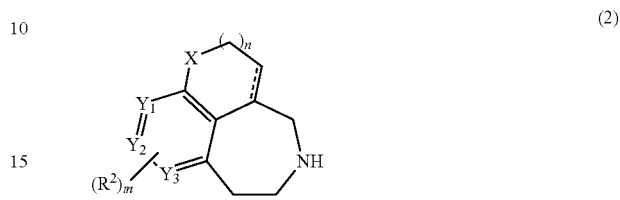

(2)

wherein
X is —N(R$^1$)—,
R$^1$ is a hydrogen atom, an alkyl group optionally having substituent(s), a cycloalkyl group optionally having substituent(s), an alkylcarbonyl group optionally having substituent(s), an arylcarbonyl group optionally having substituent(s), an alkoxycarbonyl group optionally having substituent(s), an alkylsulfonyl group optionally having substituent(s) or an alkylsulfinyl group optionally having substituent(s),
------ is a single bond,
Y$_1$, Y$_2$ and Y$_3$ are all carbon atoms,
R$^2$ are the same or different and each is a hydrogen atom, a halogen atom, an alkyl group optionally having substituent(s), an alkoxy group optionally having substituent(s), an alkoxycarbonyl group optionally having substituent(s), an alkylcarbonyl group optionally having substituent(s), an aryl group optionally having substituent(s), an amino group, or an N-alkylamino group,
m is an integer of 1, 2 or 3, and
n is 0,
or a salt thereof.

3. The compound or salt of claim 2, wherein R$^2$ is a halogen atom or an alkyl group optionally having substituent(s).

4. (2aS)-9-Chloro-1-isopropyl-2,2a,3,4,5,6-hexahydro-1H-azepino[3,4,5-cd]indole, or a salt thereof.

5. 9-Chloro-2,2a,3,4,5,6-hexahydro-1H-azepino[3,4,5-cd]indole, or a salt thereof.

6. 9-Isopropyl-1-methyl-2,2a,3,4,5,6-hexahydro-1H-azepino[3,4,5-cd]indole, or a salt thereof.

7. A pharmaceutical composition comprising the compound or salt of claim 1, and pharmacologically acceptable carrier.

8. A method for the treatment of a lower urinary tract symptom, obesity and/or organ prolapse, which comprises administering an effective amount of the compound or salt of claim 1 to a mammal.

* * * * *